(12) United States Patent
Chan

(10) Patent No.: US 7,356,866 B2
(45) Date of Patent: Apr. 15, 2008

(54) MODULAR ELECTRIC TOOTHBRUSHES

(75) Inventor: John Geoffrey Chan, Loveland, OH (US)

(73) Assignee: Church & Dwight Co., Inc., Princeton, NJ (US)

( * ) Notice: Subject to any disclaimer, the term of this patent is extended or adjusted under 35 U.S.C. 154(b) by 662 days.

(21) Appl. No.: 10/730,850

(22) Filed: Dec. 9, 2003

(65) Prior Publication Data
US 2005/0022323 A1 Feb. 3, 2005

Related U.S. Application Data

(63) Continuation-in-part of application No. 10/274,700, filed on Oct. 21, 2002, now abandoned.

(60) Provisional application No. 60/387,841, filed on Jun. 11, 2002, provisional application No. 60/410,865, filed on Sep. 13, 2002, provisional application No. 60/410,556, filed on Sep. 13, 2002.

(51) Int. Cl.
*A46B 13/02* (2006.01)
*A61C 17/22* (2006.01)

(52) U.S. Cl. ............................... 15/22.1; 15/28

(58) Field of Classification Search ............... 15/22.1, 15/22.2, 28
See application file for complete search history.

(56) References Cited

U.S. PATENT DOCUMENTS

| | | |
|---|---|---|
| 3,015,833 A | 1/1962 | Gilet |
| 3,524,088 A | 8/1970 | Ryckman, Jr. |
| 3,775,800 A | 12/1973 | Veneziani |
| 4,081,876 A | 4/1978 | Pugh |
| 4,156,620 A | 5/1979 | Clemens |

(Continued)

FOREIGN PATENT DOCUMENTS

AU 733458 3/2001

(Continued)

*Primary Examiner*—Randall Chin
(74) *Attorney, Agent, or Firm*—K. Bradford Adolphson; Keith Obert

(57) ABSTRACT

An electric toothbrush having movable and static carriers which independently slidingly engage the receiving member of the toothbrush head within channels defined by the surfaces of the receiving member. Such carriers can be releasably removable to replace or exchange the carriers. Also disclosed is a toothbrush having a unique assembly utilizing a one-piece housing in combination with a movable bristle carrier that is engaged on a receiving member located at the distal end of the toothbrush, and a static carrier such as a brush head tip which is secured thereto. The unitary housing reduces the number of components of the toothbrush and decreases manufacturing costs. The static and movable carriers may be replaced with other carriers and allows a consumer to individually tailor the brush to provide a particular brushing configuration. An electric toothbrush having a particular assembly, bristle configuration, and drive mechanism is disclosed. The assembly, bristle configuration, and drive mechanism are such that operation of the brush is highly efficient and more economical than currently known toothbrushes. Specifically, an electric toothbrush is disclosed comprising a body, a head, and a neck extending therebetween. The head comprises a receiving member and several unique and preferred arrangements of static and movable carriers. The carriers can comprise bristles, and the static bristle carrier(s) can at least partially surround the collection of movable bristle carrier(s). A motor and drive train impart motion to the movable carrier(s).

17 Claims, 25 Drawing Sheets

U.S. PATENT DOCUMENTS

| | | | |
|---|---|---|---|
| 4,203,431 A | 5/1980 | Abura et al. | |
| 4,827,550 A | 5/1989 | Graham et al. | |
| 4,845,795 A | 7/1989 | Crawford et al. | |
| 4,894,880 A | 1/1990 | Aznavoorian | |
| 4,989,287 A | 2/1991 | Scherer | |
| 5,033,150 A | 7/1991 | Gross et al. | |
| 5,046,213 A | 9/1991 | Curtis et al. | |
| 5,120,225 A | 6/1992 | Amit | |
| D330,286 S | 10/1992 | Curtis et al. | |
| 5,186,627 A | 2/1993 | Amit et al. | |
| 5,226,206 A | 7/1993 | Davidovitz et al. | |
| 5,253,382 A | 10/1993 | Beny | |
| 5,335,389 A | 8/1994 | Curtis et al. | |
| 5,353,460 A | 10/1994 | Bauman | |
| 5,359,747 A | 11/1994 | Amakasu | |
| 5,383,242 A | 1/1995 | Bigler et al. | |
| 5,392,483 A | 2/1995 | Heinzelman et al. | |
| 5,404,608 A | 4/1995 | Hommann | |
| 5,416,942 A | 5/1995 | Baldacci et al. | |
| 5,446,940 A | 9/1995 | Curtis et al. | |
| 5,448,792 A | 9/1995 | Wiedemann et al. | |
| 5,465,444 A | 11/1995 | Bigler et al. | |
| 5,500,970 A | 3/1996 | Maurer et al. | |
| 5,504,959 A | 4/1996 | Yukawa et al. | |
| 5,524,312 A | 6/1996 | Tan et al. | |
| 5,617,601 A | 4/1997 | McDougall | |
| 5,735,011 A | 4/1998 | Asher | |
| 5,836,030 A | 11/1998 | Hazeu et al. | |
| 5,842,245 A | 12/1998 | Pai | |
| 5,851,551 A | 12/1998 | Tseng et al. | |
| 5,876,206 A | 3/1999 | Maurer | |
| 5,926,897 A | 7/1999 | Volpenhein | |
| 5,930,860 A | 8/1999 | Shipp | |
| 5,987,688 A | 11/1999 | Roberts et al. | |
| 6,000,083 A | 12/1999 | Blaustein et al. | |
| 6,006,394 A | 12/1999 | Bredall et al. | |
| D432,312 S | 10/2000 | Blaustein et al. | |
| D433,814 S | 11/2000 | Blaustein et al. | |
| 6,148,462 A | 11/2000 | Zseng | |
| D434,563 S | 12/2000 | Lim et al. | |
| 6,178,579 B1 | 1/2001 | Blaustein et al. | |
| 6,189,693 B1 | 2/2001 | Blaustein et al. | |
| 6,237,178 B1 | 5/2001 | Krammer et al. | |
| 6,311,837 B1 | 11/2001 | Blaustein et al. | |
| 6,314,605 B1 | 11/2001 | Solanki et al. | |
| 6,360,395 B2 | 3/2002 | Blaustein et al. | |
| 6,371,294 B1 | 4/2002 | Blaustein et al. | |
| D456,998 S | 5/2002 | Blaustein et al. | |
| D457,728 S | 5/2002 | Blaustein et al. | |
| D458,030 S | 6/2002 | Blaustein et al. | |
| D458,455 S | 6/2002 | Blaustein et al. | |
| D459,584 S | 7/2002 | Blaustein et al. | |
| D459,894 S | 7/2002 | Blaustein et al. | |
| D459,895 S | 7/2002 | Blaustein et al. | |
| D461,642 S | 8/2002 | Blaustein et al. | |
| 6,453,499 B1 | 9/2002 | Leuermann | |
| D465,088 S | 11/2002 | Blaustein et al. | |
| 6,546,585 B1 | 4/2003 | Blaustein et al. | |
| 6,564,940 B2 | 5/2003 | Blaustein et al. | |
| 6,581,233 B1 | 6/2003 | Cheng et al. | |
| D476,486 S | 7/2003 | Whitney et al. | |
| D483,182 S | 12/2003 | Blaustein et al. | |
| 6,725,490 B2 * | 4/2004 | Blaustein et al. | 15/22.2 |
| 6,836,917 B2 | 1/2005 | Blaustein et al. | |
| 6,889,401 B2 | 5/2005 | Fattori et al. | |
| 2001/0022277 A1 | 9/2001 | Blaustein et al. | |
| 2002/0020645 A1 | 2/2002 | Blaustein et al. | |
| 2002/0029988 A1 | 3/2002 | Blaustein et al. | |
| 2002/0032941 A1 | 3/2002 | Blaustein et al. | |
| 2002/0078514 A1 | 6/2002 | Blaustein et al. | |
| 2002/0162180 A1 | 11/2002 | Blaustein et al. | |
| 2003/0033679 A1 * | 2/2003 | Fattori et al. | 15/22.1 |
| 2003/0140435 A1 | 7/2003 | Eliav et al. | |
| 2003/0140437 A1 * | 7/2003 | Eliav et al. | 15/22.2 |
| 2003/0196283 A1 * | 10/2003 | Eliav et al. | 15/22.1 |
| 2003/0226223 A1 | 12/2003 | Chan | |
| 2005/0204491 A1 * | 9/2005 | Gatzemeyer et al. | 15/22.1 |

FOREIGN PATENT DOCUMENTS

| | | |
|---|---|---|
| CA | 985975 | 3/1976 |
| CA | 1082408 | 7/1980 |
| CA | 1191003 | 7/1985 |
| CA | 96826 | 7/2002 |
| CA | 2465902 | 5/2003 |
| CN | 2274947 | 2/1998 |
| DE | 1244709 | 7/1967 |
| DE | 2736286 | 7/1978 |
| DE | 29517610 | 4/1997 |
| EP | 054043 | 11/1985 |
| EP | 651978 | 10/1995 |
| FR | 1357566 | 4/1964 |
| FR | 1357570 | 4/1964 |
| FR | 1414679 | 9/1965 |
| FR | 2368854 | 5/1978 |
| FR | 2616306 | 12/1988 |
| GB | 1240438 | 7/1971 |
| GB | 1293876 | 10/1972 |
| GB | 2005999 | 5/1979 |
| GB | 1583558 | 1/1981 |
| GB | 2089042 | 3/2001 |
| GB | 2094145 | 3/2001 |
| GB | 2097844 | 3/2001 |
| GB | 2097845 | 3/2001 |
| GB | 3008453 | 5/2003 |
| GB | 3004567 | 9/2003 |
| GB | 3004568 | 9/2003 |
| GB | 3014059 | 9/2003 |
| GB | 3014060 | 9/2003 |
| GB | 3006685 | 10/2003 |
| GB | 3006686 | 10/2003 |
| JP | 5-146313 | 6/1993 |
| JP | 5-146314 | 6/1993 |
| JP | 5-199917 | 8/1993 |
| JP | 5-269024 | 10/1993 |
| JP | 6-26552 D1 | 4/1994 |
| JP | 6-121710 | 5/1994 |
| JP | 6-189822 | 7/1994 |
| JP | 6-245819 | 9/1994 |
| JP | 6-245820 | 9/1994 |
| JP | 7-116020 | 5/1995 |
| JP | 7-116024 | 5/1995 |
| JP | 7-93892 | 10/1995 |
| JP | 8-000356 | 1/1996 |
| JP | 8-103331 | 4/1996 |
| JP | 2540444 | 4/1997 |
| JP | 2656178 | 5/1997 |
| JP | 2719556 | 11/1997 |
| JP | 10-66704 | 3/1998 |
| JP | 2804940 | 7/1998 |
| JP | 2811246 | 8/1998 |
| JP | 3005608 | 11/1999 |
| JP | 3045412 | 3/2000 |
| JP | 1149976 | 6/2002 |
| KR | 1997-0000408 | 1/1997 |
| KR | 1997-0000409 | 1/1997 |
| KR | 125188 | 10/1997 |
| TW | 26360 | 3/1978 |
| TW | 212909 | 9/1993 |
| WO | WO 91/13570 | 9/1991 |
| WO | 92/17092 | 10/1992 |
| WO | 94/13870 | 6/1994 |
| WO | WO 96/09019 | 3/1996 |
| WO | WO 96/10373 | 4/1996 |

| WO | WO 96/38100 | 12/1996 |
| WO | 98/04167 | 2/1998 |
| WO | 99/23910 | 5/1999 |
| WO | 01/29128 | 4/2001 |
| WO | 01/60281 | 8/2001 |
| WO | WO 03/039396 A1 | 5/2003 |
| WO | 03/063722 | 8/2003 |
| WO | WO 03/082049 A1 | 10/2003 |
| WO | WO 03/082050 A1 | 10/2003 |
| WO | 03/103531 | 12/2003 |

* cited by examiner

MODULAR ELECTRIC TOOTHBRUSHES

CROSS REFERENCE TO RELATED APPLICATION

This application is a continuation-in-part of application Ser. No. 10/274,700 filed on Oct. 21, 2002, now abandoned, which claims priority to U.S. Provisional Applications Ser. No. 60/387,841 filed Jun. 11, 2002; Ser. No. 60/410,865 filed Sep. 13, 2002; and Ser. No. 60/410,556 filed Sep. 13, 2002 all of which are wherein incorporated by reference.

FIELD OF THE INVENTION

The present invention relates to electric toothbrushes and more particularly, modular electric toothbrushes having interchangeable or replaceable components and electric toothbrushes having high efficiency.

BACKGROUND OF THE INVENTION

The present invention relates generally to electric toothbrushes. More particularly, it relates to an improved electric toothbrush with replaceable or exchangeable movable and/or static bristle carriers. Although many different electric toothbrushes exists which offer different advantages and characteristics, these characteristics can increase the costs associated with the toothbrush and can be reflected in higher retail prices for the product. Accordingly, it would be desirable to provide an electric toothbrush that was relatively inexpensive to assemble and produce, but provides the cleaning efficacy and toothbrush characteristics desired by the consumer.

Electric toothbrushes are also known in which certain components of the brush may be interchanged or replaced with like components from other toothbrushes or components that are sold separately. For example, toothbrushes having replaceable head and neck assemblies are known in which the entire head and at least a portion of the neck may be removed from a toothbrush body or its housing, and replaced with another head and neck assembly. U.S. application Ser. No. 09/850,662, now U.S. Pat. No. 6,836,917, teaches an electric toothbrush having a replaceable brush head. Although significant advantages can be gained by such a modular system, entire toothbrush head and neck assemblies are relatively expensive. Additionally, often a replacement of the entire head and neck assembly is unnecessary when only the bristles are worn. Accordingly, a need exists for an alternative modular design for a toothbrush which can be tailored to a consumer's particular needs. For example, a consumer could exchange and/or replace a portion of the toothbrush head for a particular task, or if a portion of the toothbrush head was worn.

SUMMARY OF THE INVENTION

The present invention relates to an electric toothbrush comprising a handle at a first end of the toothbrush having a motor disposed therein; a neck extending from the handle comprising a receiving member at a second end of the toothbrush, wherein a plurality of carriers engage the receiving member, and wherein the carriers comprise one or more static carrier(s) and one or more movable carrier(s), and wherein the one or more static carrier(s) and one or more movable carrier(s) independently slidingly engage the receiving member of the toothbrush; and a drive shaft operatively connecting the one or more movable carrier(s) to the motor.

The invention also relates to kits comprising the aforementioned electric toothbrush and one or more static and one or more movable carriers selected from the group consisting of, but are not limited to, brush head tip carriers, static bristle carriers, movable bristle carriers, elastomeric element carriers, oral care composition carriers, and/or dental tool carriers, and/or combinations thereof.

The present invention further relates to a low energy consumption electric toothbrush comprising; a housing assembly including a brush head, a handle, and a neck extending between the brush head and the handle, the housing defining a hollow interior cavity; a movable bristle carrier disposed on the brush head; a motor providing a powered rotating shaft, a drive gear affixed to the shaft, and a power source in electrical communication with the motor and disposed in the hollow interior cavity, a crown gear rotatably supported in the hollow interior cavity and oriented such that the axis of rotation of the crown gear is perpendicular to an axis of rotation of the motor and the drive gear, the crown gear configured and engaged with the drive gear of the motor such that the crown gear completes one revolution for a number, from one to three, of revolutions of the motor, the crown gear including (i) a first cam member extending from a face of the crown gear, the first cam having a center offset from the axis of rotation of the crown gear and (ii) a second cam member extending from a face of the first cam member, the second cam member having an axis of rotation co-extensive with the axis of rotation of the crown gear; a drive shaft having a first end and a second opposite end, the first end engaged with the first cam member and the second cam member of the crown gear, and the second end engaged with the movable bristle carrier; a first plurality of bristles retained on the movable bristle carrier; a second plurality of stationary bristles retained on the brush head; wherein upon operation of the motor, the crown gear is rotated, thereby imparting a reciprocating motion to the drive shaft and to the movable bristle carrier disposed on the brush head.

BRIEF DESCRIPTION OF THE DRAWINGS

The present invention may take form in various components and arrangements of components, and in various techniques, methods, or procedures and arrangements of steps. The referenced drawings are only for purposes of illustrating embodiments, they are not necessarily to scale, and are not to be construed as limiting the present invention.

It is believed that the present invention will be better understood from the following description taken in conjunction with the accompanying drawings in which.

DETAILED DESCRIPTION OF THE INVENTION

Figure 1:
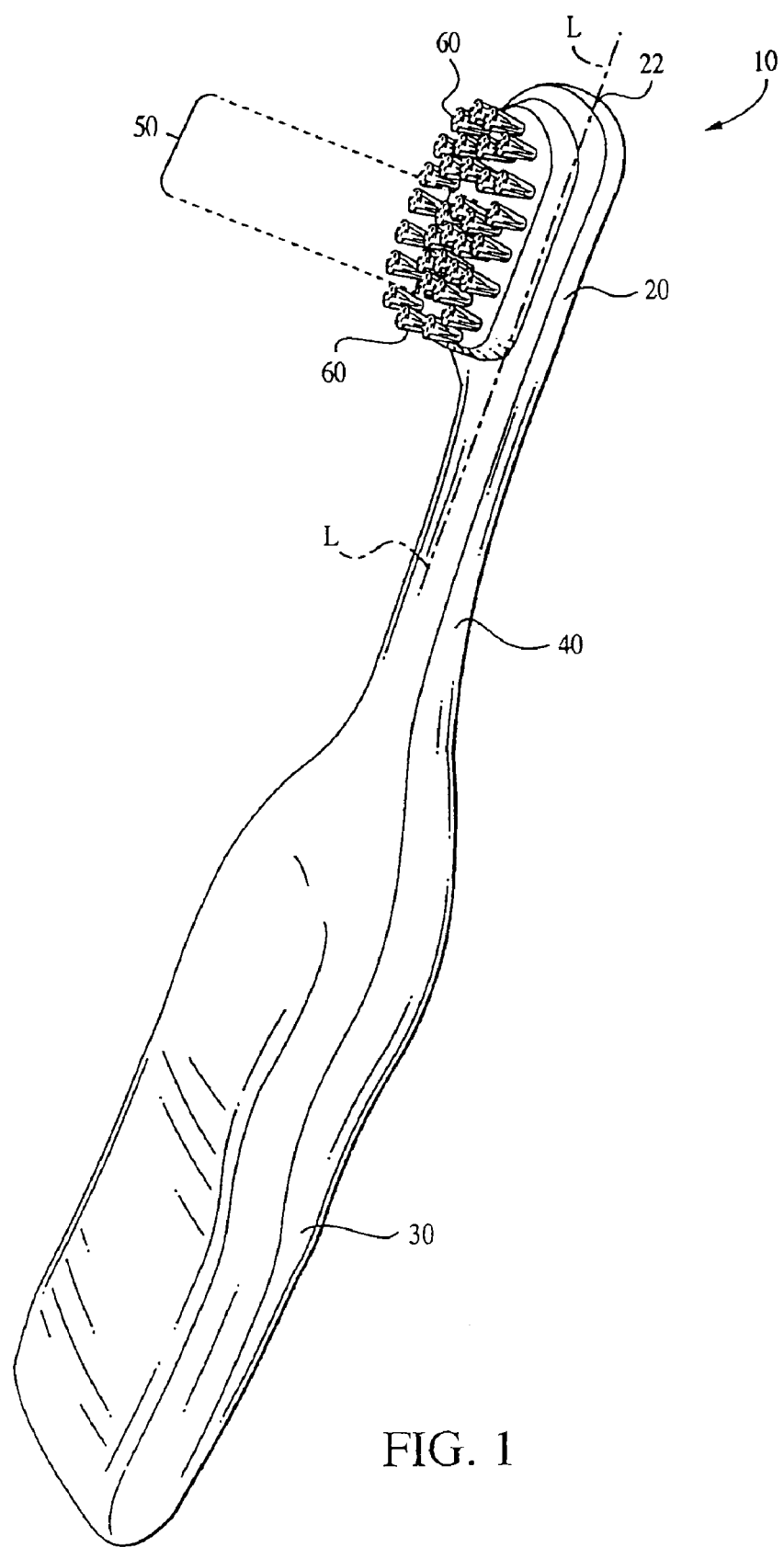
FIG. 1 is a perspective view of the toothbrush in accordance with the present invention.

The present invention is based upon a discovery that significant cleaning efficacy results from a toothbrush that utilizes a combination of static bristles, and movable bristles that are powered. Preferably, the movable bristles reciprocate when powered, and most preferably, the movable bristles reciprocate in a direction generally parallel to the longitudinal axis of the toothbrush. It is contemplated that the movable bristles may also reciprocate in a direction generally perpendicular to the longitudinal axis. Although reciprocation is the preferred type of movement for the movable bristle carrier, the present invention encompasses other types of movement for the movable bristle carrier. In all of the preferred embodiments described herein, the various movable bristles are all powered or carried by a single movable component. This is described in greater detail herein. The present invention is also based upon a discovery of particular patterns or configurations for the static bristles, particularly when utilized in conjunction with the movable and powered bristle set. Furthermore, the present inventive toothbrush, featuring a movable bristle carrier that reciprocates and which is at least partially surrounded by an array of static bristles, is particularly well suited for large scale manufacturing. That is, the various preferred embodiment brushes described herein are relatively inexpensive to manufacture as a result of their remarkable simplicity and novel structure. These and other aspects are described herein.

The present invention is also based upon a unique design for a unitary body or housing for an electric toothbrush that incorporates an integral neck and brush head assembly. The one-piece body or housing greatly simplifies assembly of the toothbrush and reduces manufacturing costs associated with the brush. The present invention also provides a novel modular design for the brush head that enables a user to choose the bristles and/or elements for the brush head. This novel modular design can be achieved by engaging one or more static carrier(s) and one or more movable carrier(s) with a receiving member extending from the distal end of the neck of the toothbrush. A carrier is an element, such as a plate, which engages the receiving member and which may contain structures or compositions that interact with the oral cavity tissue and/or teeth. The plurality of static and/or movable carriers can include, but are not limited to, bristle carriers, brush head tip carriers, elastomeric element carriers, oral care composition carriers, and dental tool carriers, or any combination thereof. The plurality of static and/or movable carriers can be of many shapes and sizes, so long as the carriers can engage the receiving member of the toothbrush. In one embodiment the static carrier(s) can be a static bristle carrier, and/or the movable carrier(s) can be a movable bristle carrier. The plurality of carriers can be brush head tips. Brush head tip carriers can be located on the distal most portion of the toothbrush head. These brush head tips can constitute a relatively large portion of the brush head. Certain embodiments of the invention include these aforementioned elastomeric elements or flexible, outwardly extending members that are disposed on the brush head. The static carrier and the moving carrier of the toothbrush head also may include elastomeric elements along with the bristles. The static portion and the moving portion can each include bristles and elastomeric elements, which are used for gently massaging the user's gums while brushing. The elastomeric elements can be located on the perimeter of the static and moving portions or among the bristles on the static and moving portions of the brush head, and can be formed from any elastomeric material including, but not limited to, rubber. Elastomeric elements include, but are not limited to, those discussed in U.S. Pat. Nos. 5,987,688, and 5,735,011 that are incorporated herein by reference. The dental tool supported and/or conveyed by the carriers include, but are not limited to, gum massaging tools, scraping tools, cleaning tools, flossing tools, polishing cups, rubber picks and applicators. For instance, elements and/or tools that are specifically designed for applying whitening agents to the teeth may be used. An example of polishing cups include, but are not limited to, those discussed in U.S. Pat. No. 5,930,860 incorporated herein by reference. Additionally, bristle arrangements that provide gum and interdental stimulation may be used, such as discussed in U.S. Pat. No. 5,926,897 incorporated herein by reference. Oral care compositions include, but are not limited to, compositions disposed on/within a carrier or delivered by a carrier for the care or treatment of the teeth or oral tissue, and/or other compositions placed on/within a carrier which facilitate the treatment and/or care of the teeth and oral tissue. Examples of oral care compositions include, but are not limited to, tartar control compositions, tooth whitening compositions, abrasives, fluoride, and oral sensation compositions such as flavoring. Examples of oral care composition carriers include, but are not limited to, those disclosed in U.S. Pat. No. 5,851,551, and applications WO09413870A1, WO9804167A1, incorporated herein by reference.

Before describing the various embodiments of the inventive toothbrush, it is instructive to define the various types of motions that the movable bristles may undergo. As used herein, the term "angular motion" refers to any angular displacement. "Linear motion" is movement along a straight or substantially straight, line or direction. "Primarily linear motion" is described below. "Curvilinear motion" is movement that is neither completely linear nor completely angular but is a combination of the two (e.g., curvilinear). These motions can be constant or periodic. Constant motion refers to motion that does not change direction or path (i.e., is unidirectional). Periodic motion refers to motion that reverses direction or path. Constant angular motion (i.e., motion that extends through 360 degrees or more) that is substantially in the form of a circle is referred to as rotary motion. Periodic angular motion is motion that extends through less than 360 degrees and is referred to as oscillating motion. Curvilinear motions can also be either constant (i.e., unidirectional) or periodic (i.e., reverses direction). Periodic linear motion is referred to as "reciprocation". The above-described motions can also occur along one or more axes of a bristle carrier.

Furthermore, it is useful to define the term "static" bristles and the term "movable" bristles. The term static bristles refer to bristles that are secured or static to the brush head or body of the toothbrush or other component thereof so that the bristles, and specifically, the base of the bristles, do not move with regard to the toothbrush during use. Restated, static bristles refer to bristles that are fixed to the toothbrush such that their base or point of attachment does not move with respect to the toothbrush, and the static bristles are not operatively connected to the drive shaft. The static bristles can be affixed to a static carrier. One or more of these static bristle carriers can then engage the receiving member of the toothbrush, to form the toothbrush head. Although these carriers and the bristles disposed thereon are static, it is recognized that the ends of the bristles or regions distal from the base of a bristle or group of bristles may move as a result of flexing of the bristle, but the base of the static bristle does not move with respect to the toothbrush. Additionally, the static carrier on which the bristles can be disposed can be slideably released from the toothbrush. Thus the user can replace and/or exchange the static carriers as needed. Any movement of the bristles does not result from an operative connection to the drive shaft and/or motor, as opposed to movable bristles, which do move as a result of an operative connection to the drive shaft.

The term movable bristle refers to a bristle in which the base of the bristle moves with respect to the toothbrush, and preferably with respect to the longitudinal axis of the brush. Generally, this configuration is accomplished by affixing or supporting the base of the bristle to a mounting component, such as a carrier that is movable with respect to the brush. The one or more movable bristle carrier(s) can then engage the receiving member of the toothbrush, to complete the formation of the toothbrush head. Restated, a movable bristle is a bristle that is movable, and preferably, slideably moves with respect to the longitudinal axis of the brush as a result of an operative connection with the drive shaft.

The novel modular design of the inventive toothbrush can be achieved by the unique structure of the brush head. As used herein, the phrase "toothbrush head" comprises one or more static carrier(s) and one or more movable carrier(s), and the receiving member. The one or more static carrier(s) and the one or more movable carrier(s) engage the toothbrush via a receiving member. The receiving member is located at the distal end of the neck of the toothbrush and retains the carriers. The receiving member can be provided with bristles, or the receiving member can be devoid of bristles.

In either instance, the head of the toothbrush can be formed by the sliding engagement of the one or more static carrier(s) and the one or more movable carrier(s) to the receiving member. In one embodiment, the static carrier engages the receiving member, and can substantially surround the movable carrier. In another embodiment a plurality of static carriers engage the receiving member, such that when the plurality is engaged, the static carriers can substantially surround the movable carrier. Embodiments of the modular design of the present invention include toothbrushes wherein the one or more static carrier(s) and the one or more movable carrier(s) comprise bristles. The one or more static bristle carrier(s) and the one or more movable bristle carrier(s) independently, slidingly engage the receiving member, located at the distal end of the neck of the toothbrush. This receiving member can provide support for the one or more static bristle carrier(s) and the one or more movable bristle carrier(s). Additionally, other carriers can engage the receiving member of the toothbrush including, but not limited to, dental tool carriers, elastomeric element carriers, oral care composition carriers, and/or combinations thereof.

Referring to FIG. 1, a preferred embodiment toothbrush 10 according to the present invention is illustrated. The toothbrush 10 comprises a body 30, a head 20 and a neck 40 extending between the body 30 and the head 20. The head 20 defines a distal-most end 22. The head 20 and the neck 40 generally extend along a longitudinal axis illustrated in FIG. 1 as axis L. Disposed along the head 20 are a plurality of static bristles 60 and a collection of interiorly disposed bristles 50 which are movable as described herein. The movable bristles 50 are supported on and retained by a movable bristle carrier. The movable bristle carrier may undergo a wide variety of motions as noted above.

Figure 2:
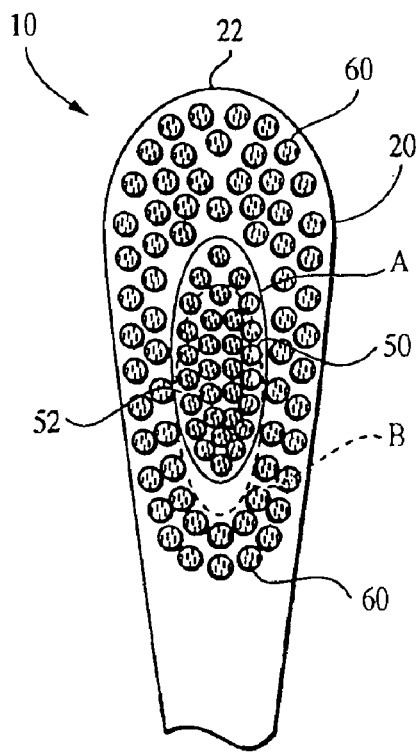
FIG. 2 is a bottom view of a toothbrush head showing a configuration of various bristle types according to the present invention.

FIGS. 2-5 and 13 illustrate various configurations for the arrangement of the static bristles and the movable bristles in accordance with the invention. FIG. 2 is a detail view of the toothbrush 10 shown in FIG. 1 and its head 20. As can be seen from FIG. 2, the static bristles 60 generally extend entirely around the collection of movable bristles 50. The movable bristles 50 are disposed and situated on a movable bristle carrier 52. The bristle carrier 52 is preferably movable between two positions shown in FIG. 2 as position A and position B. Preferably, the bristle carrier 52 may be moved back and forth between position A, in which the bristle carrier 52 is proximate the distal-most end 22 of the brush head 20, and position B shown in FIG. 2 by dashed lines. Most preferably, the direction of movement of the bristle carrier 52 as it reciprocates between positions A and B is generally parallel to the longitudinal axis of the head 20 and neck (not shown in FIG. 2) as noted in FIG. 1 as axis L.

Figure 3:
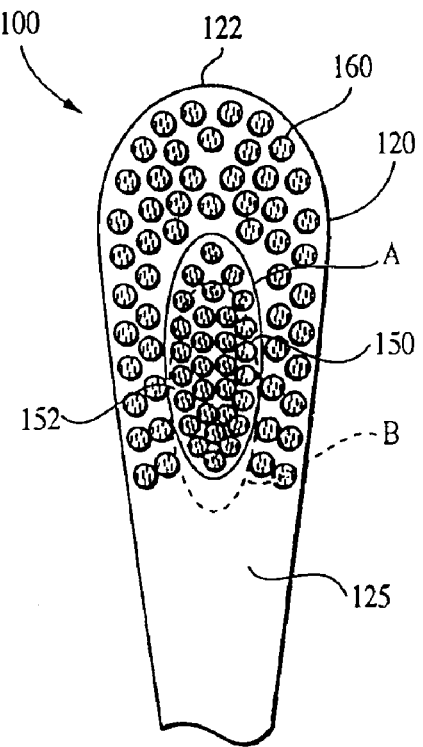
FIG. 3 is another bottom view of a toothbrush head showing a configuration of bristle arrangements according to the present invention.

FIG. 3 illustrates another arrangement of bristles along a brush head 120 of a toothbrush 100 according to the present invention. In this embodiment, a plurality of static bristles 160 extend substantially around the periphery or perimeter of a collection of movable bristles 150. The movable bristles 150 are supported and retained along a movable bristle carrier 152. The bristle carrier 152 is movable between two positions A and B shown in FIG. 3. In this preferred configuration, the region 125 along the brush head 120 does not contain any bristles, either static bristles or movable bristles. As previously described with respect to FIG. 2, the bristle carrier 152, and thus movable bristles 150, preferably may reciprocate between positions A and B. As will be noted from FIG. 3, position A is proximate the distal-most end 122 of the brush head 120.

Figure 4:
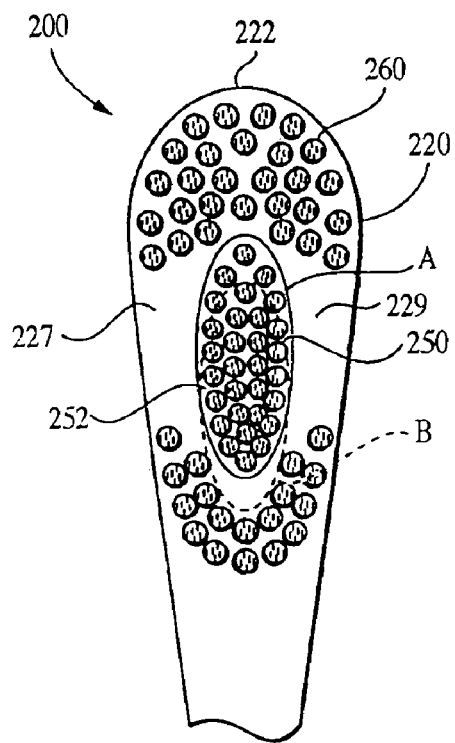
FIG. 4 is another bottom view of a toothbrush head showing a configuration of bristle arrangements according to the present invention.

FIG. 4 illustrates another embodiment of the toothbrush head 220 of a toothbrush 200 according to the present invention. In this embodiment, a collection of static bristles 260 are located at opposite regions of the brush head 220 around a collection of movable bristles 250. The movable bristles 250 are supported and retained along a movable bristle carrier 252. The movable bristle carrier 252 is movable between position A and position B as shown in FIG. 4. It will be noted that two regions are defined, between the collection of static bristles 260, which do not contain any bristles. These regions are designated in FIG. 4 as regions 227, 229. As previously noted with respect to FIG. 2, the bristle carrier 252, and thus the movable bristles 250, preferably may reciprocate between positions A and B. Position A is proximate the distal-most end 222 of the brush head 220.

Figure 5:
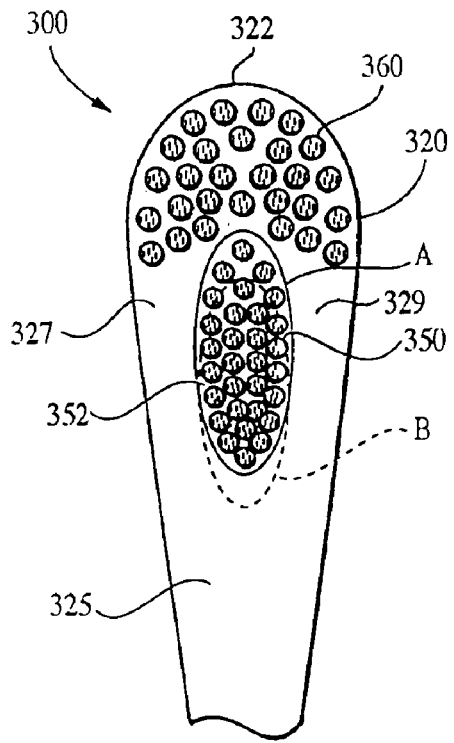
FIG. 5 is yet another bottom view of a toothbrush head showing a configuration of bristle arrangements according to the present invention.

FIG. 5 illustrates yet another preferred embodiment toothbrush head 320 of a toothbrush 300 in accordance with the present invention. In this embodiment, a collection of static bristles 360 extend only partially around a collection of movable bristles 350 supported and retained on a movable bristle carrier 352. The movable bristle carrier 352 is movable between two positions shown in FIG. 5 as positions A and B. It will be noted that regions 329, 327, 325 are defined around the periphery of the collection of movable bristles 350. These regions do not contain any bristles and particularly do not contain any static bristles 360. As previously noted with regard to FIG. 2, the bristle carrier 352, and thus the movable bristles 350, preferably may reciprocate between positions A and B. Position A is proximate the distal-most end 322 of the brush head 320.

Figure 13:
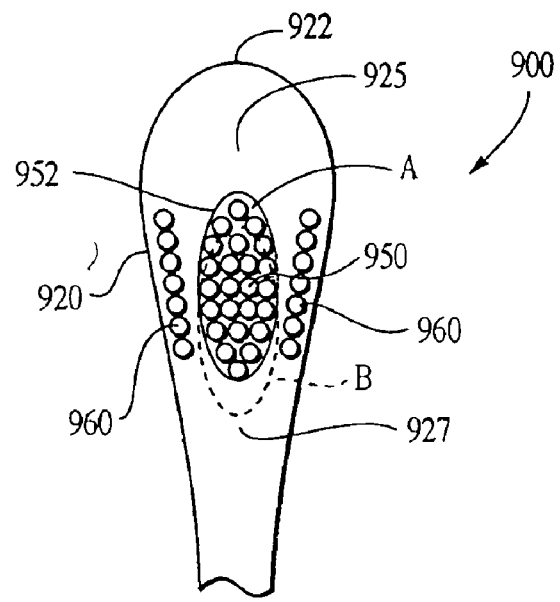
FIG. 13 is a bottom view of a toothbrush head showing a configuration of bristle arrangements according to the present invention.

FIG. 13 illustrates another embodiment of the toothbrush head 920 of a toothbrush 900 according to the present invention. In this embodiment, a collection of static bristles 960 are located at opposite regions of the brush head 220 around a collection of movable bristles 950. Specifically, the static bristles 960 are located along the sides of the brush head 920. Regions 925 and 927 are defined between the groups of static bristles, and preferably as shown in FIG. 13. The movable bristles 950 are supported and retained along a movable bristle carrier 952. The movable bristle carrier 952 is movable between position A and position B as shown in FIG. 13. As previously noted with respect to FIG. 2, the bristle carrier 952, and thus the movable bristles 950, preferably may reciprocate between positions A and B. Position A is proximate the distal-most end 922 of the brush head 920.

It will be noted that the preferred bristle configurations are based upon the movable bristles located generally within a middle region or interior of the brush head, and static bristles at least partially surrounding the medially disposed movable bristles. This is explained in greater detail herein.

For certain applications, it is preferred that the static bristles surround 100% of the perimeter or periphery of the collection of movable bristles. In other applications, it is preferred that the static bristles surround or extend along about 75% to about 100% of the perimeter of the movable bristles. In still other applications, it is preferred that the static bristles extend along about 50% to about 75% of the perimeter of the movable bristles. In further applications, it is preferred that the static bristles extend along about 25% to about 50% of the perimeter of the movable bristles. And in other applications, it may be preferred that the static bristles extend less than 25% around the perimeter of the movable bristles. As noted, the static bristles preferably extend along at least a portion of the outer periphery of the collection of movable bristles. It is not necessary for certain embodiments that the static bristles extend continuously about the periphery of the set of movable bristles. That is, the present invention encompasses bristle configurations in which the static bristles extend intermittently along or about the outer periphery of the collection of movable bristles.

The terms "completely encircling (or encircle)", "substantially encircling (or encircle)", "partially encircling (or encircle)", and "partially surrounding (or encircle)" are used herein to refer to particular configurations of static bristles and their relative location with respect to the movable bristles. The term "completely encircling" refers to a configuration in which the static bristles completely encircle, or are located entirely around, the perimeter of the movable bristles. It will be understood that when static bristles are described as encircling or extending along the perimeter or portion thereof of the movable bristles, minute or relatively small spaces may exist between individual bristles or groups of bristles. These spaces are on the order of only 1 to 10 diameters of a typical bristle. The term "substantially encircling" refers to a configuration in which the static bristles extend along at least 80% of the perimeter of the movable bristles. Specifically, substantially encircle includes configurations in which the static bristles extend along 80% or more, 90% or more, or 95% or more of the perimeter of the movable bristles. The term "partially encircling" refers to a configuration in which the static bristles extend along a portion of the perimeter of the movable bristles, and preferably, extend along a portion that is less than 80% of the distance along that perimeter. The term "partially surrounding" refers to a configuration in which the static bristles partially surround, and do not completely or entirely surround, the movable bristles.

As noted, the movable bristle carrier may undergo a wide variety of motions. For example, the movable bristle carrier may undergo angular motion, linear motion, or curvilinear motion. The movement of the bristle carrier may be constant or periodic. Generally, the preferred motion for the movable bristle carrier is periodic linear motion or reciprocation.

The movable bristle carrier may be in a variety of forms and shapes. The preferred shape for the movable bristle carrier is oval, such as generally shown in the referenced figures, such as in FIGS. 2-5. It is generally preferred that the movable bristle carrier is elongated in shape, more preferably oval, and most preferably, have proportions according to a certain range of ratios of length to width dimensions. Most preferably, the movable bristle carrier is in the shape of an oval and has a length (as measured along a major axis of its oval shape) to width (as measured along a minor axis of its oval shape) of from about 4:1 to about 1.2:1. The width of the movable bristle carrier (again, as measured along a minor axis of its oval shape), approaches the width of the brush head, at that location along the brush head. For those embodiments of the present invention in which the bristle carrier is oval-shaped, and in which the bristle carrier moves in a reciprocating fashion, the carrier is oriented such that movement occurs generally parallel to the major axis of the oval shape. Preferably, the width of the movable bristle carrier is from about 50% to about 90% of the width of the brush head, and most preferably from about 60% to about 80%.

Figure 6:
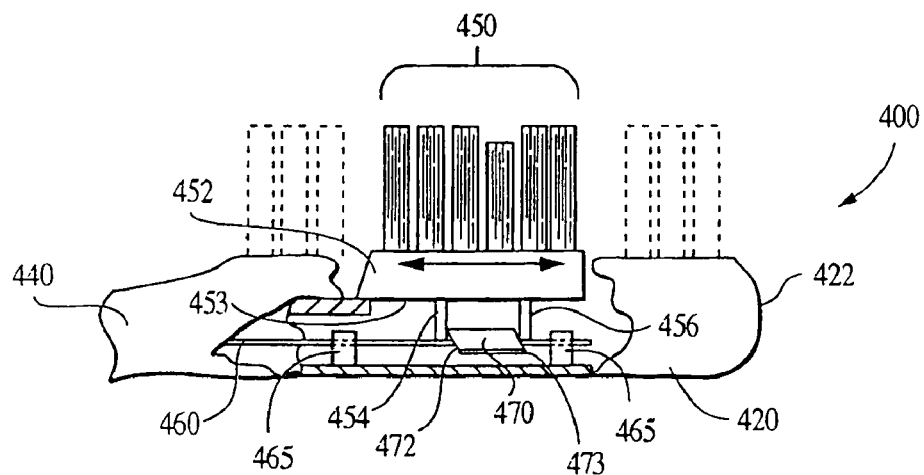
FIG. 6 is a partial cross-sectional view showing a brush head according to the present invention.

Referring to FIG. 6, another preferred embodiment of a head 420 for a toothbrush 400 will now be described. The head 420 includes an inner bristle carrier 452 that is slidingly mounted in slots defined along the head 420. The inner bristle carrier 452 supports and retains a plurality of movable bristles 450. The inner bristle carrier 452 is reciprocatingly driven in the same general longitudinal direction as the longitudinal axis of the head 420. The inner bristle carrier 452 and bristles 450 are preferably at least partially surrounded by an array of static bristles shown in FIG. 6 by dashed lines. The toothbrush 400 includes an electric motor (not shown) and a drive mechanism, the drive shaft of which is illustrated in FIG. 6 as shaft 460. A cam 470 engaged with the shaft 460 operatively interconnects the shaft 460 with inner bristle carrier 452. Optionally, the shaft 460 can be supported by shaft supports 465. The shaft supports 465 may include C or U shaped portions (not shown) that receive the shaft 460. Other means for retaining the shaft 460 in a support are known in the art. The cam 470 can comprise a shaped element or bead, with an appropriate eccentric configuration, placed or molded over and firmly secured to the shaft 460. In one arrangement, the cam 470 is cylindrically shaped with a pair of acutely angled surfaces 472, 473 which are inclined in the same direction and at the same angle of inclination, but which are disposed at opposite ends of the cam 470. In other words, the angled surfaces 472, 473 are the surfaces resulting from a diagonal slice through the cylinder of the cam 470. The direction of inclination and angle of inclination can be varied as desired to change the frequency and stroke of the inner bristle carrier 452. First and second cam followers 454, 456 are provided that are secured to or extend from the underside 453 of the bristle carrier 452. The cam followers 454, 456 are offset or spaced from each other so that cam 470 is disposed between the cam followers 454, 456 which straddle and/or capture the cam 470. The angled surfaces 472, 473 of the cam 470 slidingly engage the free ends of the cam followers 454, 456. As the shaft 460 rotates, the first acutely angled surface 472 of the cam 470 comes into contact with a surface of the first cam follower 454 and drives the cam follower, and therefore, the inner bristle carrier 452, away from the end 422 in a direction generally the same as the direction of the longitudinal axis of the head 420. The inner bristle carrier 452 is guided by the longitudinally extending slots. As the shaft 460 continues to rotate, the cam 470 disengages from the first cam follower 454. The second acutely angled second surface 473 of the cam 470 then comes into contact with a surface of the second cam follower 456 and drives the second cam follower 456, and therefore the inner bristle carrier 452, back toward the end 422 of the head 420.

Figure 7:
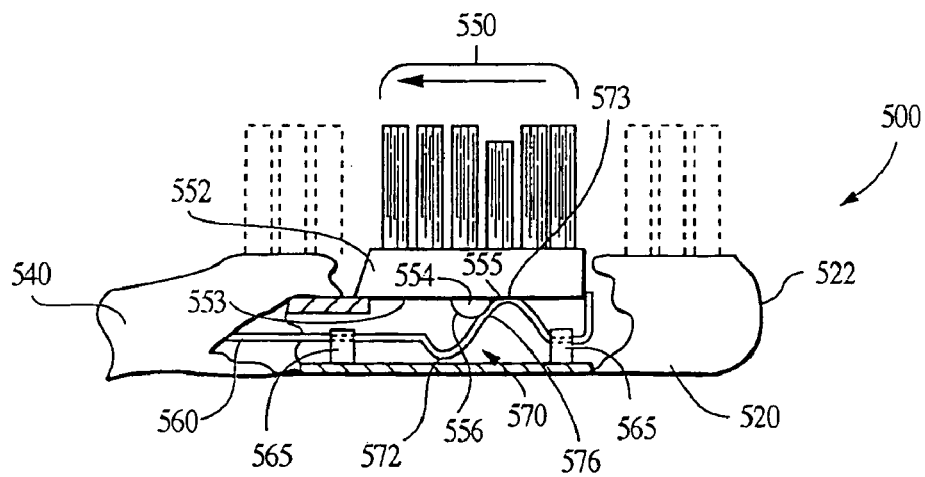
FIG. 7 is a partial cross-sectional view showing another brush head according to the present invention.
Figure 8:
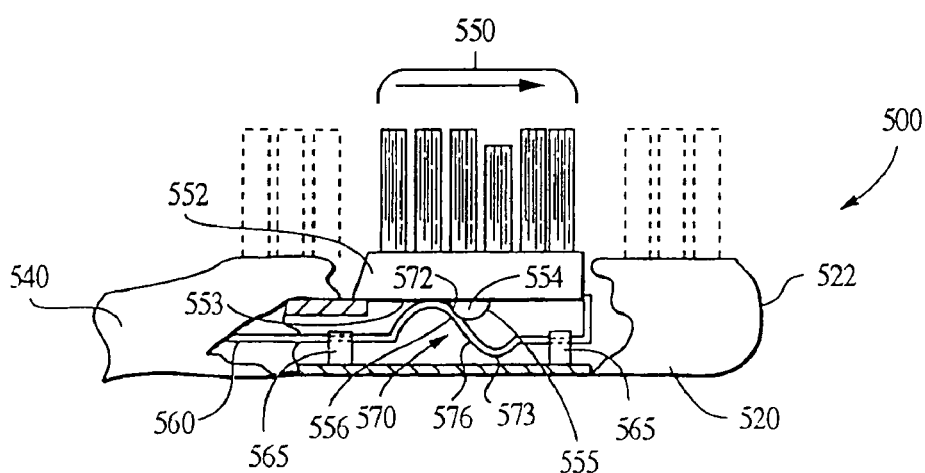
FIG. 8 is a partial cross-sectional view of yet another brush head according to the present invention.

Referring to FIGS. 7 and 8, another embodiment of a toothbrush head 520 suitable for use with an electric toothbrush 500 will now be described. The head 520 includes an inner bristle carrier 552 that is slidingly mounted in slots (not shown) defined in the head 520. The inner bristle carrier 552 supports and retains a plurality of bristles 550. The inner bristle carrier 552 is reciprocatingly driven in the same general longitudinal direction as the longitudinal axis of the head 520. The toothbrush 500 includes a motor (not shown) and a drive mechanism that includes a rotating drive shaft 560. The head 520 extends from a neck 540 and has a distal-most end 522. A cam 570 included on the shaft 560 operatively interconnects the shaft 560 with inner bristle carrier 552. Optionally, the shaft 560 can be supported by shaft supports 565. The shaft supports 565 may include C or U shaped portions (not shown) that receive the shaft 560. Other means for retaining the shaft 560 in a support are known in the art. The cam 570 is provided in the form of a plurality of bends 572, 573 in the shaft 560. The bends are sinusoidal or curvilinear in nature in that each bend has one or more adjacent arcuate portions. The bends each have an apex and the apexes are disposed on opposite sides of the shaft 560. A hemispherically-shaped cam follower 554 depends from a bottom surface 553 of the inner bristle carrier 552 and is disposed between the apexes of the cam 570. As the shaft 560 rotates, a surface 576 of the cam 570 comes into contact with a first surface 555 of the cam follower 554 and drives the cam follower 554, and therefore the inner bristle carrier 552, away from the end 522 in a longitudinal direction generally the same as the longitudinal axis of the head 520. As the shaft 560 continues to rotate, the cam surface 576 disengages from the first cam follower surface 555. As shown in FIG. 8, the cam surface 576 then comes into contact with a second surface 556 of the cam follower 554 and drives the cam follower 554, and therefore the inner bristle carrier 552, back toward the end 522. The motion of the bristle carrier 552 can be varied by changing the spacing between the apexes 572, 573 and/or the amplitude, shape, or height of the apexes 572, 573, length and inclination of the cam surface 576, and inclination of the surfaces 555, 556 of the cam follower 554.

Figure 9:
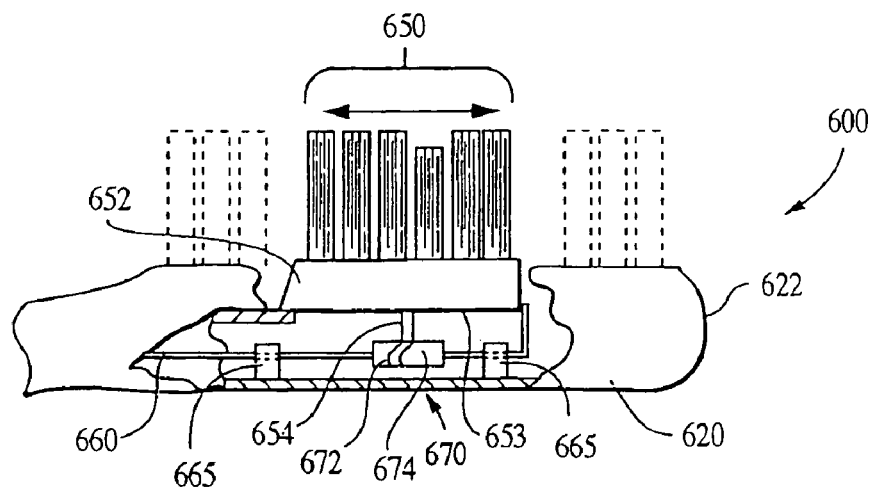
FIG. 9 is a partial cross-sectional view of another brush head according to the present invention.

Referring to FIG. 9, another embodiment of a toothbrush head 620 for an electric toothbrush 600 will now be described. The head 620 includes an inner bristle carrier 652 that is slidingly mounted in slots (not shown) defined in the head 620. The head 620 includes a distal end 622. The inner bristle carrier 652 supports and retains a plurality of bristles 650. The inner bristle carrier 652 is reciprocatingly driven in the same general longitudinal direction as the longitudinal axis of the head 620. The toothbrush 600 includes a motor (not shown) and a drive mechanism that includes a rotating drive shaft 660. A cam 670 included on the shaft 660 operatively interconnects the shaft 660 with the inner bristle carrier 652. Optionally, the shaft 660 can be supported by shaft supports 665. The shaft supports 665 may include C or U shaped portions (not shown) that receive the shaft 660. Other means for retaining the shaft 660 in a support are known in the art. The cam 670 is provided in the form of a cylindrically-shaped component 674 placed or molded over and firmly secured to the shaft 660.

Figure 10:
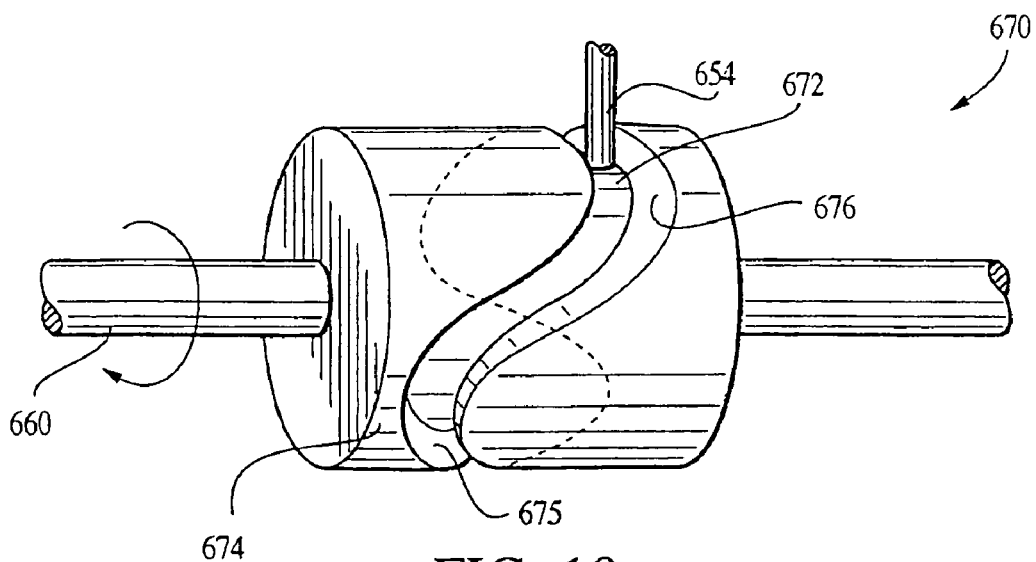
FIG. 10 is a perspective view of a cam assembly according to the present invention.

As shown in FIG. 10, the cam 670 includes a spiral or helical groove 672 defined along the outer surface of the cylindrically shaped component 674. The spiral or helical groove 672 preferably extends around the circumference of the component 674 and spirals about a longitudinal axis of the component 674 which may, for example, coincide with the longitudinal axis of the shaft 660. The stroke and frequency of the motion imparted to a cam follower 654 (shown in FIGS. 9 and 10) by the cam 670 can be varied by changing the shape and dimensions of the groove 672. For example, the groove 672 defined in the component 674 would provide one complete stroke of the inner bristle carrier 652 (i.e., one cycle away from and back toward the end of the head 622) for one revolution of the shaft 660.

Figure 11:
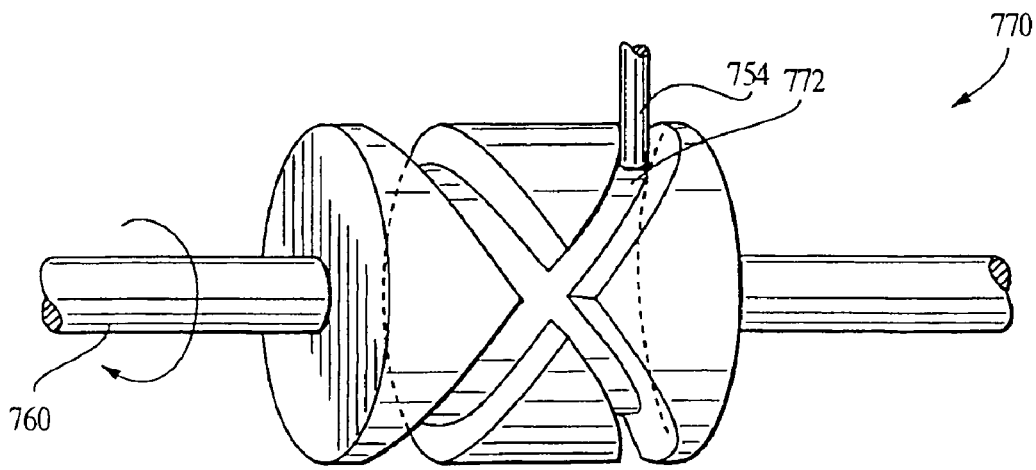
FIG. 11 is a perspective view of another cam arrangement according to the present invention.

FIG. 11 illustrates an alternate cam 770 having a helical groove 772 which is provided in the form of a figure eight. This would only provide one-half a stroke (i.e., only either translation toward or away from the end of the brush head) for one revolution of the shaft 760. A cam follower 754 is disposed in the groove 772 and is engaged to a movable bristle carrier.

Returning to FIGS. 9 and 10, a cam follower 654 depends from a bottom surface 653 of the inner bristle carrier 652. The cam follower 654 is slidingly received within the groove 672. As the shaft 660 rotates, a first surface 675 of the spiral groove 672, such as a side wall thereof, comes into contact with a first surface of the cam follower 654 and drives the cam follower 654 and therefore the inner bristle carrier 652, away from the end 622 of the brush head 620, in a longitudinal direction generally the same as the longitudinal axis of the head 620. As the shaft 660 continues to rotate, the cam follower 654 reaches an apex of the spiral groove 672 and the first surface 675 of the spiral groove 672 disengages from the cam follower 654. A second surface 676 of the groove 672, such as the opposite side wall of the groove 672, then comes into contact with the cam follower 654 and drives the cam follower 674, and therefore the inner bristle carrier 652, back toward the end 622 of the brush head 620.

The various reicprocating bristle carries described herein may also utilize a drive mechanism that provides a shaft that rotates. Furthermore, it will be appreciated that other motor and reciprocating or rotating shaft arrangements can be substituted. For example, U.S. Pat. Nos. 5,226,206; 5,524, 312; 5,383,242; 5,465,444; 5,504,959; 5,836,030; 4,845,795; 5,404,608; 5,359,747; and 5,617,601, the substances of which are incorporated herein by reference, disclose other motor and reciprocating shaft arrangements that might be suitable. In addition, the electric toothbrush of FIG. 9 might be provided with a replaceable head. A suitable arrangement which can be adapted to the sent invention is disclosed in U.S. application Ser. No. 09/850,662, filed May 7, 2001, now U.S. Pat. No. 6,836,917, the substance of which is incorporated herein by reference. Similarly, the drive mechanisms disclosed in U.S. applications Ser. No. 10/114,780 filed Apr. 3, 2002, now abandoned; and Ser. No. 10/128,018 filed Apr. 22, 2002, now abandoned both of which are herein incorporated by reference, are also contemplated for use in conjunction with the present invention.

Figure 12:
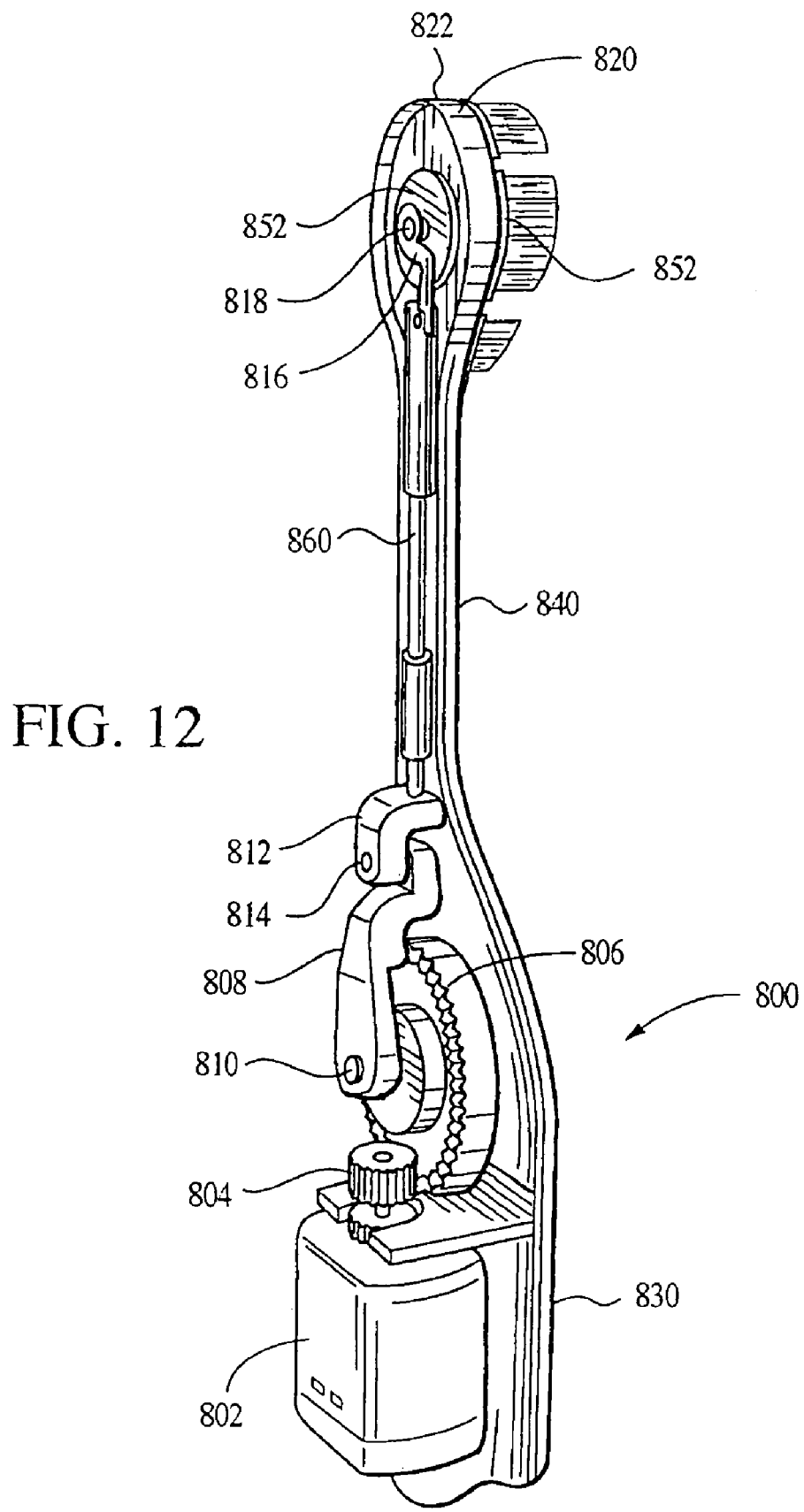
FIG. 12 is a perspective view showing a partial assembly of a toothbrush in accordance with the present invention.

Another preferred embodiment toothbrush using a reciprocating drive shaft is illustrated in FIG. 12. FIG. 12 illustrates an electric toothbrush 800 comprising a toothbrush head 820, a body or handle 830, and an elongated neck 840 extending therebetween. The drive train, which includes various shafts and gears that transmit motion from a motor to an inner bristle carrier 852 is similar to that described in U.S. Pat. No. 6,178,579, the substance of which is incorporated herein by reference. The handle 830 is hollow and includes a motor 802 and batteries (not shown) for powering the motor. In one embodiment of the invention the toothbrush comprises a power source of one battery. In another embodiment of the invention the toothbrush comprises a power source of two batteries. A rechargeable power source can be substituted for the batteries. The batteries can connect the motor via a wire, a metal strip, direct contact, and/or any combination thereof. The head 820 has a longitudinal axis extending therethrough. The longitudinal axis extends in the same general longitudinal direction as a longitudinal axis of the shaft 860. The inner bristle carrier 852 is disposed along the head 820, wherein the end 822 is at the distal-most point of the head 820. Although the inner bristle carrier 852 is preferably oval in shape, other shapes can be utilized. Further, while the inner bristle carrier 852 is disposed proximate the end 822 of the head 820, it will be appreciated that the carrier 852 can be disposed away from the end 822 and other features, such as static bristles, can be disposed around at least a portion of the perimeter of the inner bristle carrier 852. In this embodiment, the inner bristle carrier 852 only reciprocates and does not oscillate, or perform any other rotational or oscillatory motion.

A first gear 804 is operatively connected to and powered by the motor 802. A second gear 806 is operatively connected to the first gear 804. The rotational axis of the second gear 806 is approximately normal to the rotational axis of the first gear 804 such that the teeth of the first gear 804 mesh with teeth of the second gear 806, thus causing the second gear 806 to rotate as the first gear 804 rotates.

A first arm 808 is eccentrically and pivotably connected to the second gear 806 via a pin 810 or other fastening device. Due to the eccentric connection, the rotational motion of the second gear 806 is converted into a reciprocating motion of the first arm 808. A second arm 812 is pivotally connected to the first arm 808 via a pin 814 or other fastening device. The shaft 860 is secured, such as by a press fit, to the second arm 812. The shaft 860 is housed at least partially within the neck 840. The shaft 860 is also engaged with a third arm 816. The third arm 816 is connected at its terminal end to the inner bristle carrier 852 via a pin 818 or other fastening device. The terminal end of the third arm 816 is offset from the longitudinal axis of the shaft 860 so that it is pinned adjacent the outer periphery of the inner bristle carrier 852. This offset arrangement converts the reciprocating motion of the third arm 816 into a reciprocating motion of the inner bristle carrier 852, wherein the inner bristle carrier 852 reciprocates about an axis approximately parallel to the longitudinal axis of the shaft 860.

While various brush head embodiments of the present invention have been illustrated for simplicity with tufts or groups of bristles that extend in a direction substantially perpendicular to the longitudinal axis of the head from which they extend, it is contemplated that the bristles might be arranged differently to complement or further enhance the static bristles or the motion of the movable bristles. Some or all of the bristles might extend in a direction which forms an acute angle with a top surface of a bristle carrier, and may extend in a forward or rearward direction. In another embodiment, some of the bristles might extend outwardly away from the head, in another direction, again forming an acute angle with respect to the top surface of the bristle carrier. Elastomeric elements or massaging bristles or bristles of varying height might also be used, such as described in U.S. Pat. Nos. Des. 330,286, and Des. 434,563, the substances of which are incorporated herein by reference. Other preferred bristle arrangements suitable for use include those arrangements described in whole or part in U.S. Pat. Nos. 6,006,394; 4,081,876; 5,046,213; 5,335,389; 5,392,483; 5,446,940; 4,894,880; and International Publication No. WO99/23910; the substances of which are incorporated herein by reference.

The electric toothbrushes of the present invention can be provided with any combination of bristle or elastomeric tip types, dimensions, combinations, angles and arrangements. Tufts of bristles may alternate in height. By "tuft", herein, is meant a set of one or more bristles fastened to the brush at a common point. In one embodiment a plurality of tall tufts and a plurality of shorter tufts are disposed along the brush head. The difference in length between the tall tufts and the shorter tufts is between about 0.5 mm and about 2.5 mm in one embodiment and between about 1 mm and about 2 mm in other embodiments. The tall and short tufts of bristles can be provided with different characteristics. For example, the tall tufts of bristles may be relatively soft for gently cleaning and massaging gums of a user while shorter tufts of bristles may be somewhat firmer for interdental cleaning (or vice versa). This arrangement allows the longer (and typically softer) bristles to be pressed, bent and deflected against the gums of the user before the shorter (and typically firmer) bristles contact the teeth and gums of the user. Therefore, for example, soft bristles can be applied with more force while stiffer (and perhaps less comfortable) bristles are applied with less force.

In a particularly preferred embodiment, the present invention provides a bristle configuration in which the movable bristles, i.e. those supported by and secured to the movable bristle carrier, have a total bristle length that is less than the length of the static bristles that at least partially encircle or extend alongside the movable bristle carrier and bristles secured thereto. A further variation of this preferred bristle configuration features a movable bristle carrier that is slightly elevated above the outer surface of the head such that the distal ends of the movable bristles are approximately at the same height as the longer static bristles extending from the outer surface of the head. Generally, by utilizing movable bristles that have a relatively short length, the distance or stroke of the movable bristle carrier (when undergoing a reciprocating motion) is less than if longer bristles were used. A shorter stroke generally leads to decreased power requirements. This is beneficial since battery demands are then reduced, which may further promote manufacturability and commercialability of the resulting toothbrush. Moreover, by utilizing relatively short length bristles for the movable bristles, and longer bristles for the static bristles, a greater proportion of the brushing load is assumed by the static bristles. This generally further reduces power demands on the motor and drive mechanism of the toothbrush.

Bristle stiffness is also a parameter that has been found to affect brushing efficacy, power requirements of the preferred toothbrushes described herein, and overall performance of the toothbrush. This parameter is particularly important to consider with regard to bristle length or height. For instance, for certain applications, it is preferable to utilize relatively stiff and short bristles on the movable brush head component in order to reduce the amount of travel by the brush head component.

The bristles, collectively, have a bristle stiffness which can be characterized numerically by the following equation:

$$\text{Bristle Stiffness} = \frac{D^2 E}{X^2} * \frac{N^{30}}{1 \times 10^6}$$

Where;
D=bristle diameter, in inches
E=modulus of elasticity of the bristle material when wet, e.g. for nylon this is a constant, 460,000 psi
X=average bristle length across the head of the brush in inches
N=total number of bristles on brush head The bristle stiffness for brushes of the present invention, as determined by the above equation, preferably ranges from about 0.2 to about 0.8. However, the present invention electric toothbrushes may utilize bristles having stiffness values outside of this preferred range.

The initial stiffness calculation, $$\frac{D^2 E}{X^2}$$

for an individual bristle is a measure of the pressure produced by the minimum force required to deflect a single bristle according to *The Stiffness of Toothbrushes*, D. W. MacFarlane, Brit. Dent. Jour., Oct. 5, 1945, which is hereby incorporated herein by reference. Bristle stiffness is obtained by multiplying this single bristle stiffness value by the total number of bristles on the brush head. The factor $1 \times 10^6$ used in the denominator of the foregoing equation is an arbitrarily selected constant which reduces the overall bristle stiffness value to reasonably small numbers for ease of comparison. A detailed discussion of bristle stiffness is presented in U.S. Pat. No. 5,511,275 herein incorporated by reference.

It can be seen from the foregoing noted equation that generally, stiffness may be increased by increasing the number of bristles. Applying this equation to an individual tuft of bristles suggests that the stiffness of an individual tuft of bristles may be tailored by increasing or decreasing the number of bristles within that tuft, i.e. the tuft density. This technique can be used to readily provide a brush head bristle configuration having unique and selectively tailored brushing characteristics.

Another aspect of the preferred embodiment toothbrushes described herein relates to bristle or tuft density, and particularly, in combination with bristle size and material. Bristles for use herein can be made of any of the materials well known in the art. Suitable bristle materials herein include polyester and nylon, such as Dupont Tynex7 612 and Stylon7 612 from STP. Suitable types of nylon include, but are not limited to, Nylon 6/6, Nylon 10/10, and Nylon 12/12. The bristles are preferably of circular cross-section but can also be of other cross-sections including, but not limited to, rectangular, hexagonal and trilocular. Furthermore, the diameter and length of the bristles can vary within the usual dimensions known by a person skilled in the art. In preferred embodiments the bristles are of circular cross-section with a diameter of from 0.1 to 0.25 mm and length of from 7 to 15 mm, preferably 9 to 12 mm, with each tuft comprising from about 10 to about 50 bristles. The total number of bristles in the head portion of brushes of the present invention is preferably from about 1,200 to about 5,000, and even more preferably from about 1,600 to about 3,500. In such embodiments, each tuft is generally circular with a diameter of from about 1 to about 2 mm. It is also contemplated to utilize bristles and/or tufts of bristles having different diameters or spans together on a brush head.

Fastening of the bristle tufts to the brush head can be done using any of the methods known in the art, such as fusion, stapling and injection molding. Preferred processes herein are stapling and fusion. Each tuft has a base and a free end, the free ends of the tufts forming the working surface which is used to clean the teeth. As used herein, the "base" of the tuft is that part of the tuft at which it meets the face of the brush head or movable bristle carrier. It will be understood that a portion of the tuft extends below the base into the brush head or carrier, for the purpose of anchoring the tuft into the head or carrier. It is preferred for the head to comprise pre-molded tuft holes for the purpose of accommodating that portion of the tuft in this way. The tuft holes can be of any section including square and rectangular but are preferably circular. Their depth and diameter will be chosen by one ordinarily skilled in the art to suit the tufts to be inserted therein. Bristles inserted into a common tuft hole are considered to be fastened at a common point and to be part of the same tuft.

The length of the brush head is measured along the longitudinal axis of the toothbrush and generally from the distal end of the brush head to a location on the head just touching the tuft or row of tufts nearest the handle at the points of their base closest to the handle. Generally this brush head length is in the range from about 15 to about 35 mm, and preferably from about 20 to about 30 mm.

The length of the entire toothbrush is measured along the longitudinal axis of the toothbrush and generally from the distal end of the toothbrush head to the proximal end of the toothbrush handle, including the end cap. Generally this toothbrush length is greater than about 10 cm, about 12 cm, about 14 cm, about 16 cm, about 18 cm, and/or less than about 20 cm, about 22 cm, about 24 cm, about 26 cm.

It is most preferred that the bristle or tuft density on the movable bristle carrier is higher than the bristle density of the groups or regions of static bristles.

Figures 14, 15:
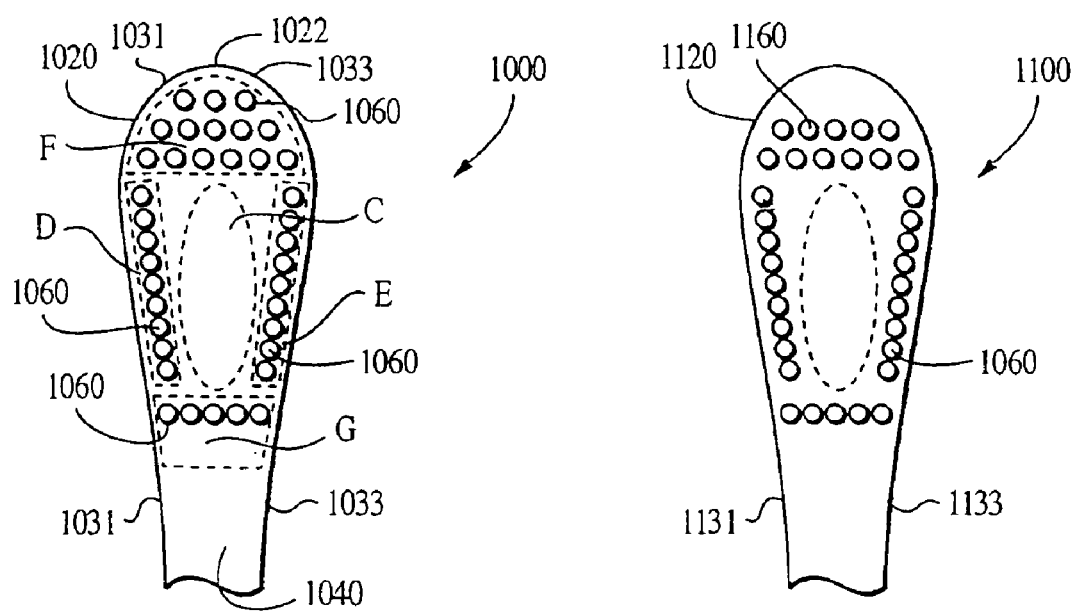
FIG. 14 is another bottom view of a toothbrush head showing a configuration of bristle arrangements and illustrates a manner of designating locations of certain bristles, according to the present invention.
FIG. 15 is another bottom view of a toothbrush head showing a configuration of bristle arrangements according to the present invention.

The present invention also provides several particularly preferred configurations of static bristles. The preferred configurations utilize a specific number of rows in designated regions of the brush head. These preferred configurations have been found to provide reduced load and wear on bristles that are disposed within the interior of the brush head, and particularly, the bristles that are supported on and by a movable bristle carrier. FIG. 14 illustrates a preferred configuration for a group of static bristles disposed on a brush head 1020 of a toothbrush 1000. In this particular configuration, at least a single row of bristles encircle or substantially encircle the interior region of the brush head, i.e. the location in which the movable brush head is disposed. Specifically, the various preferred configurations for the static bristles 1060 may be conveniently described by referring to various regions of the brush head as sectors, and describing the preferred arrangements of static bristles in each of those sectors. FIG. 14 illustrates a brush head 1020 having a centrally located sector C (within which a movable bristle carrier resides), that is surrounded by sectors D, E, F, and G. Sectors D and E are defined along the lateral and opposite sides of the brush head. Specifically, sector D is located between a first side 1031 of the brush head and sector C. Sector E is located between a second side 1033 of the brush head and sector C. Sector F is located between the first and second sides 1031 and 1033 of the brush head 1020, and a distal-most tip or end 1022 of the brush head 1020 and sector C. Sector G is defined between the first and second sides 1031 and 1033 of the brush head 1020, and the sector C and a neck 1040. Each sector in which static bristles may be located, may contain a certain number of rows of static bristles as follows. Before addressing the number of rows each sector preferably contains, it is instructive to define what is meant by a "row" of static bristles. A row of bristles is defined herein as an array or grouping of bristles that extends generally along a line or in a certain direction. Rows in sector D preferably extend in a direction that is generally parallel with the side 1031. Similarly, rows in sector E preferably extend in a direction that is generally parallel with the side 1033. Rows in sector F may extend in several fashions as follows. Rows in sector F may extend along an arc or other curved line generally following the curvature of sides 1031 and 1033 as the sides approach the distal end 1022 of the brush head 1020. Alternatively, rows in sector F may extend in a direction that is generally perpendicular to the longitudinal axis of the brush head 1020 and the neck 1040. This latter preferred configuration of rows is depicted in FIG. 14. Rows in sector G may extend along an arc or other curved line; such as extending along a line following the outer periphery of sector C. Alternatively, rows in sector G may extend in a direction that is generally perpendicular to the longitudinal axis of the brush head 1020 and the neck 1040. This latter preferred configuration of rows in sector G is depicted in FIG. 14, and such rows are preferably parallel to the rows in sector F.

The preferred number of rows of static bristles in sectors D, E, F, and G ranges from 0 to 4 or more. However, certain preferred combinations of rows are particularly preferred in accordance with the present invention. These particularly preferred combinations are set forth in Table 1:

TABLE 1

Preferred Configurations for Rows of Static Bristles

| Bristle Configuration Identifier | Number of Rows in Sector | | | |
|---|---|---|---|---|
| | D | E | F | G |
| a. | 1 | 1 | 1-3 | 1 |
| b. | 1 | 1 | 1-3 | 2 |
| c. | 2 | 2 | 1-3 | 1 |
| d. | 2 | 2 | 1-3 | 2 |
| e. | 0 | 0 | 1-3 | 1 |
| f. | 0 | 0 | 1-3 | 2 |
| g. | 1 | 1 | 0 | 0 |
| h. | 2 | 2 | 0 | 0 |

FIG. 13, as previously noted, illustrates a preferred configuration for the static and movable bristles. In this configuration, rows of static bristles are located along opposing sides of the movable bristle carrier. Within each row are groups or tufts of bristles. Preferably, the number of rows of bristles along each side of the bristle carrier ranges from 1 to 6. Most preferably, the number of rows on each side of the movable bristle carrier is either 1 or 2-6.

FIG. 15 illustrates one of the preferred static bristle configurations noted in Table 1 (bristle configuration identifier a). Specifically, FIG. 15 depicts a brush head 1120 of a toothbrush 1100 having a plurality of static bristles 1160 arranged in a predetermined number and combination of rows. It will be appreciated that although the rows depicted in FIG. 15 are shown as generally straight or linear, particularly in sectors F and G, the rows may follow the shape or curvature of the outer periphery of the brush head 1120 such as extending along a portion of the sides 1131 and 1133.

Within each sector of tufts, the distance between the bases of neighboring tufts is less than 1.3 mm, preferably from 0.6 to 1.2 mm, and more preferably from 0.8 to 1.1 mm. Distances between the bases of the tufts, as referred to herein are measured from tuft edge to tuft edge along a straight line drawn between tuft centers along the bristle-bearing face. Distances between the free ends of the tufts, as referred to herein, are measured from tuft edge to tuft edge along a straight line drawn between tuft centers, parallel to the bristle-bearing surface, from the free end of the shorter tuft. Unless specifically defined otherwise, distances between tufts refer to distances between neighboring tufts. By "neighboring tuft" is meant the closest nearby tuft.

The distance between the bases of neighboring tufts in adjacent groups, that is, measured across the gap between groups, is in the range from about 1.3 mm to about 5 mm, preferably from about 1.5 to about 3.5 mm, more preferably from about 1.7 to about 3 mm. There can be some variation across individual pairs of tufts but all pairs, where the members of each pair are in different groups will be at least 1.3 mm apart at their bases.

By having a relatively large distance between tufts in adjacent groups, the groups of tufts are able to operate independently of each other. That is, tufts from one group do not substantially obstruct tufts from an adjacent group. This allows tufts on the margins of the groups, in particular, to penetrate better into the interproximal gaps and other crevices. Nevertheless, a relatively high, overall density of tufts on the brush head is maintained by the relatively small distance between tufts within groups. This, in particular, provides for good bristle coverage on individual tooth surfaces.

Additional aspects and parameters of bristles and tufts are described in U.S. Pat. No. 6,314,605 herein incorporated by reference.

Figure 16:
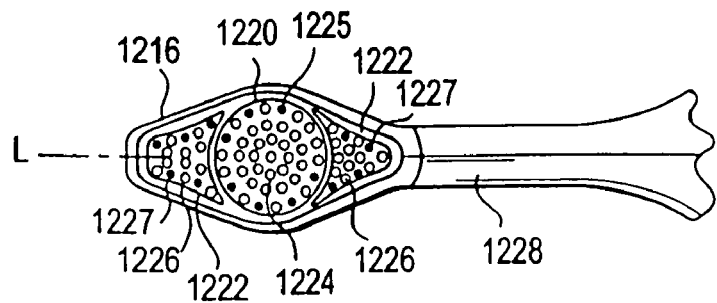
FIG. 16 is a bottom view of a brush head according to the present invention.
Figure 17:
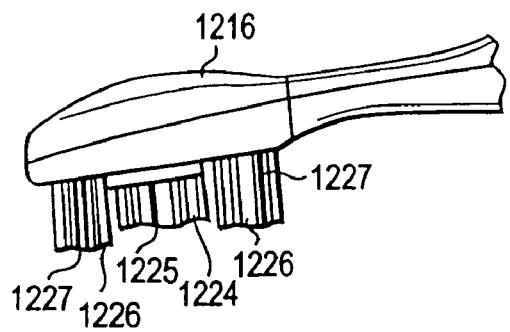
FIG. 17 is a side view of the brush head shown in FIG. 16.

Another embodiment of the present invention is shown in FIGS. 16 and 17, which utilizes one or more elastomeric elements. The head of an electric toothbrush as described herein is illustrated. The remaining portion of the brush, including the handle, motor, etc. is the same as described for any of the previously described embodiments. As shown in FIG. 16, a head 1216 includes a longitudinal axis L, a circular or moving portion or brush head 1220 and a static portion or region 1222. The head 1216 is located adjacent a first end 1228 of an elongated body portion. The static portion or portions 1222 is located on opposite sides of the moving portion 1220. The moving portion 1220 is located at the center of the brush head 1216. The circular portion 1220 rotates, swivels, oscillates or reciprocates about an axis approximately normal to the longitudinal axis L of the brush head. The circular portion 1220 may rotate 360 degrees or partially rotate or oscillate or reciprocate in a back and forth manner.

The moving portion 1220 includes bristles 1224 and elastomeric elements 1225. The static portion 1222 includes bristles 1226 and elastomeric elements 1227. The elastomeric elements 1225, 1227 massage the gums while the user simultaneously brushes his or her teeth. The elastomeric elements 1225, 1227 can be made from a rubber, soft plastic or similar material. The elastomeric elements are preferably formed from an elastomeric material. The elastomeric elements 1225, 1227 extend essentially perpendicularly from the head 1216 as measured along the longitudinal axis L. In the preferred embodiment the elastomeric elements 1225, 1227 are located around the perimeter of the circular portion 1220 and the static portion 1222, however it is to be understood that the elastomeric elements can be located anywhere among the bristles of the moving portion 1220 and the static portion 1222. The length of the elastomeric elements 1225, 1227 is approximately the same length as the bristles 1224, 1226. The elastomeric elements 1225, 1227 may extend slightly above, slightly below or to the same height as the bristles 1224, 1226.

Figure 18:
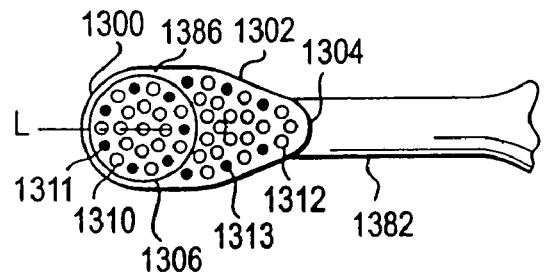
FIG. 18 is a bottom view of another brush head according to the present invention.
Figure 19:
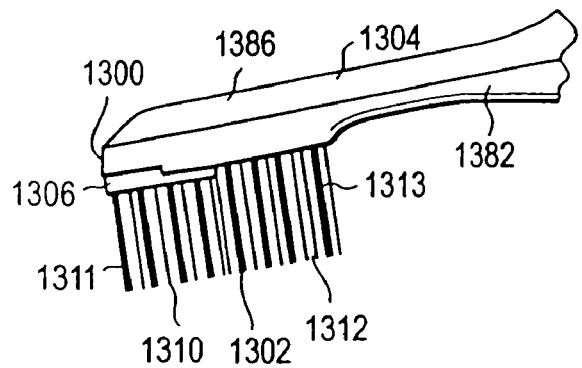
FIG. 19 is a side view of the brush head shown in FIG. 18.

In a further preferred embodiment of the electric toothbrush having elastomeric elements as shown in FIGS. 18 and 19, a head 1386 includes a longitudinal axis L, a circular or moving portion or brush head 1306, a static portion of brush head 1302, a first end 1304 and a second end 1300. The first end 1304 is located adjacent to the first end 1382 of the elongated body. The second end 1300 is located opposite the first end 1304. The moving portion 1306 is preferably located at the second end 1300 of the brush head 1386. The static portion 1302 is preferably located at the first end 1304 of the brush head 1386 adjacent to the moving portion 1306. However, it is to be appreciated that the moving portion 1306 and the static portion 1302 can be arranged in different orientations. The moving portion 1306 can rotate, swivel, oscillate or reciprocate about an axis approximately normal to the longitudinal axis L of the brush head 1386.

The moving portion 1306 includes bristles 1310 and elastomeric elements 1311. The static portion 1302 includes bristles 1312 and elastomeric elements 1313. The elastomeric elements 1311, 1313 massage the gums while the user brushes his or her teeth. The elastomeric elements 1311, 1313 can be made from a rubber, soft plastic or similar material. The elastomeric elements are preferably formed from an elastomeric material. The elastomeric elements 1311, 1313 extend essentially perpendicularly from the head 1386 as measured along the longitudinal axis L. In the preferred embodiment the elastomeric elements 1311, 1313 are located around the perimeter of the moving portion 1306 and the static portion 1302, however it is to be understood that the elastomeric elements can be located anywhere among the bristles of the moving portion 1306 and the static portion 1302. The length of the elastomeric elements 1311, 1313 is approximately the same length as the bristles 1310, 1312. The elastomeric elements 1311, 1313 may extend slightly above, slightly below or to the same height as the bristles 1310, 1312.

The present invention is also based upon a unique design for a unitary body or housing for an electric toothbrush that incorporates an integral neck and brush head assembly. The one-piece body or housing greatly simplifies assembly of the toothbrush and reduces manufacturing costs associated with the brush. The present invention also provides a novel modular design for the brush head that enables a wide array of bristle sets to be used in conjunction with the toothbrush.

Figure 20:
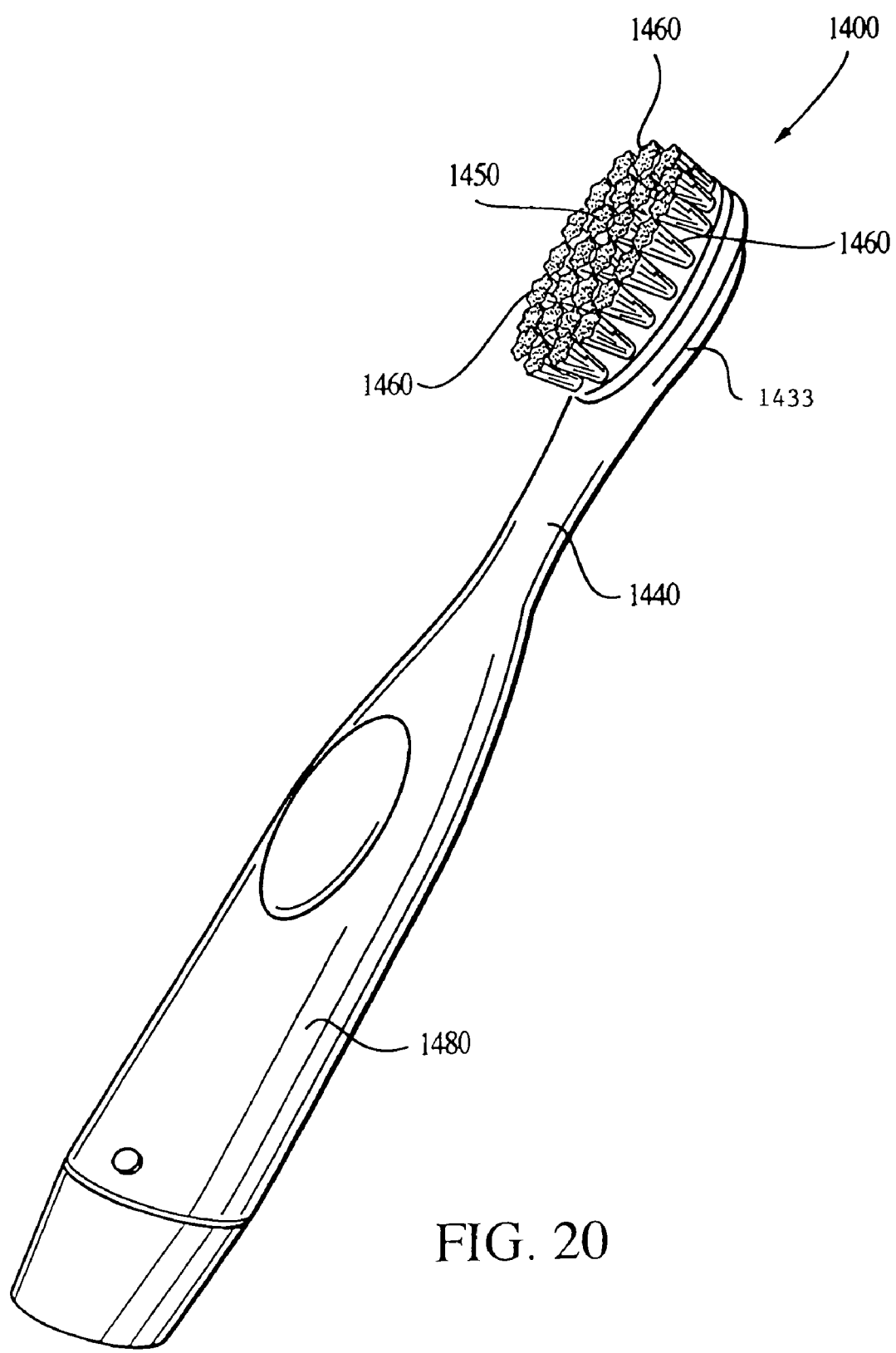
FIG. 20 is a perspective view of another toothbrush in accordance with the present invention.

Referring to FIG. 20, one embodiment of the inventive toothbrush 1400 is illustrated. The toothbrush 1400 comprises a body 1480, a head 1433 and an intermediate portion or neck 1440 extending between, and integrally formed with, the body 1480 and the head 1433. Movably retained on the head 1433 are a collection of bristles 1450 which are supported on a movable bristle carrier described in greater detail herein. Also disposed on the head 1433 are a collection of static bristles 1460. Preferably, the static bristles 1460 extend around the periphery of the head 1433. The static bristles 1460 are supported and retained by the head of the toothbrush 1433 are described and illustrated in greater detail herein.

Figure 21:
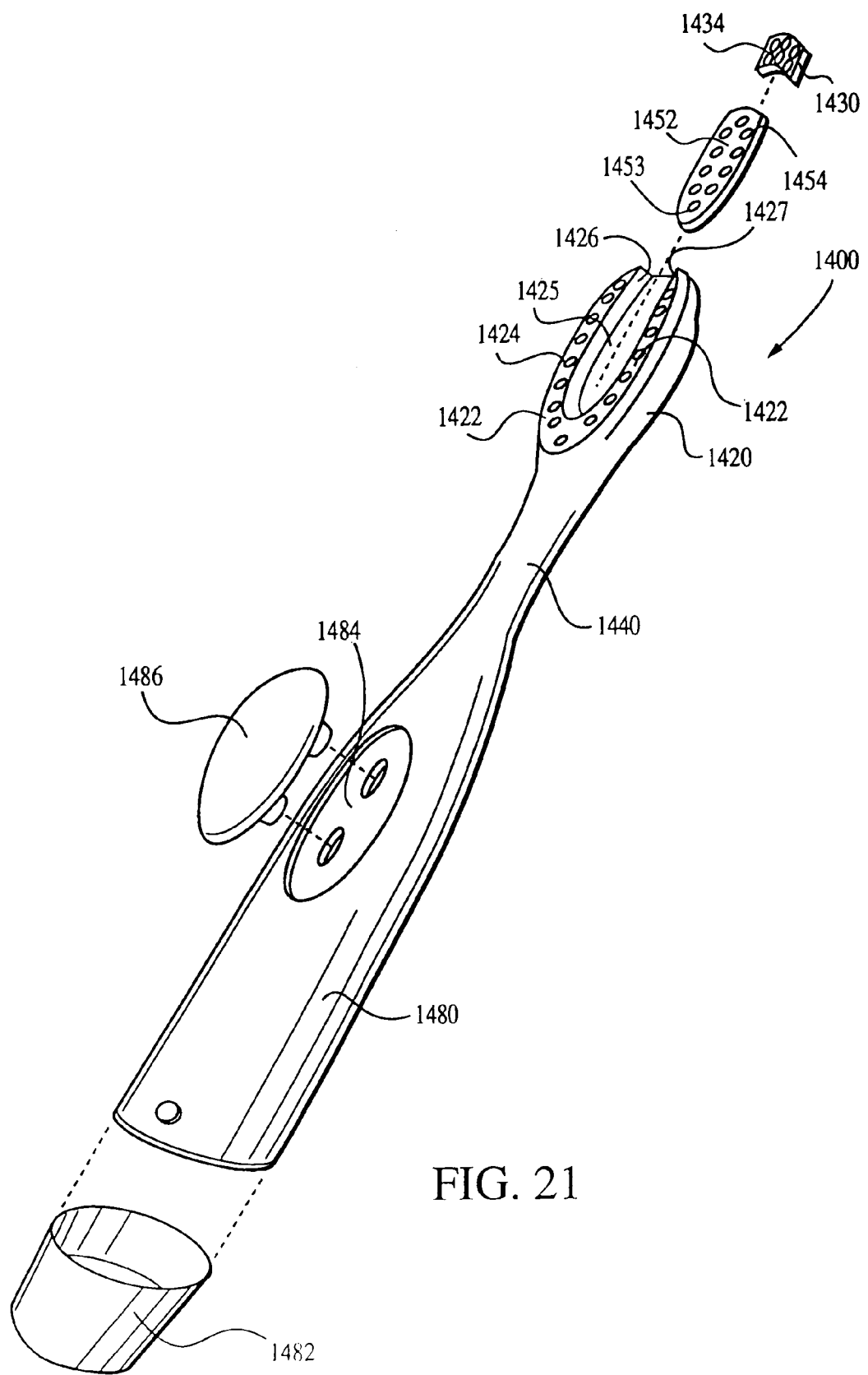
FIG. 21 is a partial exploded perspective view of the toothbrush illustrated in FIG. 20, illustrating certain components and their assembly.

FIG. 21 is a partial exploded view of an embodiment of the toothbrush 1400 shown in FIG. 20. FIG. 21 illustrates an assembly and configuration of components utilized in the toothbrush 1400 wherein the separate static and movable bristle carriers independently engage the receiving member to form the head of the toothbrush. The static and movable bristle carriers can engage the receiving member independently in either the same channel or within separate channels. FIG. 21 illustrates the toothbrush 1400 which further comprises an end cap or base 1482 which snaps on or is otherwise releasably secured to the end of the body 1480. The end cap or base 1482 may be provided in a variety of different shapes and configurations including, but not limited to, round, oval, square, and/or rectangular. The body 1480 also includes a region adapted for retaining a switch or other actuator assembly 1486 for controlling operation of a motor, battery, and drive train or mechanism (not shown) preferably disposed in the body 1480 of the toothbrush 1400. This switch region is illustrated in FIG. 21 as region 1484. The switch or actuator 1486 is received and retained at region 1484. The body 1480 provides a hollow interior cavity or chamber in which is disposed the motor and drive mechanism. Upon operation, the drive mechanism preferably provides a drive shaft that reciprocates in a direction generally parallel to the longitudinal axis of the toothbrush 1400. Referring to the receiving member 1420 of the toothbrush 1400 in FIG. 21, it will be noted that the receiving member is shown without any bristles 1450,1460 (as shown in FIG. 20). This is to more clearly illustrate assembly of the toothbrush 1400. It can be seen that one face of the receiving member 1420 is configured so as to include a generally flat surface 1422 which defines a plurality of mounting locations or apertures 1424 for the static bristles 1460. Preferably this flat region 1422 and its plurality of apertures 1424 extend about the outer periphery of the receiving member 1420 as shown in FIG. 21. Most preferably, this flat region 22 extends in a U-shape as shown in FIG. 21. Defined along the interior or medial region of the receiving member 1420 is a receiving surface or channel 1425 generally extending between two inwardly facing receiving surfaces or channels 1426 and 1427. These channels are generally in pairs and are defined by surfaces 1425, 1426, and 1427 are generally sized so as to receive components 1452 and 1430 as follows.

The embodiment of the toothbrush 1400 comprises a movable bristle carrier 1452 which, upon engagement with the receiving member, is retained along the receiving member 1420 and preferably within a pair of channel defined by surfaces 1425, 1426, and 1427 of the receiving member. Movable bristle carriers 1452 defines a plurality of apertures 1454 as shown in FIG. 21. The bristle carriers 1452 also defines an aperture 1453 that is sized and adapted to receive a pin or other member for engagement with the drive mechanism (not shown) disposed in the body 1480 and neck 1440 of the toothbrush 1400. The present invention includes other engagements between the movable bristle carriers 1452 and a drive shaft, such as but not limited to, a snap type engagement. The toothbrush 1400 further comprises a static carrier, such as brush head tip 1430 which, after assembly of the movable bristle carriers 1452 on the head 1433, may also be received and secured along the head 1433. The brush head tip 1430 also defines a plurality of apertures 1434 adapted for retaining a plurality of static bristles 1460 as shown in FIG. 20.

Figure 22:
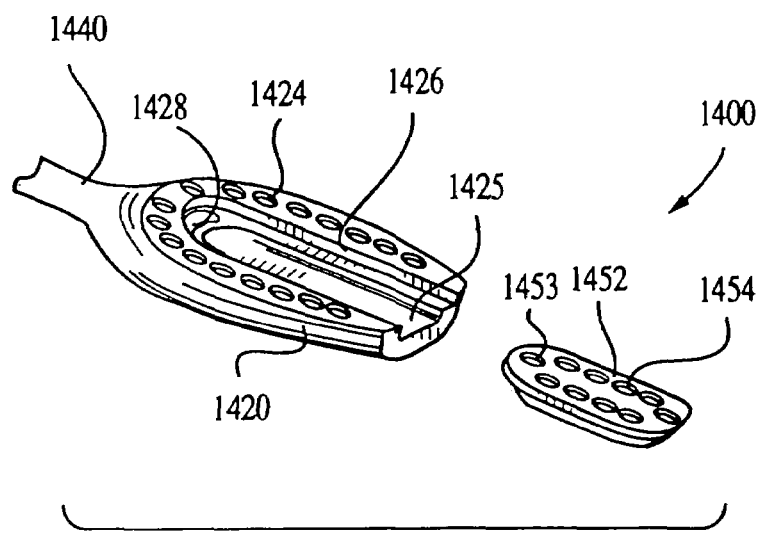
FIG. 22 is a partial exploded perspective view illustrating the assembly of a toothbrush head of the brush shown in FIGS. 21 and 22.
Figure 23:
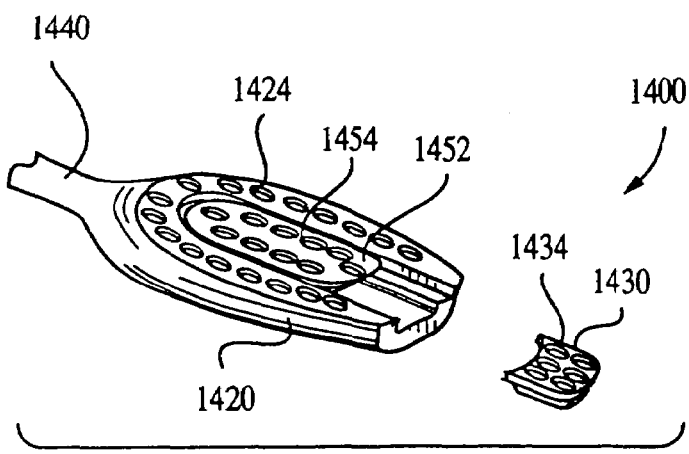
FIG. 23 is another partial exploded perspective view of the toothbrush head of FIG. 22 illustrating further assembly of components therein.
Figure 24:
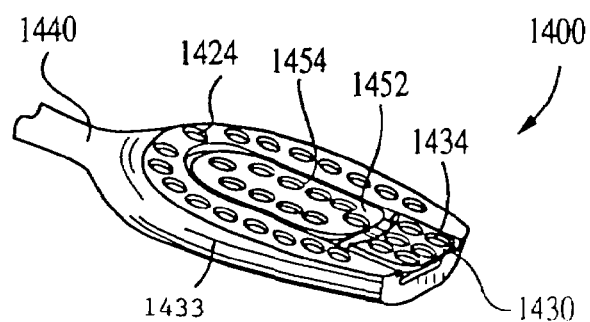
FIG. 24 is another partial exploded perspective view of the toothbrush head of FIGS. 22 and 23, again illustrating further assembly of components therein.

FIGS. 22 to 24 illustrate a sequence of assembly of the movable bristle carriers 1452 and the brush head tip 1430 with the receiving member 1420 to form the head 1433 of the embodiment of the toothbrush 1400. Specifically, FIG. 22 illustrates the receiving member 1420 and neck 1440 of the embodiment of the toothbrush 1400. The receiving member 1420 is oriented to receive the movable bristle carriers 1452. Specifically, the bristle carriers 1452 can preferably slidingly engage the toothbrush head within the channel defined by the surfaces 1425, 1426, and 1427 in the receiving member 1420. The head of the toothbrush 1433 includes a passage 1428. The passage 1428 provides access between the head 1433 of the toothbrush and the interior of the body 1480 and neck 1440. This passage 1428 can be adapted to enclose and retain a shaft or other component of a drive mechanism. The distal end of the drive shaft (not shown) can be secured to the movable bristle carriers 1452 such as by attachment at aperture 1453 of the carriers 1452. Accordingly, the bristle carriers 1452 can be oriented within the pairs of channels defined on the receiving member 1420 such that the aperture 1453 is proximate the passage 1428. As previously noted, a snap-fit connection may be utilized between the bristle carriers 1452 and the distal end of the drive shaft.

FIG. 23 illustrates the movable bristle carriers 1452 slidingly engaged within the head 1433 of the embodiment of the brush 1400. After engagement of the movable bristle carriers 1452 to the receiving member 1420, the brush head tip 1430 may be secured along the distal end of the receiving member 1420. The brush head tip 1430 preferably is also slidingly engaged within the receiving member 1420, and specifically within the channel defined by the surfaces 1425, 1426, and 1427. One or more retaining grooves or channels are preferably defined along the outer surfaces of either the tip 1430 or the channel defined by the surfaces 1425, 1426, and 1427 within which outwardly extending projections defined on an opposing surface, reside to secure the tip 1430 within the receiving member 1420. A wide array of channel configurations may be utilized in accordance with the present invention. Although a channel and corresponding channel components are used to assist in retaining the movable bristle carriers to the brush head, it is contemplated that other retaining assemblies or configurations may be utilized. As previously noted, the present invention toothbrushes are not limited to a particular motion or direction of motion for the movable bristle carriers.

FIG. 24 illustrates final assembly of the tip 1430 along the distal end of the receiving member 1420. It will be appreciated that the various components noted in these figures, would include the bristles 1450,1460. The bristles have been omitted from these figures to more clearly illustrate assembly of the primary components of the toothbrush 1400 and specifically along the receiving member 1420 and the toothbrush head 1433. It will be further appreciated that the brush head tip may be formed in a variety of shapes and configurations. It may in some instances, be preferred to provide a brush head tip having an arcuate or U shape. Or, the tip may be formed so as to constitute a relatively large portion of the brush head. Or, the arcuate or U shape may substantially surround the movable bristle carriers.

Figure 21A:
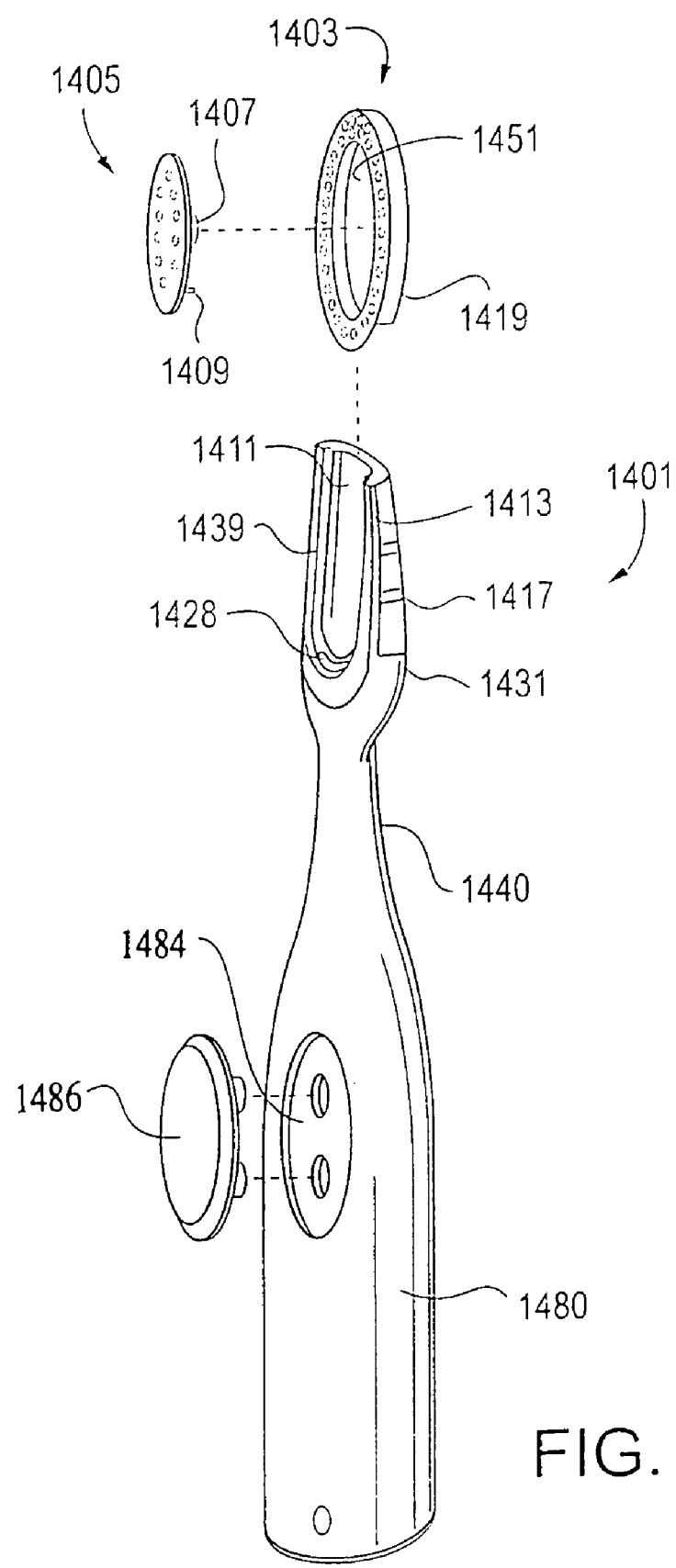
FIG. 21a is a partial exploded perspective view of an embodiment of the toothbrush, made according to the present invention, illustrating certain components and their assembly.
Figure 22A:
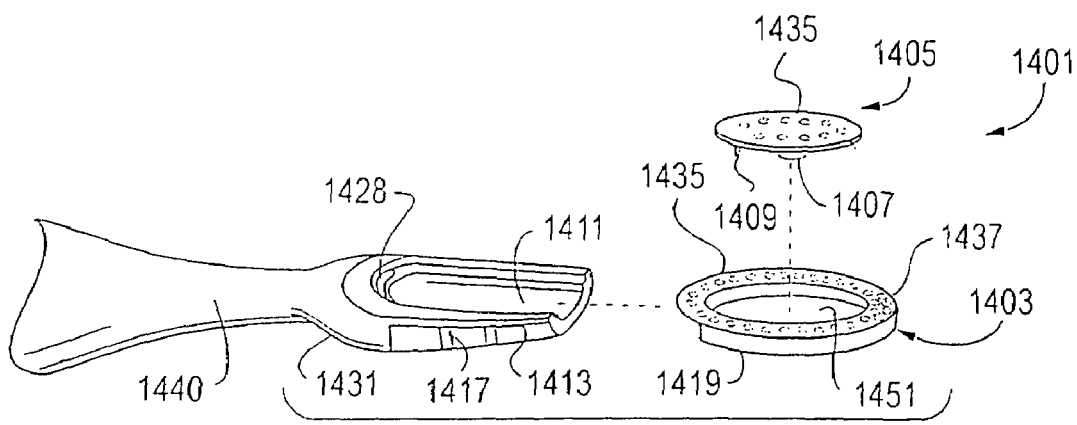
FIG. 22a is a partial exploded perspective view illustrating the assembly of another embodiment of the toothbrush head.

FIG. 21a is a partially exploded view of another embodiment of the toothbrush made according to the present invention. FIG. 21a illustrates an assembly and configuration of components utilized in the embodiment of the toothbrush 1401. It can be seen that the head of the toothbrush comprises a receiving member, and bristle carriers. The plurality of bristle carriers are shown without bristles to more clearly illustrate the assembly of the toothbrush 1401. FIG. 22a shows that one face of the bristle carriers is configured so as to include a generally flat surface 1435 which defines a plurality of mounting locations or apertures 1437 for the bristles to be inserted. The receiving member 1431 as shown in FIGS. 21a-24a of the toothbrush is an extension from the neck, which provides surfaces that the bristle carriers can engage.

Figure 24A:
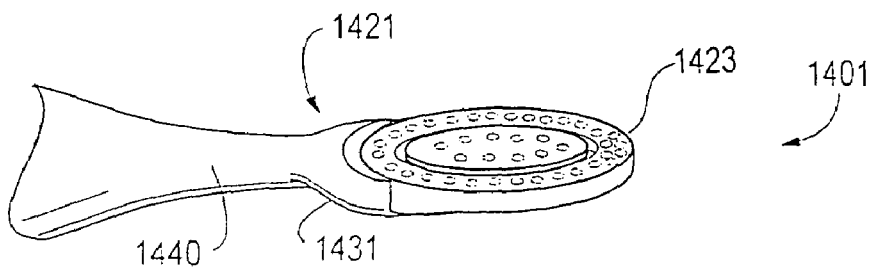
FIG. 24a is another partial exploded perspective view of the toothbrush head of FIGS. 22a and 23a, again illustrating further assembly of components therein.
Figure 25:
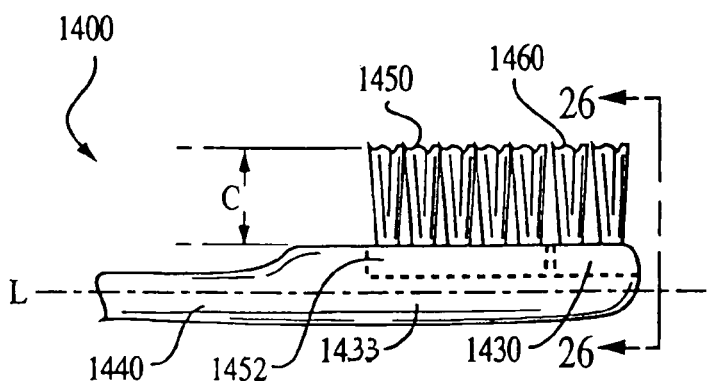
FIG. 25 is a partial side elevational view of the toothbrush head of the brush illustrating one possible bristle configuration in accordance with the present invention.
Figure 26:
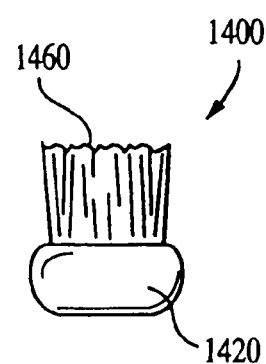
FIG. 26 is an end view of the toothbrush head taken along line 26-26 in FIG. 25.
Figure 25A:
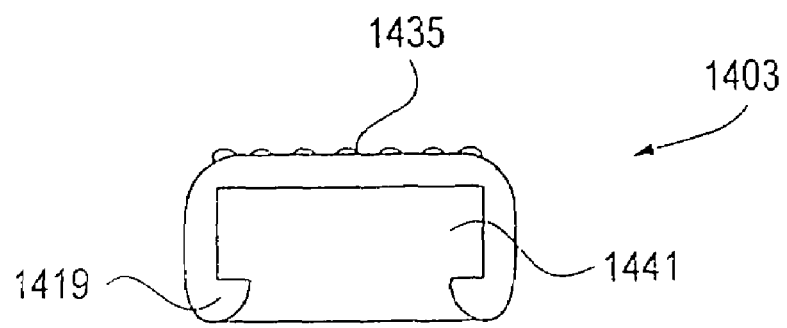
FIG. 25a is an end view of the static bristle carrier 1403.
Figure 26A:
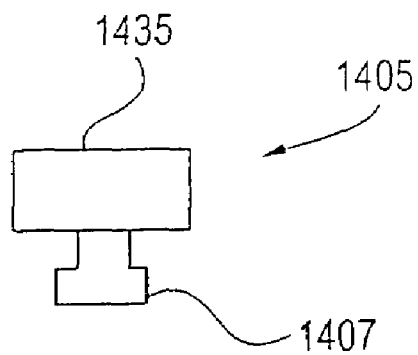
FIG. 26a is an end view of the movable bristle carrier 1405.

In this embodiment of the toothbrush the head comprises the receiving member 1431 the movable bristle carrier 1405 and the static bristle carrier 1403. The receiving member 1431 is configured so as to include a generally flat surface 1439 shown in FIG. 21a. This generally flat region preferably contains guiding elements, which engage and retain the bristle carriers. Examples of guiding elements include, but are not limited to pairs of channels 1411 and 1413 as shown in FIGS. 21a and 27a, and rails 1407 and 1419 as shown in FIGS. 25a and 26a. The static bristle carriers and the movable bristle carriers can independently, slidingly engage the pairs of channels 1411 and 1413 with rails 1407 and 1419 respectively. While the static and movable bristle carriers are illustrated herein as independently engaging separate channels it is contemplated that the static and movable bristle carriers can independently engage the same channel(a). The channels are defined by the surface of the receiving member 1431 and are generally sized so as to receive rails 1407 and 1419, as shown in FIGS. 22a to 24a. Also, in another embodiment of the toothbrush, the brush head comprises areas to snap (not shown) or otherwise removably attach the movable 1405 and static bristle carriers 1403.

The embodiment of the toothbrush 1401 comprises one or more movable bristle carrier(s) 1405 which engage the receiving member 1431, preferably within a pair of channels 1411 defined by the surfaces of the receiving member. The surfaces of the movable bristle carriers can serve as a guide to direct and engage the movable bristle carriers within the channels defined by the surfaces of the receiving member 1411. Preferably these guides are rails 1407 sized to fit the channels 1411. The guide can be any shape sized to fit the channels defined by the surfaces of the receiving member, including but not limited to I-shaped, T-shaped, C-shaped, and/or U-shaped. The guide shown in FIG. 26a is a T-shaped rail 1407. Preferably, the movable bristles are substantially encircled by static bristles disposed on the static bristle carrier 1403. To form this preferred toothbrush head the one or more static bristle carrier(s) 1405 engage the receiving member, preferably within a pair of channels 1413. The surfaces of the static bristle carriers can comprise guides such as rails 1419 sized to fit the pair of channels 1413. Rails 1419 direct and engage the static bristle carriers within the pair of channels 1413 to form the head of the toothbrush. Additionally, the engagement of the static and/or movable bristle carriers to the receiving member to form the head of the toothbrush can be releasably removable so that the bristle carriers can be replaced or exchanged for new or different bristle carriers.

Figure 23A:
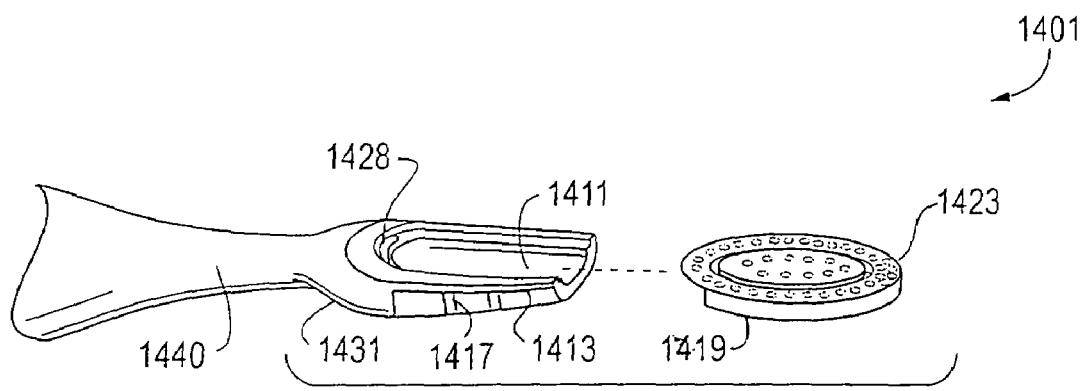
FIG. 23a is another partial exploded perspective view of the toothbrush head of FIG. 22a illustrating further assembly of components therein.

In the embodiment shown in FIGS. 21a-27a the head of the toothbrush can be formed by the bristle carriers engaging the receiving member within pairs of channels such as pair 1411 and pair 1413 defined by the surfaces of the receiving member 1431 which extends from the toothbrush neck. The receiving member is devoid of bristles prior to the engagement of the bristle carriers. Preferably, the static 1403 and movable 1405 bristle carriers independently, slidingly engage the receiving member within separate channels, while in a nested arrangement. This nesting arrangement can be formed by the capturing of the movable bristle carrier within the aperture 1451 of the static bristle carrier (FIGS. 22a-24a). Preferably the static bristles substantially encircle the movable bristles. Although the bristle carriers are in a nested arrangement 1423, the bristle carriers remain separate, as the bristle carriers lack permanent. association with each other. In one embodiment the nesting arrangement 1423 is achieved by slidingly engaging the one or more movable bristle carrier(s) within an aperture 1451 of the one or more static bristle carrier(s), and then slidingly engaging the nested bristle carriers with the receiving member extending from the neck of the toothbrush (FIGS. 22a-24a). Although the bristle carriers engage the receiving member simultaneously, the movable and static bristle carriers engage the receiving member independently of each other. The head of this embodiment of the toothbrush is formed once the bristle carriers, in a nested arrangement, engage the receiving member (FIG. 23a). This independent engagement (shown in FIGS. 22a-27a) is achieved by the static bristle carrier engaging the receiving member within pair of channels 1413 defined by the surfaces of the receiving member via rail 1419 defined by the surfaces of the static bristle carrier 1403 and the movable bristle carrier engaging the receiving member within pair of channels 1411 defined by the surfaces of the receiving member via rail 1407 defined by the surfaces of the movable bristle carrier 1405. It remains possible to separate the nested bristle carriers until connected to the receiving member, because of the lack of permanent association. This facilitates the reciprocating movement of the movable bristle carriers, when the movable bristle carriers are operatively connected to the drive shaft 3205. This nesting arrangement allows the movable bristle carriers to be substantially encircled by static bristles, but remain movable upon operation of the toothbrush. More than one movable bristle carrier can be nested within the static bristle carriers. Additionally, more than one static bristle carrier can be used to substantially encircle the movable bristle carriers. Each bristle carriers can engage the receiving member of the toothbrush in a separate channel, or more than one bristle carriers can engage the receiving member within the same channel. FIG. 24a illustrates the movable and static bristle carriers slidingly engaged with the receiving member of this embodiment of the toothbrush 1401. The movable and static bristle carriers may engage the receiving member in the same channel. In another embodiment the movable and static bristle carriers snap onto the receiving member. The movable bristle carriers can be retained on the receiving member by an operative engagement with the drive shaft. Preferably both the static bristle carriers and the movable bristle carriers can engage the receiving member in a longitudinal direction. However, the carriers can also engage the receiving member in a direction perpendicular to the surface of the receiving member.

A wide array of channel configurations can be used to slidingly engage the nested bristle carriers 1423 with the receiving member 1431 of the toothbrush 1401. These channels should be sized as necessary to direct and/or guide a rail, or other guiding member, located on the bristle carriers. The channels can be various shapes and sizes other than what is shown. Additionally, the channels can be three sided, two sided, or even one sided, so long as the channel is sized to receive or guide the rail, or other guiding member located on the bristle carriers. The receiving member can comprise as many channels as bristle carriers to be engaged. The channels may be configured such that the movable bristle carriers engages an inner set of channels, defined by the surfaces located towards the center of the receiving member, and an outer set of channels, defined by the surfaces located towards the outward edges of the receiving member. Each bristle carriers can have an individual channel, or the bristle carriers can engage the receiving member in the same channel. In the alternative the surface of the receiving member can be formed into a rail to guide the bristle carriers into place. In addition to the channel and rail assembly used to guide the bristle carriers onto the receiving member, other assemblies may be used to retain the bristle carriers on the receiving member. In one embodiment the bristle carriers are retained on the receiving member of the toothbrush by connectors defined by the outer surface of the receiving member, matable with connectors defined by the inner surface of the static bristle carriers. Such connectors include, but are not limited to, serrations and teeth, indentations and tabs, and grooves and protuberances. In one embodiment of the toothbrush the connectors are one or more retaining grooves defined along the inner surfaces of the static bristle carriers, and protuberances 1417 defined along the outer surface of the receiving member wherein the protuberances 1417 reside in the grooves to secure the static bristle carriers on the receiving member. In another embodiment, (not shown), the protuberances are defined along the inner surface of the static bristle carriers, and the grooves are defined along the outer surface of the receiving member, wherein the protuberances reside in the grooves to secure the static bristle carriers. The bristle carriers can also engage the receiving member with a snap type engagement (not shown). In another embodiment the one or more static carrier(s) and/or the one or more movable carrier(s) engage the receiving member with a flexible tongue having a latch hook and a corresponding locking undercut or recess in the opposite attachment part as disclosed in U.S. application Ser. No. 10/361,653 now pending.

When the one or more movable bristle carrier(s) are nested within the static bristle carrier(s), the rail of the movable bristle carrier(s) can extend below the static bristle carrier(s), so that the rail of the movable bristle carrier(s) can engage the receiving member of the toothbrush. When the nested bristle carrier(s) engage the receiving member, the movable bristle carrier(s) can be disposed in the middle and/or center of the head of the toothbrush.

In another embodiment of the invention the nested arrangement occurs only once all the bristle carriers engage the receiving member (not shown). In this embodiment a portion of the receiving member comprises static bristles permanently affixed directly onto the surface of the receiving member. The movable bristle carrier(s) can be substantially surrounded by static bristles when a receiving member provided with bristles, receives one or more movable bristle carrier(s) and then one or more static bristle carrier(s).

The movable bristle carrier(s) is also operatively engaged to the motor. This operative engagement can be achieved by connecting the bristle carrier(s) to a drive shaft that extends through a passage 1428 defined within a portion of the neck 1440 and receiving member 1431. The drive shaft may be rotatably or slidingly disposed within the passage 1428. Once the brush head is formed by the engagement of the bristle carriers to the receiving member, the passage 1428 provides access between the brush head 1421, the neck 1440, and the interior of the body 1480. The distal end of the drive shaft is preferably secured to the movable bristle carrier(s) by the pin 1409, located on the movable bristle carrier(s) 1405, engaging the aperture, located on the tip of the drive shaft (not shown). The tip of the shaft may be flexible, and deflects to facilitate receiving the pin on the movable bristle carrier(s) into the aperture on the tip of the drive shaft. The present invention includes engagement assemblies using pins, protuberances or other fasteners that affix the drive shaft to the movable bristle carrier(s). A snap-fit connection may be utilized between the movable bristle carrier(s) and the distal end of the drive shaft. Examples of snap fit connections include, but are not limited to, serrations on teeth, and a press fit engagement. The present invention also includes all types of motors and gearing arrangements suitable for operating an electric toothbrush, including but not limited to the inventive high efficiency motor discussed herein. These motors can move the drive shaft. The operative connection between the drive shaft and the movable carrier(s) facilitates movement of the movable carriers. The drive shaft, and therefore the movable carrier(s), can undergo any of the aforementioned motions. However, in one embodiment the drive shaft and the movable carrier(s) reciprocates.

It will be understood that the present invention includes assemblies featuring a releasably removable static carrier(s) such as a brush head tip, similar to tip 1430 shown in the noted figures, and/or a releasably removable movable carrier(s). A removable static carrier(s), and/or movable carrier(s) enables a user to selectively tailor and customize a brush as desired. For example, various combinations of static and/or movable carriers include, but are not limited to, bristle carriers, brush head tip carriers, elastomeric element carriers, oral care composition carriers, and dental tool carriers, or any combination thereof. For instance, carriers containing elements that are specifically designed for applying whitening agents to the teeth may be used. It is also contemplated that elastomeric elements or "cushioning" elements may be provided and/or used with the present invention toothbrushes. Such elastomeric elements are formed entirely or partially from thermoplastic elastomers. Elastomeric elements are particularly preferred for incorporation in toothbrushes that utilize one or more other regions or components that are formed from elastomers. For example, the present invention includes toothbrushes as described herein with elastomeric elements and which employ one or more elastomers in gripping regions along the handle, or as "bumpers" or cushioning regions along the brush head. Such elastomers may be co-injected when forming the brush, or may be coated thereon.

The releasable aspect of the carrier(s) may be provided by incorporating a release member along the underside of the brush head that, when pressed or otherwise engaged, allows the carrier to be removed and another carrier positioned in its place. It is further envisioned that the releasable aspect could be achieved by use of a tool or other component to selectively release the carrier from the receiving member. Such a tool could be sold or otherwise commercialized with the toothbrush. Alternatively or in addition, such a tool could be sold or otherwise commercialized with one or more carriers that are sold as a kit for use with the present invention toothbrushes. More specifically, such kits might include one or more of the following and thus incorporate a combination of any of the following components: (i) bristle carriers, brush head tips, elastomeric element carriers, oral care composition carriers, and dental tool carriers, (ii) one or more toothbrushes, (iii) a package or other housing for storing all the components, (iv) one or more tools that might be useful when replacing or substituting or otherwise changing carrier(s), and (v) one or more dentifrice or other compositions for use with the carrier(s) and toothbrush. It is further envisioned that such kits may include batteries for use with the toothbrush, bases or other "stands" for retaining the toothbrush when not in use, replaceable handle components that are used to change the appearance of the toothbrush, and decorative stickers or other types of labels that may be placed on the toothbrush, its stand, and/or the kit housing.

FIGS. 25a through 27a further illustrate embodiments of the static bristle carriers FIG. 25a, the movable bristle carriers FIG. 26a, and the receiving member FIG. 27a. FIG. 25a illustrates an end view of the rails 1419 defined by the surfaces of the static carriers 1403. This embodiment of the invention also has apertures 1435 to receive bristles. Additionally, this embodiment has a cavity 1441 where the receiving member 1431 engages the static carriers. FIG. 26a illustrates an end view of the movable carriers 1405, as well as the rails 1407 defined by the surfaces of the movable carriers. FIG. 27a illustrates an end view of the inventive toothbrush, and in particular the receiving member 1431. The static carriers 1403 engages the receiving member via the channels 1413. The movable carriers 1405 engages the receiving member via the channels 1411. The static carriers can be retained on the receiving member by the protuberance 1417, received into a groove on the inner surface of the static carriers 1403.

A wide array of bristle configurations may be utilized in conjunction with the toothbrushes of the present invention, and particularly those embodiments that utilize a removable or separately formed brush head tip. For instance, static bristles having a height or length that is equal to that of the movable bristles may be utilized. Any of the previously noted configurations of the static bristles and movable bristles shown in the referenced figures, described herein, or noted in Table 1 may be utilized. Specifically, FIGS. 25 and 26 illustrate the head of the toothbrush 1433 and the neck 1440 of one embodiment of the brush 1400 with a collection of static bristles 1460 disposed on a tip 1430 at the distal end of the toothbrush head 1433 and a collection of movable bristles 1450 disposed on a movable bristle carriers 1452 (the carriers 1452 shown in dashed lines). Preferably, the height of the movable bristles 1450 along the toothbrush head 1433, designated in FIG. 25 as dimension C, ranges from about 3 mm to about 14 mm, and preferably from about 7 mm to about 11 mm. Generally, bristle height is the distance of a bristle as measured from an outwardly directed surface, i.e. typically the surface of its base or mounting component, to the end or tip of the bristle. The noted outwardly directed surface of a bristle mounting component is generally referred to herein as a brush-facing surface. Although not shown in FIG. 25, it will be appreciated that a plurality of static bristles, supported and retained directly on the head of the toothbrush 1433, are preferably disposed around the movable bristles 1450. It will be appreciated that such static bristles are not shown in these figures (nor in FIGS. 27-30) for purposes of clarity. The preferred height of the static bristles (those disposed around the movable bristles 1450 and those disposed on the tip 1430) also ranges from about 3 mm to about 14 mm, and preferably from about 7 mm to about 11 mm.

It is also contemplated to provide static bristles having a varying length, and particularly, arranged in a manner so as to provide an inclined brushing surface. This is shown in FIGS. 27 to 33. The term "brushing surface" as used herein refers to the distal ends of bristles or elastomeric elements that contact a user's teeth or gums during brushing.

Figure 27:
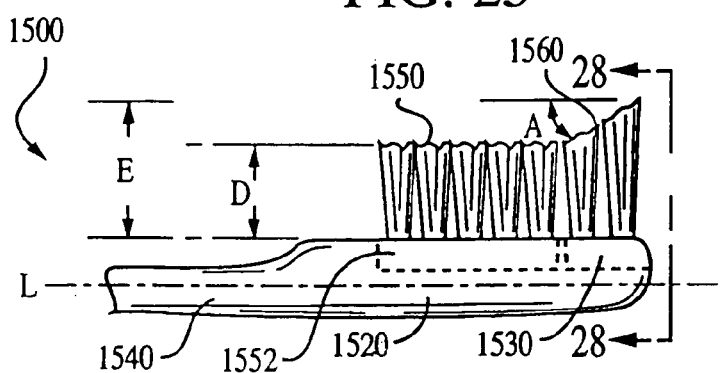
FIG. 27 is a partial side elevational view of a toothbrush head of the toothbrush illustrating another bristle configuration in accordance with the present invention.
Figure 28:
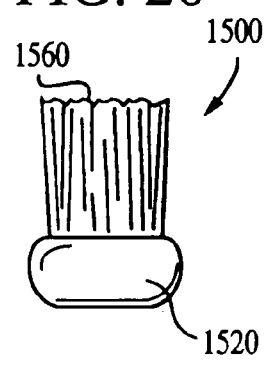
FIG. 28 is an end view of the toothbrush head shown in FIG. 27 taken along line 28-28.
Figure 27A:
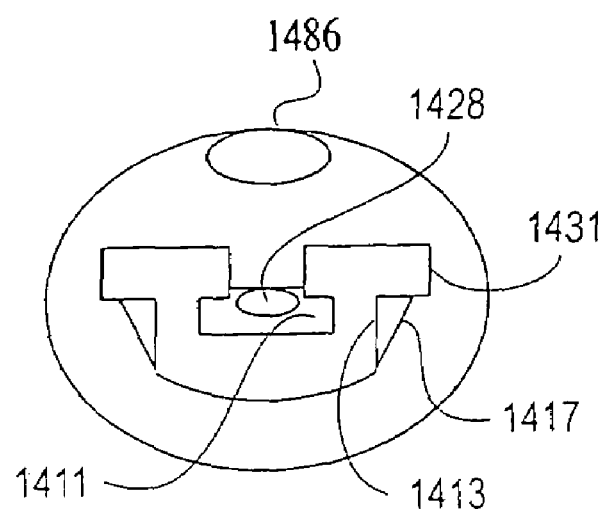
FIG. 27a is an end view of the toothbrush of FIG. 21a prior to engagement of static and movable bristle carriers.

Specifically, FIGS. 27 and 28 illustrate a toothbrush head 1520 and a neck 1540 of another embodiment of the toothbrush 1500 according to the present invention. The brush head 1520 includes a movable bristle carriers 1552 having a plurality of movable bristles 1550 (the carriers 1552 shown in dashed lines) supported or retained therein. The brush head 1520 also includes a tip 1530 having a collection of static or stationary bristles 1560 supported or retained thereon. It will be appreciated that a plurality of stationary bristles 1560 preferably surround, or at least partially so, the movable bristles 1550. For clarity, that portion of bristles supported directly on the brush head 1520 is not shown in FIG. 27. The tip 1530 preferably includes stationary bristles 1560 having different lengths and arranged so as to provide an inclined brushing surface. When providing an inclined brushing surface, such as specifically shown in FIG. 27, the angle A, which is the angle of the inclined surface with respect to the longitudinal axis of the neck 1540 and head 1520, may range from about 5 degrees to about 85 degrees, and preferably from about 20 degrees to about 70 degrees. Most preferably, the longer bristles are disposed adjacent the distal end of the head 1520. The height of the movable bristles 1550, designated in FIG. 27 as dimension D, ranges from about 3 mm to about 14 mm, and preferably from about 7 mm to about 11 mm. The height of the static bristles 1560 ranges from about 3 mm to about 18 mm, and preferably from about 7 mm to about 11 mm. The maximum height of the static bristles 1560 and particularly those disposed at the distal end of the head 1520 is about 18 mm. That dimension is shown as dimension E in FIG. 27.

Figure 29:
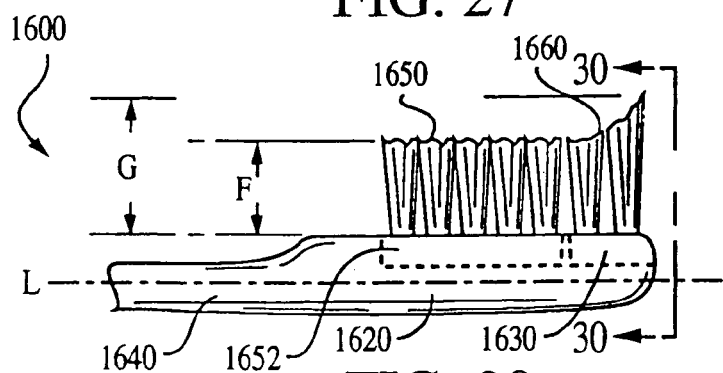
FIG. 29 is a partial side elevational view of the toothbrush illustrating yet another preferred bristle configuration in accordance with the present invention.
Figure 30:
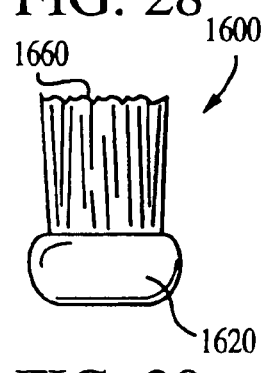
FIG. 30 is an end view of the toothbrush head shown in FIG. 29 taken along line 30-30.

FIGS. 29 and 30 illustrate yet another preferred configuration for bristle configurations. These figures illustrate an embodiment of the toothbrush 1600 having a neck 1640, a toothbrush head 1620, a movable bristle carriers 1652 (shown in dashed lines) having movable bristles 1650, a toothbrush head tip 1630, and a collection of static bristles 1660 located on the end tip 1630 disposed at the end of the toothbrush head 1620. In this embodiment, the collection of static bristles 1660 on the tip 1630 are arranged so as to provide an inclined brushing surface. The height of the movable bristles 1650, designated in FIG. 29 as dimension F, ranges from about 3 mm to about 14 mm, and preferably from about 7 mm to about 11 mm. The height of the static bristles 1660, ranges from about 3 mm to about 18 mm, and preferably from about 7 mm to about 11 mm. The maximum height of the static bristles 1660 and particularly those disposed at the distal end of the head 1620 is about 18 mm. That dimension is shown as dimension G in FIG. 29. The embodiment illustrated in FIGS. 29 and 30 differs from that depicted in FIGS. 27 and 28 primarily in that the static bristles 1660 disposed on the brush head tip 1630 do not linearly vary in height from one end of the tip 230 to the other, as do the bristles 150 in FIG. 27. Restated, the resulting surface defined by the distal ends of the bristles 150 in FIG. 27 is generally straight, whereas the resulting surface defined by the distal ends of the bristles 1660 in FIG. 29 is generally arcuate.

Figure 31:
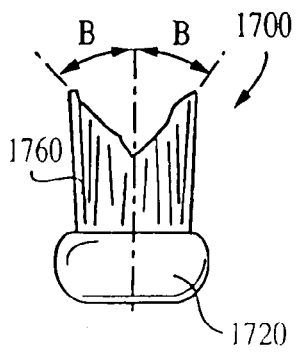
FIG. 31 is an end view of the toothbrush head illustrating another bristle configuration in accordance with the present invention.
Figure 32:
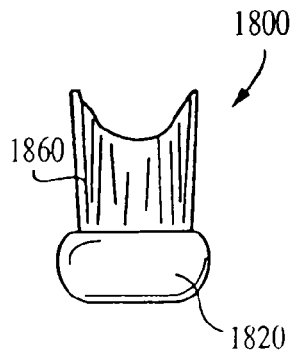
FIG. 32 is an end view of the toothbrush head in accordance with the present invention illustrating yet another bristle configuration.
Figure 33:
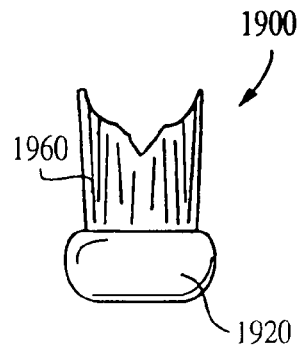
FIG. 33 is an end view of the toothbrush head in accordance with the present invention illustrating another bristle configuration.

It is also contemplated to utilize various bristle configurations at the toothbrush head tip which provide varying inclinations and changing bristle height across the width of the brush head as shown in FIGS. 31 to 33. Specifically, FIG. 31 illustrates an embodiment of the toothbrush 1700 having a brush head 1720 and a plurality of static bristles 1760. The bristles 1760 provide an inclined brushing surface that forms an angled valley, when viewed along a line in the same direction as the longitudinal axis of the brush head 1720 and neck (not shown in FIG. 31). Preferably, each side of the valley formed by the distal ends of the bristles 1760 is symmetrical and extends so as to form an angle B with respect to a vertical line perpendicular to a longitudinal axis of the brush head 1720 and neck (not shown). Angle B may range from about 10° to about 80°, and preferably from about 30° to about 60°

FIG. 32 illustrates another embodiment of the toothbrush 1800 having a brush head 1820 with a plurality of static bristles 1860 extending therefrom. The contoured or arcuate brushing surface provided by the distal ends of the bristles 1860 may be in the form of a concave region or surface as shown in FIG. 32.

FIG. 33 illustrates another embodiment of the toothbrush 1900 having a brush head 1920 and a plurality of static bristles 1960 extending therefrom. The bristles 1960 may provide an irregular brushing surface as shown.

Figure 34:
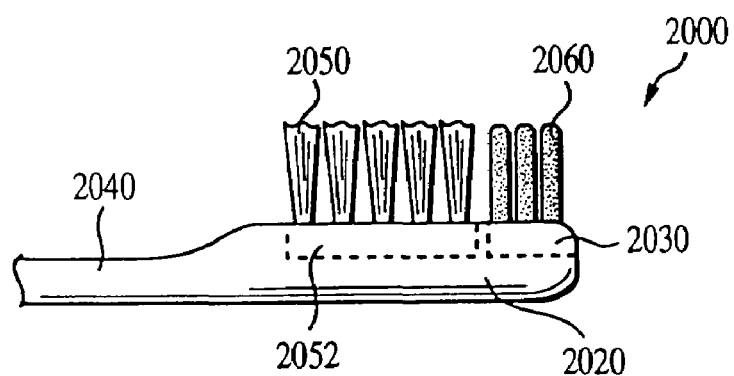
FIG. 34 is a partial side elevational view of the toothbrush head in accordance with the present invention illustrating another bristle configuration.

FIG. 34 illustrates a portion of another embodiment of the toothbrush 2000. This toothbrush comprises a brush head 2020, a neck or intermediate portion 2040, a movable bristle carriers 2052 (shown in dashed lines), a brush head tip 2030 (shown in dashed lines), and a plurality of bristles 2050 and a plurality of elastomeric elements 2060. The bristles 2050 may include movable bristles, static bristles, or both, as described herein. The elastomeric elements 2060 massage the gums while the user simultaneously brushes his or her teeth. The elastomeric elements can be made from a rubber, soft plastic or similar material. The elastomeric elements are preferably formed from an elastomeric material. The elastomeric elements extend essentially perpendicularly from the toothbrush head 2020 as measured along the longitudinal axis of the toothbrush 600. In one of the embodiments of the toothbrush 2000, the elastomeric elements 2060 are located proximate the distal end of the toothbrush head 2020, and most preferably along the brush head tip 2030 as described herein. However, it is to be understood that the elastomeric elements can be located anywhere among the moving and static bristles. The height of the elastomeric elements 2060 is approximately the same height as the bristles 2050. The elastomeric elements 2060 may extend slightly above, slightly below or to the same height as the bristles 2050.

Figure 35:
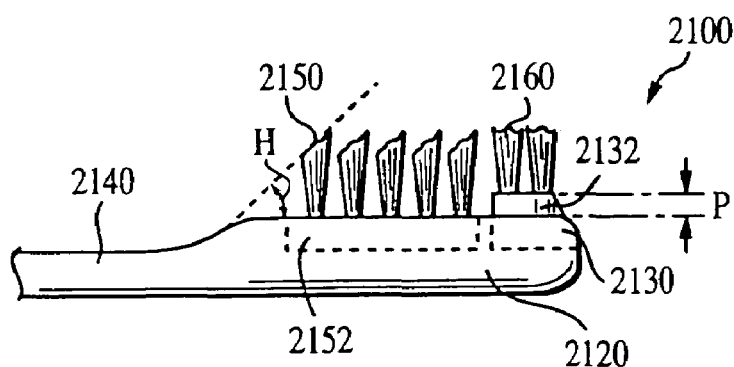
FIG. 35 is a partial side elevational view of the toothbrush head in accordance with the present invention illustrating another bristle configuration.

FIG. 35 illustrates another embodiment of the toothbrush 2100 comprising a toothbrush head 2120, a movable bristle carriers 2152 (shown in dashed lines), and a neck or intermediate portion 2140. The toothbrush 700 includes a plurality of bristles 2150 and a second set of bristles 2160 disposed on a brush head tip 2130 (shown partially in dashed lines). In this embodiment, the bristles 2150 are arranged in groups of tufts wherein each tuft contains bristles of various lengths or heights. The bristles of varying height are arranged within each tuft such that the distal ends of the bristles form an inclined surface with respect to the generally flat surface or brush-facing surface of the brush head 2120. Preferably, this inclined surface forms an angle H with respect to the flat face of the brush head 2120. Angle H is in the range of from about 10° to about 90° and preferably from about 20° to about 45°.

The second set of bristles 2160 disposed on the brush head tip 2130 are preferably also arranged in groups or tufts. The preferred height of bristles 2160 is approximately equal to the maximum bristle height of the bristles 2150. FIG. 35 illustrates a particularly preferred feature of the present invention toothbrushes, and relating to the configuration of the brush head tip 2130. The brush head tip 2130 is provided with a region 2132 having a relatively large thickness such that its flat, brush-facing surface generally extends above the brush-facing surface of the carriers 2152. This difference in height between the brush-facing surfaces of the regions of bristles 2150 and bristles 2160 is illustrated in FIG. 35 as dimension P. Preferably, P is from about 1 to about 5 mm.

Figure 36:
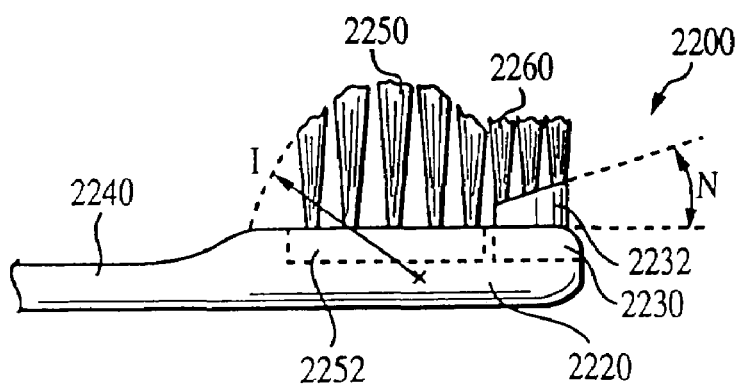
FIG. 36 is a partial side elevational view of the toothbrush head in accordance with the present invention illustrating another bristle configuration.

FIG. 36 is another illustration of an embodiment of the toothbrush 2200 having a head 2220, a movable bristle carriers 2252 (shown in dashed lines), and a neck 2240. Disposed on the brush head 2220 are a plurality of upwardly extending bristles 2250. The toothbrush 2200 also includes a brush head tip 2230 (shown partially in dashed lines) disposed at the distal end of the brush and having a region 2232 that extends above the flat, brush-facing surface of the brush head 2220 and the carriers 2252. The plurality of bristles 2250 are preferably configured such that their outermost ends, when viewed in planar fashion as shown in FIG. 36, define an arcuate brushing surface, preferably having a common radius as shown in FIG. 36, designated as I. The brush head tip 2230 includes the raised region 2232 that is preferably formed to define a sloping surface with respect to the flat, brush-facing surface of the brush head 2220 and the carriers 2252. This angle of slope is shown in FIG. 36 as angle N. Angle N may range from about 10° to about 80°, with 15° to 45° being preferred. The height of the bristles 2260 may be greater or lesser than any of the heights of the bristles 2250. The bristle configuration depicted in FIG. 36 is exemplary.

Figure 37:
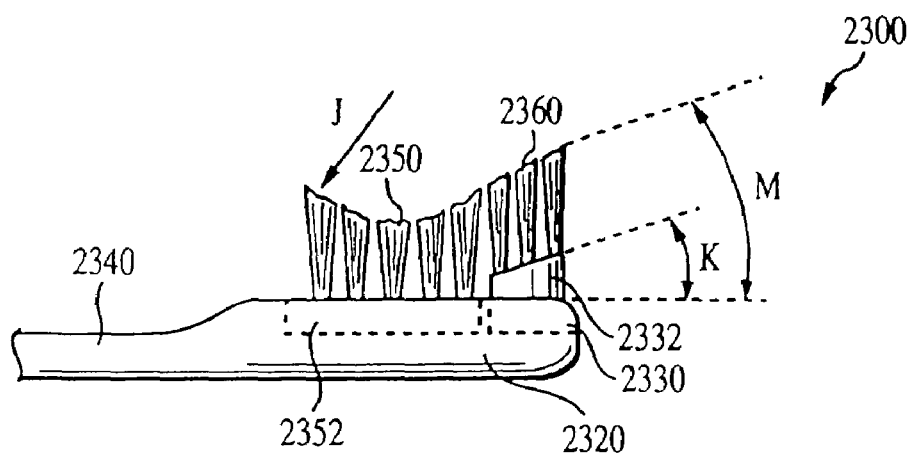
FIG. 37 is a partial side elevational view of the toothbrush head in accordance with the present invention illustrating another bristle configuration.

FIG. 37 illustrates another embodiment of the toothbrush 2300 according to the present invention. Toothbrush 2300 comprises a brush head 2320, a movable bristle carriers 2352 (shown in dashed lines), and a neck 2340. The toothbrush 2300 includes a plurality of bristles 2350 and another set of bristles 2360 disposed on a brush head tip 2330 (partially shown in dashed lines). The brush head tip includes a raised region 2332 extending above the brush-facing surface of the brush head 2320 and carriers 2352. The outermost surface of the raised region 2332 of the brush head tip 2330 is preferably sloped at an angle K as shown in FIG. 37. Angle K may range from about 10° to about 80°, with 15° to 45° being preferred. The bristles 2350 are also particularly configured such that their outermost or distal ends define a concave brushing surface, preferably having a common radius J as shown in FIG. 37. The height of the bristles 2360 may be greater or lesser than any of the heights of the bristles 950. However, it may in some applications be preferred to arrange the bristles 2360 such that their distal ends generally extend within a plane that is parallel with the sloping surface of the raised region 2332 of the brush head tip 2330. This angle M preferably corresponds to angle K, and so may range from about 10° to about 80° with 15° to 45° being preferred.

Figure 38:
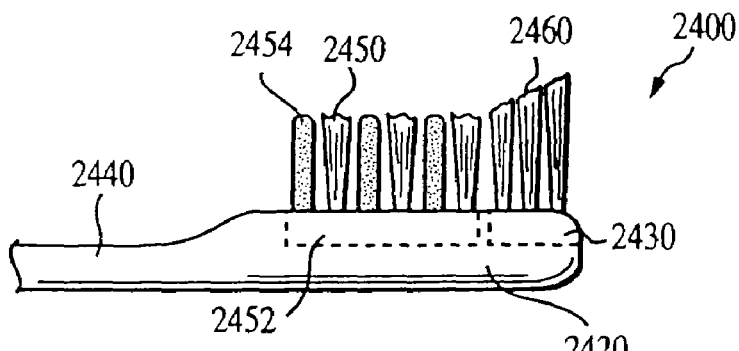
FIG. 38 is a partial side elevational view of the toothbrush head in accordance with the present invention illustrating another bristle configuration.

FIG. 38 is another embodiment of the toothbrush 2400 having a brush head 2420, a movable bristle carriers 2452 (shown in dashed lines), a brush head tip 2430 (also shown in dashed lines), and a neck 2440. The toothbrush 2400 includes a plurality of bristles 2450, a second set of bristles 2460 disposed on the brush head tip 2430, and a plurality of elastomeric elements 2454. The arrangement, height, and configuration of the bristles 2450, 2460, and elastomeric elements 2454 may be as described herein with regard to any of the other embodiments.

Figure 39:
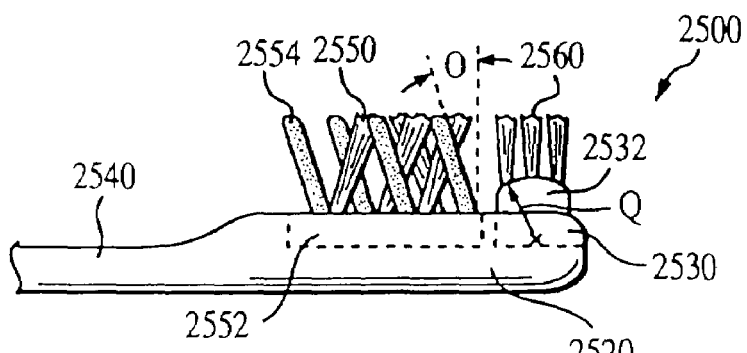
FIG. 39 is a partial side elevational view of the toothbrush head in accordance with the present invention illustrating another bristle configuration.

FIG. 39 illustrates another embodiment of the toothbrush 2500 having a brush head 2520, a movable bristle carriers 2552 (shown in dashed lines), and a neck 2540. The toothbrush 2500 includes a plurality of bristles 2550 and a plurality of elastomeric elements 2554 preferably disposed at opposing angles from each other. That is, the elastomeric elements 2554 preferably extend at an angle O as shown in FIG. 39. The collection of bristles 2550 preferably extend in the opposite direction but at a similar angle. The toothbrush 2500 also includes a plurality of bristles 2560 extending from a brush head tip 2530 (shown partially in dashed lines). The brush head tip may also include a region 2532 extending above the flat, brush-facing surface of the brush head 2520. This raised region 2532 may further provide an arcuate outer surface that may be defined by a common radius such as radius Q shown in FIG. 39. The arrangement, height, and configuration of the bristles 2550, 2560 and elastomeric elements 2554 may be as described herein with regard to any of the other embodiments.

Figure 40:
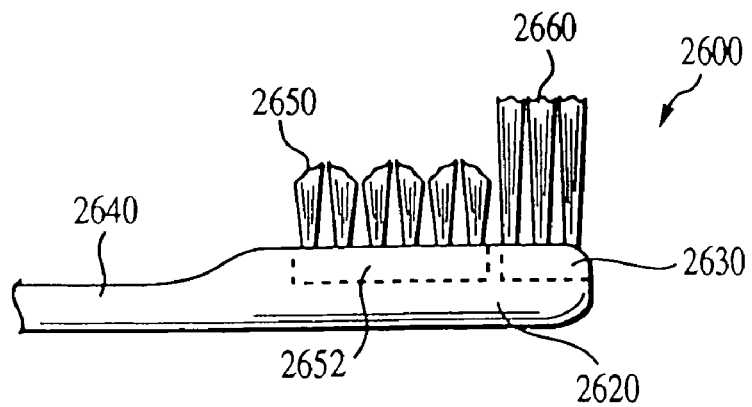
FIG. 40 is a partial side elevational view of the toothbrush head in accordance with the present invention illustrating another bristle configuration.

FIG. 40 illustrates yet another embodiment of the toothbrush 2600 having a brush head 2620, a movable bristle carriers 2652 (shown in dashed lines), and a neck 2640. The toothbrush 2600 includes a brush head tip 2630 (also shown in dashed lines) having a plurality of bristles 2660 extending therefrom. Another set of bristles 2650 are provided on the brush head 2620, and specifically on the movable bristle carriers 2652. In this embodiment, the height of the bristles 2660 is significantly greater than the height of the bristles 2650. As previously described herein, the bristles 2650, 2660 may be arranged in groups or tufts wherein the bristles within a particular tuft may have different lengths.

Figure 41:
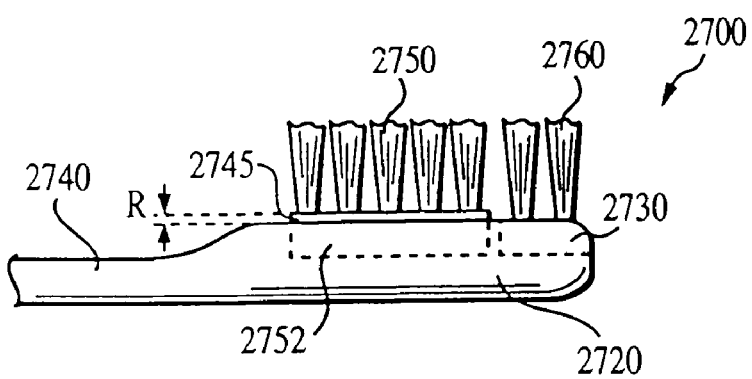
FIG. 41 is a partial side elevational view of the toothbrush head in accordance with the present invention illustrating another bristle configuration.

FIG. 41 illustrates yet another embodiment of the toothbrush 2700 having a brush head 2720, a neck 2740, a movable bristle carriers 2752 (shown partially in dashed lines), a plurality of bristles 2750 extending from the bristle carriers 2752, and another set of bristles 2760 extending from a brush head tip 2730 (shown in dashed lines). In this embodiment, the bristle carriers 2752 has a relatively large thickness such that its flat, brush-facing surface is generally elevated above or disposed closer to the user during brushing, than the brush-facing surface of the brush head tip 2730 and other portions of the brush head 2720. The elevated portion of the bristle carrier 2752 that extends past the adjacent regions of the brush head 2720 and the brush head tip 2730 is designated in FIG. 41 as 2745. For bristle configurations in which the distal ends or brushing surfaces of the bristles 2750 and 2760 generally extend along a common plane, the resulting shorter length of bristles 2750 imparts an increased stiffness to those bristles. The extent of elevation of the region 2745 of increased thickness is shown in FIG. 41 as dimension R. R may range from about 1 mm to about 5 mm.

Figure 42:
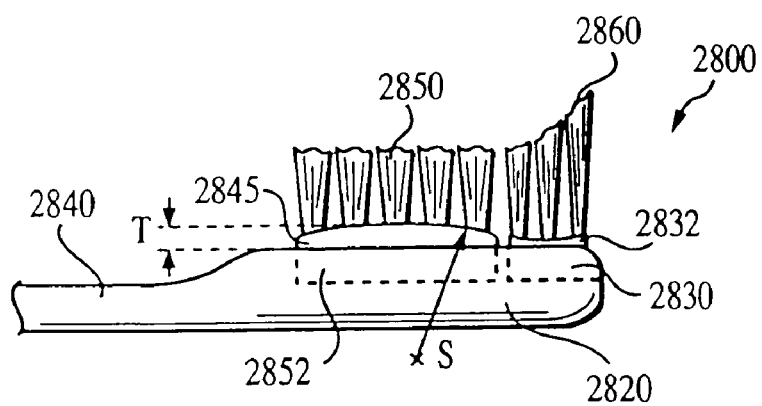
FIG. 42 is a partial side elevational view of the toothbrush head in accordance with the present invention illustrating another bristle configuration.

FIG. 42 illustrates another embodiment of the toothbrush 2800 having a brush head 2820 and a neck 2840. A plurality of bristles 2850 are provided on the brush head and extend from a bristle carrier 2852 (partially shown in dashed lines) which is preferably movable with respect to the head 2820. The toothbrush 2800 also comprises another plurality of bristles 2860 that extend from a brush head tip 2830 (partially shown in dashed lines). In this embodiment, the brush-facing surface of the bristle carriers 2852 is preferably sloping, more preferably arcuate, and most preferably convex as shown in FIG. 42. In the event this surface is convex, it is further defined by a radius S as shown in FIG. 42. The upwardly directed brush-facing surface of the bristle carrier 2852 is also preferably elevated above the relatively flat, brush-facing surface of the brush head 2820, preferably by dimension T shown in FIG. 42. Dimension T may range from about 1 mm to about 5 mm. The elevated portion of the bristle carrier 2852 that extends past the adjacent regions of the brush head 2820 is designated as 2845. The brush-facing surface of the brush head tip 2830 is preferably arcuate and more preferably concave. The elevated portion of the bristle carrier 2830 that extends past the adjacent regions of the brush head 2820 is designated as 2832. The arrangement, height, and configuration of the bristles 2850 and 2860 may be as described herein with regard to any of the other embodiments.

Figure 43:
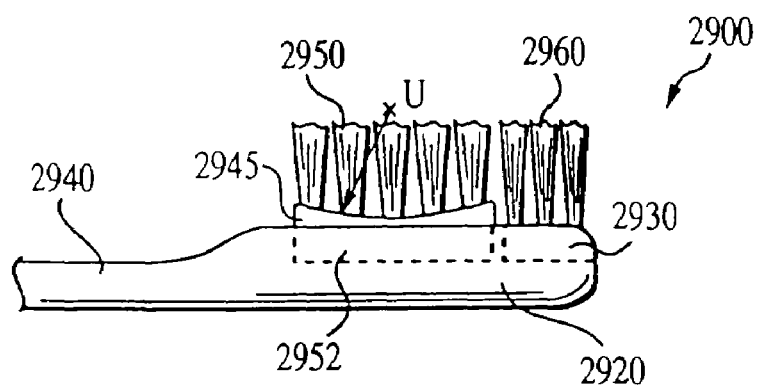
FIG. 43 is a partial side elevational view of the toothbrush head in accordance with the present invention illustrating another bristle configuration.

FIG. 43 illustrates another embodiment of the toothbrush 2900 having a brush head 2920, a movable bristle carrier 2952 (shown partially by dashed lines), a brush head tip 2930 (shown by dashed lines), and a neck 2940. A collection of bristles 2950 extend from the bristle carrier 2952. And, another collection of bristles 2960 extend from the brush head tip 2930. The bristles 2950 are preferably disposed and retained on the movable bristle carrier 2952. The bristle carrier 2952 provides an upwardly directed, brush-facing surface which is depicted in FIG. 43 as concave. Preferably, this concave surface is defined by a common radius U. The elevated portion of the bristle carrier 2952 that extends past the adjacent regions of the brush head 2920 is shown as region 2945. The arrangement, height, and configuration of the bristles 2950 and 2960 may be as described herein with regard to any of the other embodiments.

Figure 44:
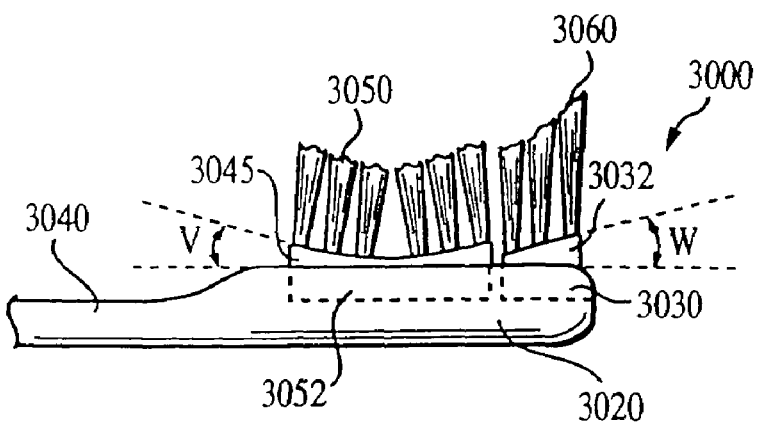
FIG. 44 is a partial side elevational view of the toothbrush head in accordance with the present invention illustrating another bristle configuration.

FIG. 44 illustrates yet another embodiment of the toothbrush 3000 according to the present invention. The toothbrush 3000 comprises a brush head 3020 and a neck 3040. The toothbrush 3000 includes a plurality of bristles 3050 extending from a bristle carrier 3052 (shown partially in dashed lines) that is movably disposed on the brush head 3020. And, the toothbrush 3000 includes another set of bristles 3060 extending from a brush head tip 3030 (shown partially in dashed lines). The outermost surface of the bristle carrier 3052 may be provided such that it has one or more sloping surfaces defined along a raised region 3045 as shown in FIG. 44. These slopes may be carried through such that the distal-most ends of the bristles 3050 mirror this same slope or, another or different slope. Similarly, the outermost end of the bristles 3060 may also reflect the sloping surface of a raised region 3032 of the brush head end 3030. Preferably, the bristle carrier 3052 provides at least a region having a sloping brush-facing surface. That slope preferably extends along an angle V as shown in FIG. 44. Angle V preferably is from about 10° to about 60°, and more preferably from about 20° to about 30°. Similarly, the brush head tip 3030 preferably provides a sloping brush-facing surface that extends along an angle W. Angle W preferably ranges from about 10° to about 45°.

Figure 45:
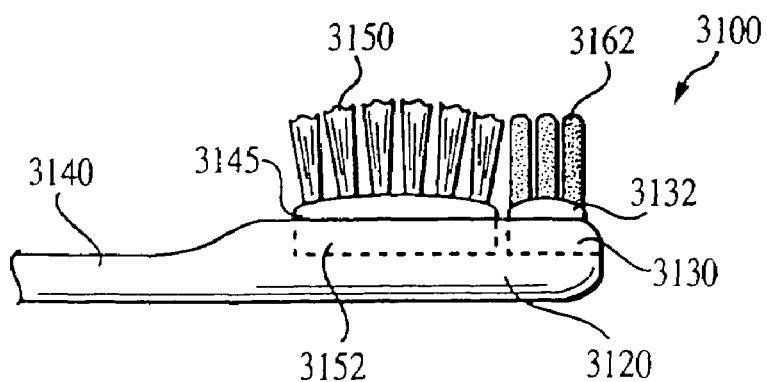
FIG. 45 is a partial side elevational view of the toothbrush head in accordance with the present invention illustrating another bristle configuration.

FIG. 45 is another embodiment of the toothbrush 3100 having a brush head 3120 and a neck 3140. The toothbrush 3100 includes a plurality of elastomeric elements 3162 extending from a brush head tip 3130 (shown partially in dashed lines). The toothbrush 3100 also comprises a plurality of bristles 3150 extending from a movable bristle carriers 3152. The bristle carriers 3152 contains a region 3145 that is raised relative to the adjacent regions of the brush head 3120. Similarly, the brush head tip 3130 contains a region 3132 that is raised relative to the adjacent regions of the brush head 3120. Either or both of the outwardly directed, brush-facing surfaces of the bristle carriers 3152 and the brush head tip 3130, may be flat, sloping, arcuate, convex or concave. Furthermore, the arrangement, height, and configuration of the bristles 3150 and elastomeric elements 3162 may be as described herein with regard to any of the other embodiments.

Another preferred bristle configuration is similar to the configurations shown in FIGS. 36 and 45, i.e. having an interior group of bristles that extend "above" or have a greater height than adjacent bristles, however features a stepped or plateau configuration. In this configuration, the change in bristle height is not gradual or varying as shown in FIGS. 36 and 45, but instead is stepped. That is, the change in height from shorter bristles disposed around the taller medially disposed bristles is rather abrupt. The difference in height between these two groups of bristles is about 0.5 mm to about 3 mm, and more preferably from about 0.75 mm to about 1.5 mm.

Referring to the various bristle carriers illustrated and described herein, it can be seen that the profile or configuration of the outwardly facing surface of the carrier, generally referred to herein as a brush-facing surface, may be in a variety of forms and shapes. One particularly preferred shape is a concave shape (when viewing the bristle carrier from its side, and its side that generally extends along the same direction as the longitudinal axis of the toothbrush). A concave shape promotes the retention of dentifrice or polishing material that may be used during brushing. Likewise, a convex surface promotes the dissipation of dentifrice in the region of the bristles along the brush head. Most preferably, bristle carriers in accordance with the present invention utilize a non-flat brush-facing surface.

Another aspect of interest in the design of a brush head is the selection, placement, and configuration of bristles along the bristle carrier, brush head tip, and brush head. Generally, the stiffness of a bristle or tuft of bristles increases as the length of the bristle(s) decreases. Thus, changes in bristle stiffness may be achieved by altering the length of the subject bristles. This characteristic is important to consider when providing a bristle carrier having a brush-facing surface that is non-planar. It will be appreciated that bristle stiffness will vary at different locations along the bristle carrier since the length or height of the bristles extending therefrom varies. Alternatively, the stiffness of bristles having equal heights will be generally the same. The present invention includes a wide array of different combinations of bristle carrier shapes and configurations; and bristle length, materials, and configuration. Many of these preferred configurations have been exemplified in the referenced figures. Additionally, in some embodiments, it is preferred to utilize diameters of bristles and/or diameters of tufts of bristles on the movable bristle carrier that are larger than corresponding diameters of bristles or tufts of bristles that are disposed on the brush head tip. In yet other embodiments, it may be desirable to utilize diameters of bristles/tufts on the carrier that are smaller than corresponding bristles/tufts on the tip.

Figure 46:
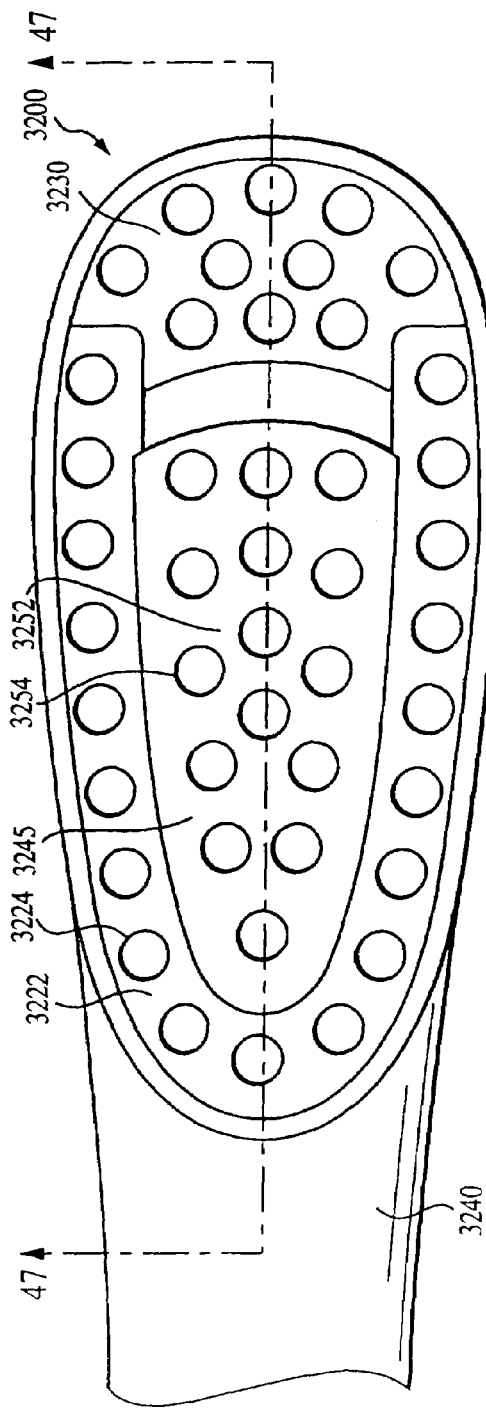
FIG. 46 is a planar bottom view of a toothbrush head (without bristles) of the toothbrush according to the present invention.
Figure 47:
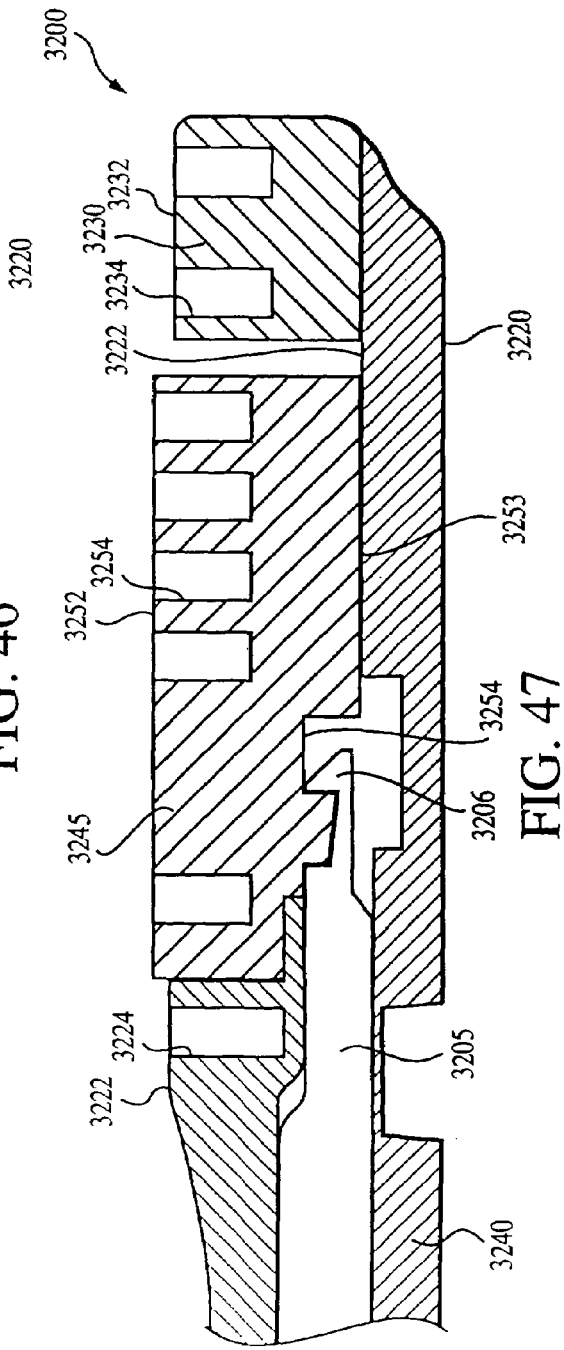
FIG. 47 is a cross-sectional view of the toothbrush head illustrated in FIG. 46, taken across line 47-47.

FIGS. 46 and 47 illustrate in greater detail a preferred brush head 3220 of an embodiment of the toothbrush 3200 according to the present invention. The toothbrush 3200 comprises a brush head 3220 and a neck 3240 integrally formed with and extending therefrom. The toothbrush 3200 further comprises a movable bristle carrier 3245 defining a plurality of holes or apertures 3254 adapted for receiving and retaining bristles or bristle tufts (not shown). The bristle carrier 3245 provides an outwardly directed brush-facing surface 3252. Defined along an oppositely directed face is an under-surface 3253. A receiving aperture 3254 is also defined along the under-surface 3253 and is sized and adapted to receive and engage a distal end 3206 of a movable drive shaft 3205. As will be appreciated, the drive shaft 3205 reciprocates within the neck 3240 and imparts a similar reciprocating type motion to the bristle carrier 3245. The toothbrush 3200 also comprises a brush head tip 3230 defining an outwardly directed brush-face surface 3232 and one or more apertures 3234 adapted to receive and retain bristles or bristle tufts (not shown). The brush head 3220 may also define one or more apertures located along the brushing face of the head 3220, such as apertures 3224 defined in the region 3222 of the head 3220.

Although the assembly shown in FIG. 47 for engaging the bristle carrier 3245 with the shaft 3205 is generally preferred, i.e. use of a notched distal end 3206 that is received in aperture 3254, other assemblies for engaging a movable bristle carrier with a drive shaft may be utilized. For example, the present invention includes engagement assemblies using pins or other fasteners that affix the drive shaft to the carrier. Alternatively, other assemblies may be used such as snap-fit connections, releasable engagement assemblies, and nonreleasable assemblies. The materials employed for the components of the engagement assemblies can be polymeric, metal, or any other material having suitable strength and durability properties.

Figure 48:
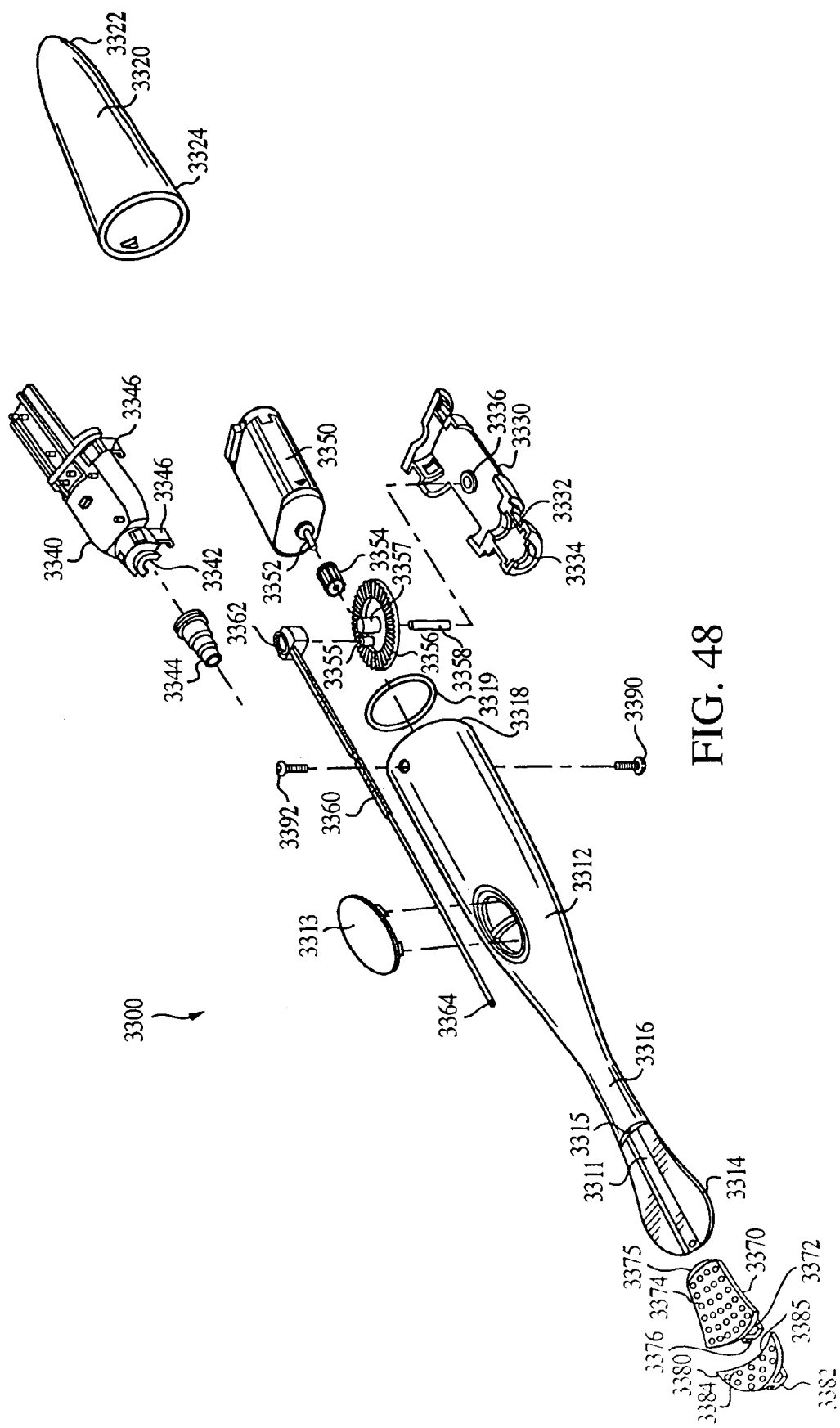
FIG. 48 is a partial exploded view of the toothbrush in accordance with the present invention.

FIG. 48 is a partial exploded view of an embodiment of the toothbrush 3300 according to the present invention. This embodiment of the inventive toothbrush 3300 comprises a body or housing 3312 and an end cap 3320. The body 3312 is essentially a one-piece body having a major portion including a neck 3316 and an end 3318, and a brush head 3314 extending from the neck 3316. Preferably, the brush head 3314, neck 3316, and body 3312 are generally continuous and integrally formed with one another. The body 3312 and portions of the neck 3316 and head 3314, define a hollow interior region, which house a drive mechanism. The major portion of the body 3312 also defines a recessed region or one or more apertures along its outer surface which receives an electrical switch (not shown) for operating the drive mechanism of the electric toothbrush described in greater detail herein. A protective cover 3313 preferably fits within this recessed region. The end cap 3320 includes a closed end 3322 and an opposite open end 3324. The open end 3324 is sized to engage and generally seal the end 3318 of the housing 3312. An O-ring or other sealing member 3319 may be used at the interface of the ends 3318 and 3324 of the housing components.

One of the embodiments of the toothbrush further comprises a drive motor 3350 having a drive shaft 3352. The motor 3350 is a DC motor similar to motors known to those skilled in the art and includes various switching circuits and a battery or other power source (not shown). These components are housed and retained within the hollow interior region defined in the body 3312 and optionally within the end cap 3320. A drive gear 3354 is engaged to the drive shaft 3352. A lower motor mount 3330 is provided. An upper motor mount 3340 is also provided which, together with the lower motor mount 3330, generally cradle, retain, and secure the motor 3350 within the interior of the housing 3312 and cap 3320. The lower motor mount 3330 includes inner and outer drive shaft supports 3332 and 3334, respectively. The lower motor mount 3330 also includes a base or aperture 3336 for receiving a mount or axle 3358 for a drive gear described in greater detail herein. The upper motor mount 3340 includes an inner drive shaft support 3342 and a drive shaft housing 3344 which preferably engages the inner mount 3342 and optionally the outer mount 3334 of the lower motor mount 3330. The upper motor mount 3340 additionally includes a plurality of engagement legs 3346 that preferably engage the lower motor mount 3330 for retaining motor 3350 disposed between the two assemblies. It will be appreciated that instead of utilizing an upper and lower motor mount, a single one-piece mount or retaining structure could be employed.

The drive gear 3354 is engaged with a crown gear 3356. Crown gear 3356 is rotatably supported at its center 3357 by the axle or pivot member 3358. The crown gear 3356 includes an offset engagement member 3355 to which is attached a pinion end 3362 of a drive shaft 3360. The drive shaft 3360 includes the noted pinion end 3362 that includes a receiving aperture or other engagement member for engagement with the offset member 3355. The drive shaft 3360 further includes a distal end 3364 which is used to engage and thus drive a movable bristle carrier described in greater detail herein. The drive shaft 3360 extends within the interior hollow cavity of the housing 3312 and preferably through at least a portion of the neck 3316. The distal end 3364 of the drive shaft 3360 is engaged with a bristle carrier 3370, described below. The end 3364 is accessible through an aperture in the brush head 3314.

This embodiment of the toothbrush 3300 further includes a movable bristle carrier 3370 which, upon assembly in the toothbrush 3300, reciprocates along the brush head 3314. Preferably, the movable bristle carrier 3370 reciprocates within a channel 3311 defined along the brush head 3314, and most preferably in a direction parallel with the longitudinal axis of the toothbrush 3300. Disposed along the underside of the bristle carrier 3370 is a ridged member 3372. This ridged member 3372 is configured to move within, yet be retained by, the channel 3311. The bristle carrier 3370 defines a plurality of apertures 3374 within which are disposed a plurality of bristles or bristle tufts (not shown). The bristle carrier 3370 includes a first end 3375 which, upon assembly with the brush head 3314, is preferably disposed adjacent a region or edge 3315 defined between the neck 3316 and the brush head 3314 of the body or housing 3312. The opposite end of the movable bristle carrier 3370 is end 3376 and is preferably curvilinear as shown in FIG. 48.

This embodiment of the toothbrush 3300 further comprises a stationary bristle carrier tip 3380 which defines a plurality of apertures 3384 for retaining bristles or bristle tufts (not shown), a first end 3385 which engages or is disposed adjacent to the end 3376 of the movable bristle carrier 3370, and a ridged member 3382 disposed along the underside of the tip 3380. By "stationary" it is meant that the carrier tip 3380, once assembled and engaged with the brush head 3314, is generally secured to the brush head 3314 and does not move with the bristle carrier 3370. Preferably, the ridged member 3382 is sized in a similar fashion and configuration as the ridged member 3372 of the bristle carrier 3370. Both of the ridged members 3372 and 3382 are preferably retained within channel 3311 defined in the brush head 3314.

One or more threaded fasteners 3390 and 3392 may be utilized to affix the body 3312 to the end cap 3320. It will be understood that other techniques or components may be utilized to assemble the housing together.

Upon operation of this embodiment of the toothbrush 3300, an electrical circuit is completed between a power source such as a battery and the motor 3350. Details as to the power source and electrical operating characteristics of the motor are provided herein. Rotation of the drive gear 3354 causes rotation of the crown gear 3356. Preferably, the axis of rotation of the crown gear 3356 is perpendicular or transverse to the axis of rotation of the drive gear 3354.

Rotation of crown gear 3356 imparts a reciprocating motion to the drive shaft 3360 extending within the hollow interior region defined within the body 3312, neck 3316, and optionally the head 3314. The distal end 3364 of the drive shaft is engaged with the movable bristle carrier 3370, and so, imparts a corresponding reciprocating motion to the carrier 3370.

Figure 49:
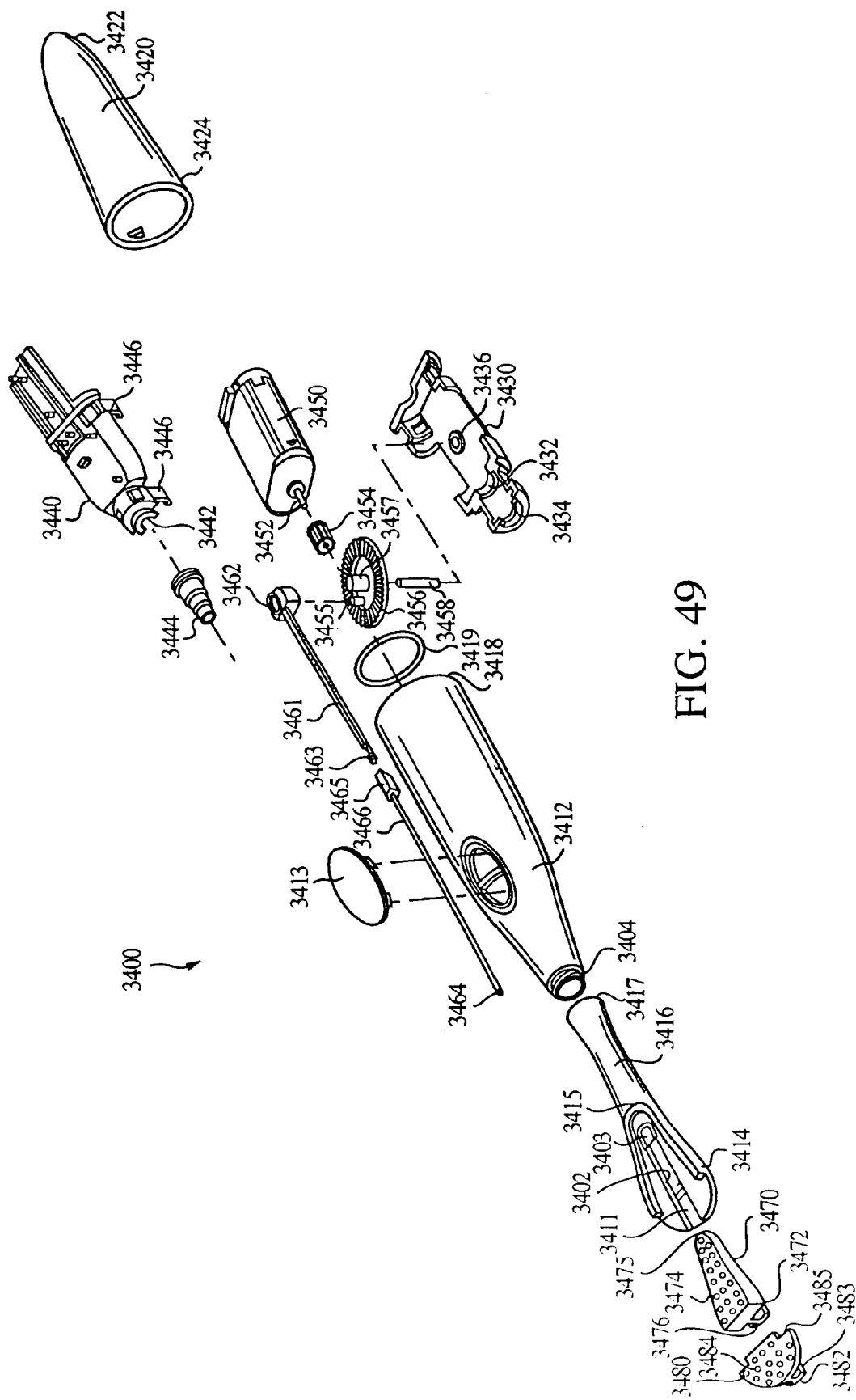
FIG. 49 is a partial exploded view of the toothbrush in accordance with the present invention.

FIG. 49 illustrates another embodiment of the toothbrush 3400 in accordance with the present invention. The toothbrush 3400 includes a body portion 3412, a neck portion 3416, and an end cap 3420. The body portion 3412 defines a first end 3418 and an opposite end 3404 which preferably includes a screw member or threaded region. The end cap 3420 defines a closed end 3422 and an opposite open end 3424. The open end 3424 is sized and configured to releasably engage the end 3418 of the body portion 3412. An O-ring or other sealing member 3419 is preferably used at the interface between the ends 3424 and 3418. The neck 3416 includes an end 3417 and a brush head 3414 preferably integrally formed at the end of the neck 3416 opposite the end 3417. The end 3417 preferably includes provisions for releasably engaging a screw member defined at the end 3404 of the body member 3412. The brush head 3414 preferably includes a first channel member 3411 and an aperture 3403 which provides access to a hollow region extending within the brush head 3414 and neck region 3416. An optional second channel 3402 may be defined along the brush head 3414 which further provides guidance for a movable bristle carrier described in greater detail herein. A guide wall 3415 is preferably defined along the brush head 3414 and may extend around a portion of the periphery of the surface of the brush head.

This embodiment of the toothbrush 3400 further includes a motor 3450 providing a powered drive shaft 3452. An electrical switching circuit and a power source, although not shown, are preferably retained within the hollow region defined within the body 3412 and end cap 3420. A lower motor mount 3430 and an upper motor mount 3440 preferably cradle and retain the motor 3450 within the interior hollow region defined within the body 3412 and end cap 3420. The interior hollow region extends within the neck 3416 and optionally within a portion of the brush head 3414. The lower motor mount 3430 includes a base or aperture 3436 for receiving a pivot or axle member 3458 for a drive gear described in greater detail herein. The lower motor mount 3430 includes an inner drive support 3432 and an outer drive support 3434 as shown. The upper motor mount 3440 includes a drive support 3442 which preferably engages with the inner and/or outer drive supports 3432 and 3434 of the lower motor mount 3430. A drive housing 3444 is also provided which preferably engages the motor mount 3440. A plurality of engagement legs 3446 are preferably formed from the upper motor mount 3440 which engage the lower mount 3430. As previously noted with regard to FIG. 48, it will be appreciated that a one-piece motor mount component may be utilized.

A drive gear 3454 which is secured to the drive shaft 3452 of the motor 3450 is preferably in engagement with a crown gear 3456. The crown gear is rotatably supported by the axle or pivot member 3458 which in turn is received in the base 3436 of lower motor mount 3430. The crown gear 3456 includes a centrally located guide member 3457 and an offset member 3455. The offset member 3455 is engaged with a pinion end 3462 of a drive shaft component 3461. The drive shaft component 3461 includes an end 3463 defined oppositely from the pinion member 3462. Also provided is another drive shaft member 3466 which includes an end 3465 and an opposite end 3464. The end 3465 preferably engages the end 3463 of the drive shaft component 3461. The opposite end 3464 of the drive shaft component 3466 preferably engages a movable bristle carrier described in greater detail herein. The drive shaft components 3466 and 3461 preferably reside within the interior hollow region of the body 3412 and neck 3416. A releasable and protective cover 3413 preferably is attached along a recessed region or one or more apertures defined within the body 3412. The cover 3413 serves as a protective housing or cover for a switch, the position of which may be changed through the cover 3413.

This embodiment of the toothbrush 3400 also comprises a movable bristle carrier 3470 and a stationary bristle carrier tip or end 3480. The movable bristle carrier 3470 defines a plurality of apertures 3474 for receiving and retaining a plurality of bristles and bristle tufts (not shown). The bristle carrier 3470 includes a first end 3475 and an opposite second end 3472. The end 3475 is preferably shaped and sized to fit within the channel 3411 defined along the brush head 3414 and preferably having a similar configuration as the guide wall 3415. The movable bristle carrier 3470 also includes a ridged member 3476 along its underside, sized to engage the channel 3411 defined along the brush head 3414. The distal end 3464 of the drive shaft component 3466 is engaged with the bristle carrier 3470. Preferably, the end 3464 is accessible through aperture 3403 defined in the brush head 3414.

The bristle carrier tip 3480 includes a plurality of apertures 3484 adapted for receiving and retaining bristles or bristle tufts (not shown). The bristle carrier tip 3480 also includes a first end 3485 adapted to face the end 3472 of the movable bristle carrier 3470 and portions of the guide wall 3415 of brush head 3414. The bristle carrier tip 3480 also includes an opposite end 3482 and may further include a ridged member 183 along its underside, to engage and reside within the channel 3411 defined within the brush head 3414. The ridged member 3483 is preferably configured in a similar fashion as the ridged member 3476 of the bristle carrier 3470. Upon assembly, the bristle carrier tip 3480 is secured to the distal end of the brush head 3414.

This embodiment of the toothbrush 3400 operates in a similar fashion as the previously described embodiment of the toothbrush 3300. Upon completion or closure of an electrical circuit between the motor 3450 and a power source, the drive shaft 3452 and drive gear 3454 rotate. Such rotation causes rotation of the crown gear 3456 and imparts a reciprocating motion to the drive shaft members or components 3461 and 3466. Engagement between the drive shaft component 3466 and the bristle carrier 3470 imparts a translating or reciprocating movement to the carrier 3470.

The present invention toothbrushes, and particularly the embodiments of the toothbrush 3300 and 3400, have been found to operate utilizing remarkably minor amounts of power. And surprisingly, these electric toothbrushes provide comparable brushing efficacy and performance as other commercially available toothbrushes. These dramatic gains are believed to result from a combination of one or more of the following factors: (1) the use of translating or reciprocating motion for the movable bristle carrier during operation of the present invention toothbrushes; (2) the selection of the degree or extent of motion of the bristle carrier, i.e. its "stroke"; (3) the particular type of motor utilized in the toothbrushes; (4) the operating speed employed by the motor; (5) the gear ratio between a motor drive gear and a crown gear used in the drive mechanism of the present invention toothbrushes; (6) the particular assembly of components used in the drive mechanism and the relatively few number of components; (7) the use of static bristles in conjunction with movable bristles; and (8) the particular bristle configuration employed along the brush head.

The present invention approach of using a translating plate to impart motion to a plurality of bristles has been found to provide significant improvement in reducing energy consumption and operating current and voltage requirements as compared to currently known electric toothbrush assemblies. For example, comparative tests between (i) Assignee's relatively energy efficient and hugely popular Crest7 Spin Brush7 using an oscillating spin head and (ii) a, translating or reciprocating bristle carrier according to the present invention, reveals the following:

TABLE 2

|  | Spin Head | Translating Plate |
|---|---|---|
| Voltage to Initiate Movement (Under 1 lb. Loading) | >1.8 V | >1.28 V |
| Current Draw at 3.0 V (under 1 lb. Loading) | 0.8 A | 0.5 A |

The data presented in Table 2 illustrates that an embodiment of the toothbrush according to the present invention, utilizing a translating plate or bristle carrier, requires significantly less voltage (approximately 28%) and less amperage (approximately 37%) than a leading commercially successful toothbrush utilizing an oscillating or spin head configuration.

Another aspect of the high efficiency drive mechanisms according to the present invention relates to the stroke length of the movable bristle carrier, such as bristle carriers 3370 and 3470. The preferred parameters of the movement of the reciprocating bristle carrier are as follows. Preferably, the reciprocating carrier has a stroke length at least about 0.5 mm, more preferably at least about 1.0 mm, more preferably at least about 1.25 mm, and most preferably at least about 1.5 mm; and less than about 5 mm, more preferably less than 3.5 mm, more preferably less than 2.5 mm, and most preferably less than 1.7 mm. It will be appreciated that the present invention drive mechanisms may utilize stroke lengths greater or lesser than these various preferred values. Although not wishing to be bound to any particular theory, it is believed that excessive amounts of power, i.e. battery power, are consumed when stroke length is excessively long. And, if stroke length is too short, brushing efficacy is greatly reduced. As previously noted, the direction of movement of the bristle carrier is parallel with the longitudinal axis of the toothbrush.

The motor used in the embodiments of the toothbrush described herein is preferably particularly adapted to provide a high efficiency power source for the drive mechanism. A standard motor may be modified by using less windings and reducing the voltage requirements to about 1.5 volts. Typical standard motors exhibit general current draw characteristics as follows: Without loading, a draw of about 1.06 amps is required, and with loading, a draw of at least 1.0 amp is required. The preferred embodiment motors used in the electric toothbrush embodiments described herein draw less than 0.3 amps without a load, and approximately 0.4 to about 0.6 amps under a load. The "loads" referred to are typical operating loads placed upon the motor when operating the embodiments of the toothbrushes described herein during routine brushing.

The preferred operating speed for the motors used in the embodiments of the toothbrush described herein ranges from about 1500 rpm to about 3500 rpm, and is most preferably about 2500 rpm. An rpm of 2500 provides about 1250 stroke cycles per minute as measured at the reciprocating bristle carrier when utilizing the preferred embodiment drive mechanisms described herein. These operating speeds are given with respect to the motor engaging the drive mechanism, however, no brushing load being placed upon the bristle carrier. It will be appreciated that upon application of a load to the motor, the operating speed of the motor may be reduced by about 30% to about 35%. These values are estimates and the extent of reduction in operating speed will depend upon a host of factors.

This relationship of motor operating speed and bristle carrier stroke speed is an indication of the preferred gear ratio between the drive gear engaged to the drive shaft of the motor (such as drive gear 3354 in FIG. 48 or drive gear 3454 in FIG. 49) and the crown gear (such as crown gear 3356 in FIG. 48 or crown gear 3456 in FIG. 49) to which the drive shaft is engaged at the offset member. The preferred ratio is from about 1:1 to about 3:1, and most preferably about 2:1. Therefore, at this most preferred ratio, for every two revolutions of the motor drive shaft, the crown gear rotates once. The noted preferred gear ratio of 2:1 has been found to provide a desirable combination of range of motion and speed as measured at the bristle carrier to provide excellent brushing characteristics in conjunction with an acceptable level of power consumption.

The use of the noted crown gear in the preferred embodiment drive mechanisms described herein is particularly desirable since that type of drive component, and its orientation shown in the referenced figures, requires relatively few components and enables a relatively small housing to be utilized since the resulting overall volume of the drive mechanism is small. The preferred crown gear used in the drive mechanism described herein utilizes from about 8 or 10 to about 40 gear teeth. Most preferably, the crown gear has about 20 gear teeth. This is a relatively small number of teeth for the given size and application of the crown gear. This results in a relatively tall profile for the gear teeth of the brown gear. Accordingly, the preferred crown gears of the present invention utilize an offset member that must extend above the height of the gear teeth. This is necessary so that sufficient clearance is provided for the gear teeth of the crown gear. The crown gear is rotatably supported by an axle having a height such that the drive shaft engaged with the offset member is aligned with the bristle carrier. This particular arrangement and combination of components provides a drive mechanism utilizing a remarkably few number of components. The fewer the number of components, the more efficient is the transfer of motion and greater ease in assembly and production.

Figure 50:
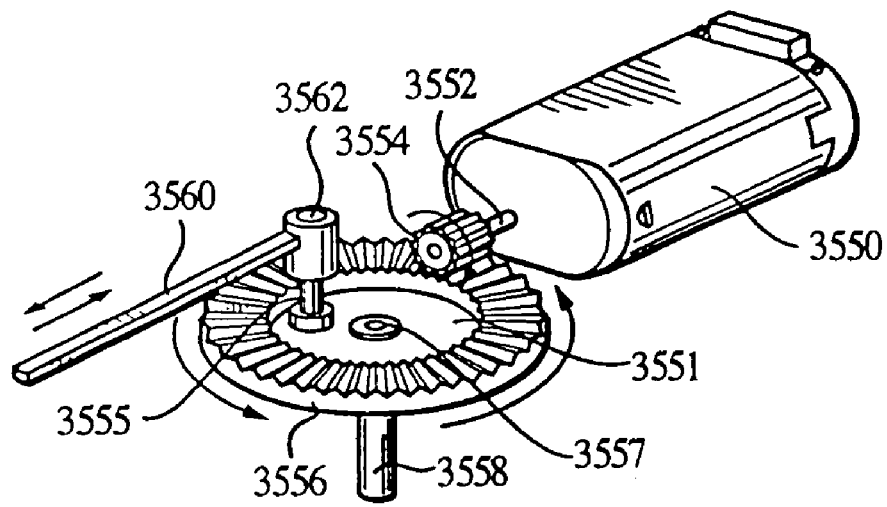
FIG. 50 is a perspective view of a portion of the drive mechanism in accordance with the present invention.

Referring to FIG. 50, a portion of a preferred embodiment drive mechanism is shown. A motor 3550 providing a powered drive shaft 3552 and a drive gear 3554 secured to the shaft 3552 is engaged with a crown gear 3556. The crown gear 3556 is rotatably supported at its center 3557 by an axle 3558. An outwardly extending offset member 3555 is provided along an outer face 3551 of the crown gear 3556. The member 3555 is disposed radially outward from the center 3557 of the crown gear 3556. A drive shaft 3560 is engaged at its end 3562 with the offset member 3555. Upon rotation of the drive shaft 3552 and gear 3554, the crown gear 3556 rotates about axle 3558. That movement in turn imparts a reciprocating motion to the drive shaft 3560.

Figure 51:
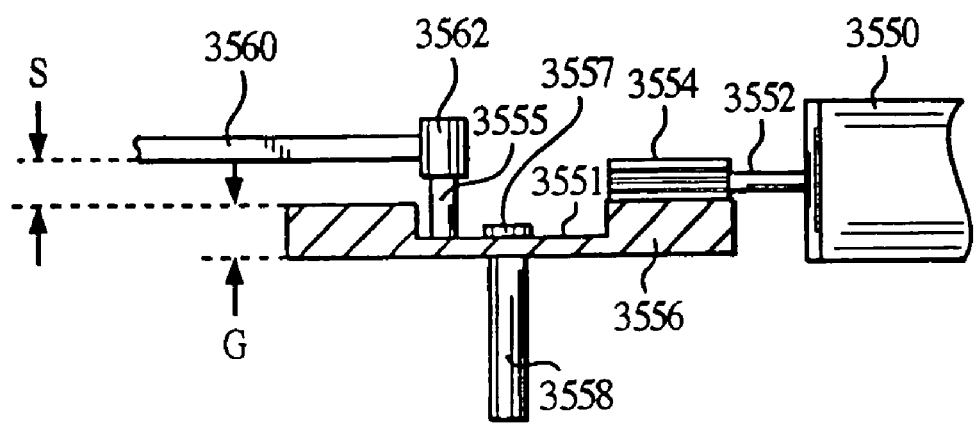
FIG. 51 is a side elevational view of the portion of the drive mechanism illustrated in FIG. 50.

FIG. 51 is a side elevational view of the portion of the preferred embodiment drive mechanism depicted in FIG. 50. FIG. 51 illustrates a feature of the preferred embodiment drive mechanisms, that of the elevated orientation of the reciprocating drive shaft with respect to the crown gear. Specifically, it can be seen that the gear teeth of the crown gear 3556 have a profile or overall height shown as height G. The offset member 3555 is engaged with the drive shaft 3560 such that a distance S is maintained between the shaft 3560 and the gear teeth. Most preferably, the distance S is also the distance necessary to maintain alignment between the offset member 3555 and the bristle carrier disposed on the brush head. Most preferably, the drive shaft 3560 is the only drive component extending between and engaging those components.

As previously noted, another aspect of the embodiments of the toothbrush according to the invention, and particularly, of the drive mechanisms described herein, is that a relatively few number of drive components are utilized. This is readily apparent from the exploded views in FIGS. 48 and 49. This design strategy reduces the number of interconnections and engagements between drive components and so a more direct assembly of drive components is achieved. This approach greatly simplifies assembly, reduces overall costs of production, and leads to a more commercially viable consumer product.

Figure 52:
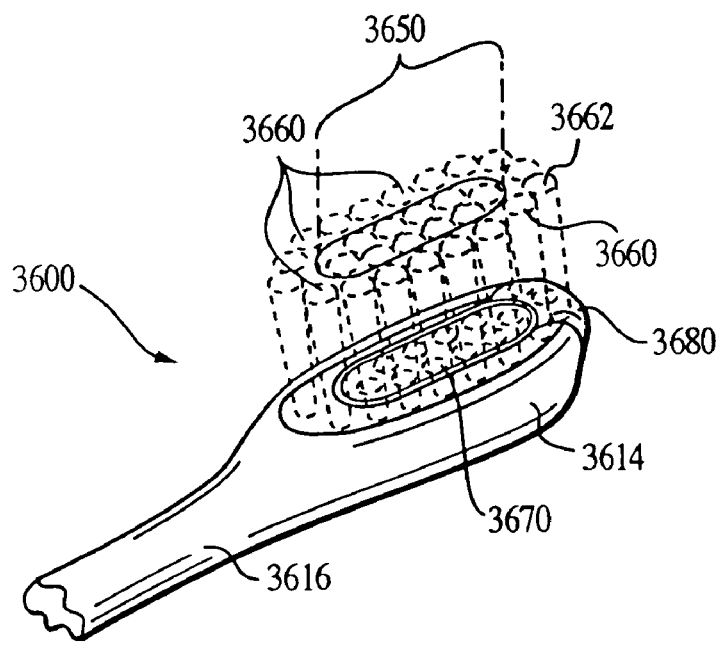
FIG. 52 is a perspective view of the brush head and neck of a toothbrush in accordance with the present invention.
Figure 53:
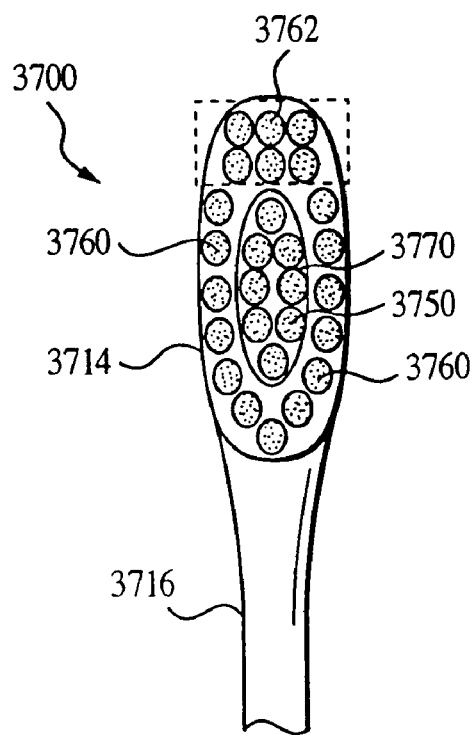
FIG. 53 is a planar view of another brush head and neck of a toothbrush in accordance with the present invention.
Figure 54:
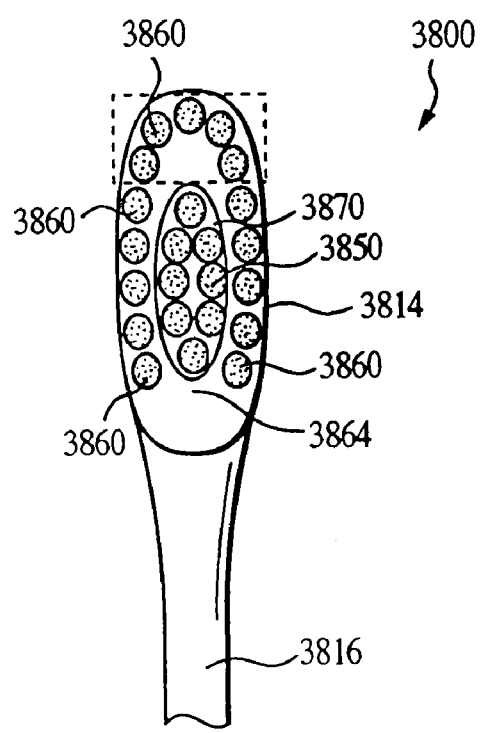
FIG. 54 is a planar view of yet another brush head and neck of a toothbrush in accordance with the present invention.

Additionally, the use of static bristles in combination with a plurality of movable bristles, assists in reducing the overall load on the reciprocating bristle carrier. FIGS. 52-54 illustrate this feature in greater detail. FIG. 52 illustrates a portion of an embodiment of the toothbrush according to the invention 3600 comprising a brush head 3614, a neck 3616, a movable bristle carrier 3670, and an end component 3680. The movable bristle carrier 3670 supports and retains a plurality of bristles 3650, designated herein as movable bristles. These are shown in dashed lines for clarity. The end component 3680 supports and retains a plurality of bristles 3662, designated herein as stationary bristles. Additionally, the brush head 3614 supports and retains a plurality of bristles 3660, also designated herein as stationary bristles, that preferably, are disposed along the periphery of the movable bristle carrier 3670 and the bristles 3650 disposed thereon. The stationary bristles 3662 and 3660 are also shown in dashed lines.

The bristle configuration shown in FIG. 52 is significant in that the plurality of bristles that are stationary, i.e. bristles 3660 and 3662, essentially surround or partly so, the movable bristles 3650 retained on the movable bristle carrier 3670. This configuration has been found to reduce the load otherwise applied to the bristles 3650 and movable bristle carrier 3670 during brushing and operation of the toothbrush 3600. This characteristic is believed to result from the stationary bristles 3660 and 3662 accommodating a portion of the brushing load, otherwise placed upon the bristles 3650 and carrier 3670. The distribution of the brushing load between the stationary bristles 3660 and 3662, and the movable bristles 3650, is determined by a number of factors including, but not limited to: (i) the relative heights of the stationary and movable bristles, (ii) the materials forming the stationary and movable bristles, (iii) the profile of the brushing surface resulting from the distal ends of the stationary and movable bristles, (iv) the respective densities (or bristles per unit area) of the stationary and movable bristles, and (v) the arrangement of the stationary bristles and movable bristles. By adjusting one or more of these factors, the load applied to the movable bristle carrier during brushing may be reduced by, for example, increasing the relative height of the stationary bristles or decreasing the height of the movable bristles. The load applied to the movable bristle carrier may also be reduced by increasing the density of the stationary bristles disposed around the movable carrier. The load may also be reduced by selecting particular materials that exhibit a high degree of stiffness for the stationary bristles as compared to the movable bristles.

FIG. 53 illustrates another embodiment of the toothbrush according to the invention 3700 comprising a brush head 3714, a neck 3716, a movable bristle carrier 3770, a plurality of movable bristles 3750 supported and retained on the carrier 3770, a first plurality of stationary bristles 3760 disposed on the brush head 3714, and a second plurality of stationary bristles 3762 disposed on the end of the brush head 3714. This toothbrush embodiment 3700 utilizes a bristle configuration in which a large number of stationary bristles, such as 3760 and 3762, are disposed around the movable bristles 3750, or substantially so. It will be noted that the group of stationary bristles 3762 are primarily disposed along the end of the brush head 3714. And, the other group of stationary bristles 3760 generally extend around the remaining periphery of the movable bristle carrier 3770. This arrangement has been found to offer good brushing efficacy and significant reductions in brushing loads otherwise applied to the bristles 3750 and thus, the bristle carrier 3770.

FIG. 54 illustrates another embodiment of the toothbrush according to the invention 3800 comprising a brush head 3814, a neck 3816, a movable bristle carrier 3870, a plurality of movable bristles 3850 supported and retained thereon, and a plurality of stationary bristles 3860 extending generally around the periphery of the bristle carrier 3870. In this embodiment, the stationary bristles 3860 extend around at least a majority of the outer periphery of the bristle carrier 3870. Preferably, the bristles 3860 extend continuously, or substantially so, around the movable bristle carrier 3870 and the movable bristles 3850 disposed thereon. It is not necessary that the stationary bristles 3860 be disposed in a region adjacent the movable bristle carrier that is opposite the distal end of the brush head 3814. This region is shown in FIG. 54 as region 3864. This particular bristle arrangement has been found to offer good brushing performance and significant reductions in brushing loads otherwise applied to the bristles 3850 and thus, the bristle carrier 3870.

FIGS. 53 and 54 also illustrate brush heads utilizing different bristle densities along their distal ends, such as in the region of a bristle carrier tip, such as tip 3380 in FIG. 48. These regions are shown in dashed lines. The dashed region of FIG. 53 contains six bristle tufts per unit area whereas FIG. 52 contains five bristle tufts per unit area.

Another significant aspect that the present invention provides is a unique engagement assembly comprising a gear that is driven by the electric toothbrush motor and a drive shaft that powers one or more movable bristle carriers. This engagement assembly efficiently converts rotary motion of the gear to reciprocating motion of the drive shaft. The assembly operates and performs the noted conversion in a remarkably quiet and smooth manner.

Figure 55:
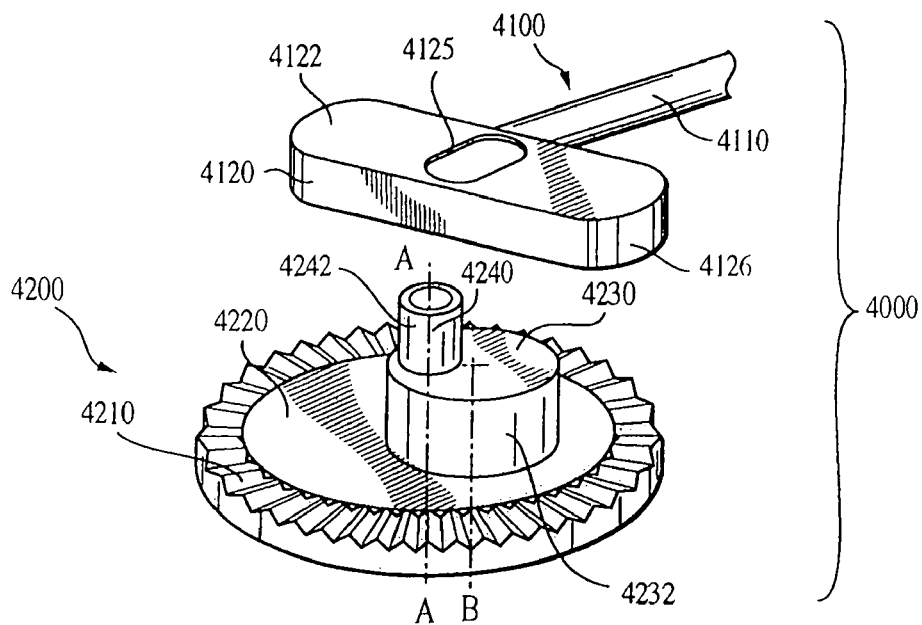
FIG. 55 is a partially exploded view of an engagement assembly for converting rotary motion to reciprocating motion, preferably utilized in the present invention toothbrushes.

This preferred engagement assembly is illustrated in FIGS. 55-60. FIG. 55 illustrates a preferred embodiment assembly 4000 comprising a drive shaft 4100 and a gear 4200. The drive shaft 4100 includes a shaft portion 4110 and a distal end having a partially enclosed elongated end 4120 that, as described below, provides a unique set of surfaces for engagement with cam surfaces of the gear 4200. More specifically, FIG. 55 illustrates an oval-shaped aperture 4125 defined within a central region of the partially enclosed elongated end 4120. The partially enclosed end 4120 includes an end cover 4122 which defines the aperture 4125. Disposed about the periphery of the end cover 4122 is an end wall 4126. Together, the cover 4122 and the wall 4126 provide a partial enclosure (not shown in FIG. 55) that receives certain components of the drive gear 4200.

FIG. 55 also illustrates the preferred gear 4200 of the assembly 4000. The gear 4200 is similar to the gear 806 shown in FIG. 12, gear 3356 shown in FIG. 48, gear 3456 shown in FIG. 49, and gear 3556 shown in FIGS. 50 and 51. That is, the mounting and function of the gear 4200 is similar to the mounting and function of those noted gears. However, the gear 4200 utilizes a unique collection of camming surfaces. Specifically, gear 4200 includes a plurality of gear teeth 4210 disposed about its periphery. A drive gear such as affixed to an electric motor is preferably engaged or otherwise coupled to the gear 4200, and specifically to the gear teeth 4210. A circular medial base 4220 extends along an outward face of the gear 4200 and between opposite regions of the gear teeth 4210. Disposed on the base 4220 and extending outward therefrom is a first cam 4230 providing a circular cam surface 4232 extending about the periphery of the cam 4230. Extending from the first cam 4230 is a second cam 4240. The second cam 4240 provides a circular cam surface 4242 extending about the periphery of the second cam 4240. It will be appreciated that the center of the second cam 4240 coincides with the center of the base 4220, and the center of the gear 4200. Thus, upon rotation of the gear 4200, such as about the axis of rotation A shown in FIG. 55, the second cam 4240 and the base 4220, rotate about the same axis, i.e. axis A. The center of the first cam 4230 is shown in FIG. 55 as axis B, is spaced from, yet preferably parallel to, axis A.

Figure 56:
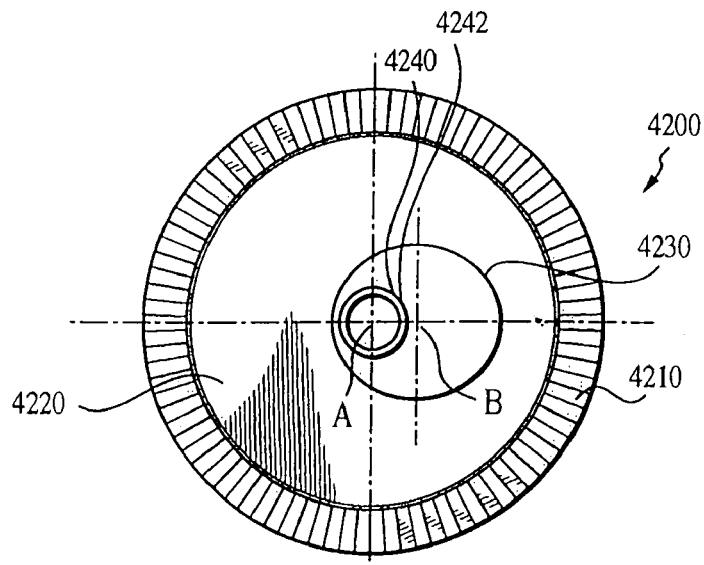
FIG. 56 is a top planar view of a gear of the assembly depicted in FIG. 55.

FIG. 56 is a top planar view of the gear 4200. FIG. 56 illustrates the arrangement of the first cam 4230 and the second cam 4240 with respect to each other, and the center of rotation A of the gear 4200. Again, it will be noted that the center of the circular first cam designated as center B in FIG. 56 is spaced apart from the center (or axis of rotation) A.

Figure 57:
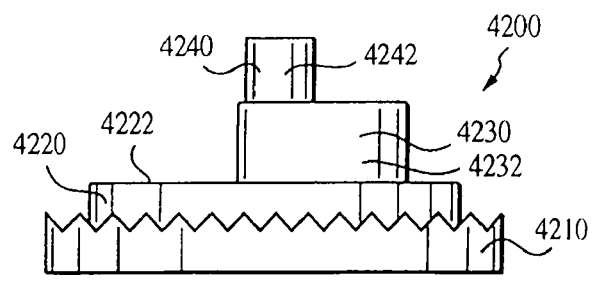
FIG. 57 is a side elevational view of the gear shown in FIG. 56.

FIG. 57 is a side elevational view of the gear 4200. FIG. 57 further illustrates the configuration and arrangement of the gear teeth 4210, base 4220, the first cam 4230 and its cam surface 4232, the second cam 4240 and its cam surface 4242.

Figure 58:
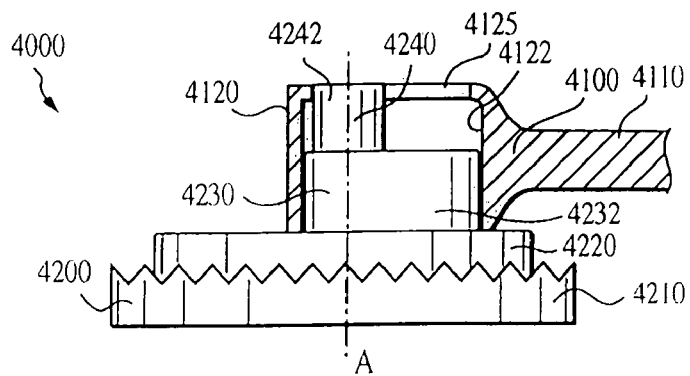
FIG. 58 is a partial cross-sectional view of the assembly of FIG. 55 illustrating the engagement between a drive shaft and the gear.

FIG. 58 is a partial cross-sectional side view of the assembly 4000 illustrating the elongated end 4120 of the drive shaft 4100 engaged with the gear 4200. Specifically, it can be seen that the second cam 4240 is disposed within the aperture 4125 defined in the end 4120. And, the first cam 4230 is enclosed by and received within the end 4120. Preferably, the cam surface 4242 of the second cam 4240 engages and contacts portions of the surface of the elongated end 4120 that defines the aperture 4125. And, preferably, the cam surface 4232 of the first cam 4230 engages and contacts portions of the interior and specifically, portions of an interior wall 4122 defined along the interior of the elongated end 4120.

Figure 59:
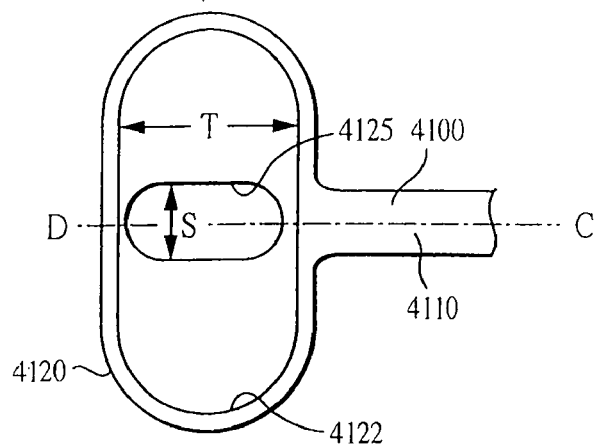
FIG. 59 illustrates the underside of an end of the drive shaft of the assembly of FIG. 55.

FIG. 59 illustrates the underside, i.e. the side of the elongated end 4120 of the drive shaft 4100 that faces the base 4220 of the gear 4200. FIG. 59 further illustrates the interior wall 4122 which the cam surface 4232 of the first cam 4230 engages when the gear 4200 and drive shaft 4100 are engaged to form the assembly 4000. FIG. 59 also illustrates the orientation of the aperture 4125. FIG. 59 additionally illustrates two dimensions S and T as follows.

Dimension S is the minimum span or entrance dimension of the aperture 4125. Since the second cam 4240 is received within the aperture 4125, the diameter of the cam 4240 should be slightly less than dimension S. Alternatively, dimension S should be slightly greater than the diameter of the cam 4240.

Dimension T is the minimum span or entrance dimension of the oval shaped interior wall 4122. Since the first cam 4230 is received within the region generally bounded by the interior wall 4122, the diameter of the cam 4230 should be slightly less than dimension T. Alternatively, dimension T should be slightly greater than the diameter of the cam 4230.

FIG. 59 also illustrates a preferred orientation of the aperture 4125 within the end 4120. As can be seen, the major axis of the oval shaped aperture 4125 depicted as axis D, is preferably parallel and most preferably co-extensive with, the longitudinal axis of the shaft portion 4110 of the drive shaft 4100, depicted as axis C.

FIG. 59 additionally illustrates that the aperture 4125 is preferably oval-shaped and oriented at right angles to the oval-shaped interior region defined by the interior wall 4122. That is, the major axis of the oval shaped aperture 4125 is preferably perpendicular to the major axis of the oval shaped interior region defined by the wall 4122.

Figure 60:
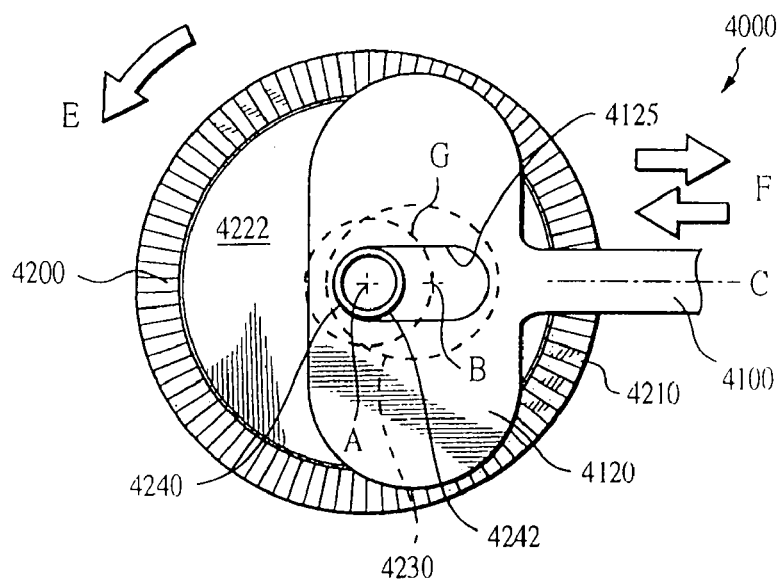
FIG. 60 is a top, planar view of the assembly of FIG. 55 illustrating the operation of that assembly.

FIG. 60 is a top, planar view of the assembly 4000 further illustrating the arrangement, orientation, and configuration of the drive shaft 4100 and the gear 4200. Upon rotation of the gear 4200 about axis A, such as in the direction of arrow E, the center of the first cam 4230 is rotated about axis A generally along the circular path G. Circular path G results from the first cam 4230 being displaced about the axis A as gear 4200 rotates. It will be appreciated that the radius of the circular path G corresponds to the amount of offset or spacing between the center points A and B shown in FIG. 55.

As gear 4200 rotates, thus causing the first cam 4230 to be displaced about axis A, along the circular path G, a portion of the cam surface 4232 of the first cam 4230 engages various regions of the interior wall 4122. This results in the end 4120 being linearly translated back and forth with respect to the center point of gear 4200 and axis A. Restated, this has the effect of causing the second cam 4240 to be linearly translated back and forth within the aperture 4125. However, it will be appreciated that since the gear 4200 is essentially fixed at its point of rotation, i.e. axis A, it is the end 4120 and thus the drive shaft 4100 that is translated back and forth. The rotation of gear 4200 in the direction of arrow E causes reciprocation of the drive shaft 4100 in the direction of arrows F shown in FIG. 60.

The preferred embodiment assembly 4000 efficiently converts rotary motion of the gear 4200 into 100% or substantially so, reciprocal motion of the drive shaft 4100. That is, there is none or only an exceedingly minor degree of motion in a direction other than along the longitudinal axis C of the drive shaft 4100. This characteristic is beneficial in that upon high operating speeds, vibration of the assembly is minimal, or at least maintained to acceptable levels.

In addition to its high operating efficiency characteristics, the embodiments of the toothbrushes described herein also provide relatively high brushing forces. An indication of this is that the embodiments of the toothbrush described herein provide a powered and relatively constant reciprocating stroke motion at their brush head even upon application of heavy loads. For instance, toothbrushes according to the present invention may operate under loads as high as 30 lbs applied to their brush heads and reciprocating bristle carriers.

An example of the relative high efficiency and low power consumption of the preferred embodiment drive mechanisms described herein, relates to battery usage. Nearly all comparable currently available electric toothbrushes require two (2) AA batteries for their operation. The embodiments of electric toothbrushes described herein preferably require only one (1) AA battery. It is remarkable and surprising that the present invention toothbrushes provide the same, or substantially the same, force and power characteristics at their brush heads, i.e. measured at the bristle ends, as comparable commercially available brushes; and yet only require approximately one-half of the power or battery requirements as those same brushes. It will be appreciated that in no way are the present invention toothbrushes limited to utilizing only a single (AA) battery. The present invention toothbrushes may utilize a wide variety of batteries, battery configurations, and power sources. The references to (AA) batteries are provided for ease in understanding and further describing the present invention toothbrushes and their low energy consumption characteristics. Generally, the present invention toothbrushes preferably operate from a voltage source of from about 0.5 volts to about 2.5 volts. More preferably, the present invention toothbrushes operate from a power source providing 1.5 volts. Most preferably, such a power source is rechargeable. Of course, the present invention toothbrushes may utilize disposable batteries. This "low energy consumption" feature is an aspect of the present invention toothbrushes that is particularly appealing from a commerciability standpoint.

An indication of this low energy consumption feature of the present invention toothbrushes is illustrated in the total run time of the toothbrushes. A testing apparatus was assembled in which a fixture and a one (1) pound weight were enclosed in a housing. A toothbrush that is to be tested is secured in the fixture, with its bristles directed upwards. The one pound weight is then placed on the brushing surface of the brush, i.e. the upwardly directed distal ends of the bristles. The surface of the weight corresponds to that of a typical dental surface. The toothbrush is then activated and the total elapsed time is measured until the toothbrush stops operating. Preferably, toothbrushes according to the present invention generally operate at least about 100 minutes, more preferably at least 120 minutes, more preferably at least 140 minutes, more preferably at least 160 minutes, and more preferably at least 180 minutes. It is contemplated that the present invention toothbrushes may operate under the described conditions up to as long as 210 to 220 minutes, and even longer. The foregoing noted testing conditions utilize a single (AA) battery. Generally, these total run times are measured using a voltage source of at least about 0.9 volts to about 2.5 volts, and employing a reciprocating bristle carrier having the noted stroke lengths and speeds.

As previously noted, an additional benefit of the embodiments of the toothbrush described herein is a relatively simple assembly. This results in reduced manufacturing costs. Furthermore, it is contemplated that the preferred embodiment drive assemblies described herein will provide increased reliability due to their simple and straightforward design. And, the relatively few number of components employed in these drive assemblies further reduces the potential for failures at their interconnections.

In the event a pinned engagement assembly is utilized, it is most preferred that the movable bristle carrier define an aperture accessible from its underside, similar to aperture 3254 illustrated in FIG. 47. Such aperture may extend only partially through the thickness of the bristle carrier (as shown in FIG. 47), or may extend entirely through that thickness to the other, top side of the carrier. The drive shaft, and specifically, the distal end, such as end 3206 shown in FIG. 47, is formed to either have a pin or pin-like extension from its distal end, or be adapted to engage a separate pin component. The pin (either a separate component or formed as part of the shaft) is fitted within the aperture defined in the bristle carrier. Other engagement assemblies are contemplated for use in conjunction with the present invention including, but not limited to, multiple pin engagement assemblies, latching mechanisms, threaded fasteners, and assemblies which are affixed together with adhesive or sonic welding.

It is contemplated that the various carriers described herein may be readily replaceable, and preferably, interchangeable with other carriers. Thus, a user could select a particular carrier from an assortment of different types and configurations. Upon selection, the user could readily attach that carrier to a desired toothbrush. Furthermore, it is envisioned that so-called variety packs or sample packs, each containing various types of carriers could be provided separately or in conjunction with an electric toothbrush. For example, if the movable bristle carriers described herein utilize a readily releasable engagement mechanism for connection to the drive mechanism, a collections or assortment of movable carriers could be promoted separately or in conjunction with the electric toothbrush.

It will be appreciated that any of the features and aspects of any of the embodiments of the toothbrush described herein may be combined with one or more of the features and aspects of other embodiments described herein.

The present invention may utilize features, aspects, components, materials, and characteristics from one or more of the following published patent applications or issued patents: WO 01/29128; U.S. Pat. No. 6,000,083; U.S. Des. Pat. No. 432,312; U.S. Des. Pat. No. 433,814; U.S. Pat. Nos. 6,178,579; 6,189,693; 6,311,837; U.S. published patent application 2002/0032941; U.S. Pat. Nos. 6,360,395; and 6,371,294; all of which are hereby incorporated by reference.

Other than the particular materials noted or described herein, the various embodiments of the toothbrush and any components may be formed from conventional materials typically utilized for producing electric toothbrushes. Generally, the handle, neck, brush head, and other structural parts or components are formed from polypropylene. Polymeric blends for these parts or components may be used such as for example blends of ABS and one or more of Celcon™, Acetal™, and/or Delrin™. A wide array of self-lubricating materials are particularly preferred for forming drive train components.

The present invention has been described with reference to particular embodiments. Modifications and alterations will occur to others upon reading and understanding this specification. Although certain arrangements for the static and movable bristles have been shown and described, the present invention includes a variety of other configurations. It is intended that all such modifications and alterations are included insofar as they come within the scope of the appended claims or equivalents thereof.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention

What is claimed is:

1. An electric toothbrush comprising: (a) a handle at a first end of the toothbrush having a motor disposed therein; (b) a neck extending from said handle comprising a receiving member at a second end of the toothbrush, wherein a plurality of carriers engage said receiving member, wherein said plurality of carriers comprises at least one static carrier and at least one movable carrier, wherein said at least one static carrier and said at least one movable carrier independently slidingly engage said receiving member, and wherein said at least one movable carrier is substantially encircled by said at least one static carrier; and (c) a drive shaft operatively connecting said at least one movable carrier to said motor.

2. The electric toothbrush of claim 1, wherein said receiving member is provided with bristles.

3. The electric toothbrush of claim 1, wherein said carriers comprise bristles.

4. The electric toothbrush of claim 1, wherein said carriers are selected from the group consisting of static and movable carriers comprising: brush head tips, static bristle carriers, movable bristle carriers, elastomeric elements, therapeutic elements, tartar control elements, and dental tools, and any combination thereof.

5. The electric toothbrush of claim 1, wherein said carriers comprises a plurality of static bristle carriers.

6. The electric toothbrush of claim 1, wherein said plurality of carriers releasably engage said receiving member.

7. The electric toothbrush of claim 1, wherein said carriers engage said receiving member within channels defined by a surface of said receiving member.

8. The electric toothbrush of claim 1, wherein said at least one movable carrier and said at least one static carrier engages said receiving member within separate channels defined by said surface of said receiving member.

9. The electric toothbrush of claim 1, wherein said at least one movable carrier is nested within said at least one static carrier.

10. The electric toothbrush of claim 1, wherein said at least one static carrier is retained on said receiving member by connectors defined by an outer surface of said receiving member matable with connectors defined by an inner surface of said at least one static carrier.

11. The electric toothbrush of claim 10, wherein said matable connectors further comprise serrated teeth.

12. The electric toothbrush of claim 1, wherein said at least one movable carrier engages said drive shaft by receiving a protuberance of said at least one moveable carrier into an aperture of said drive shaft.

13. The electric toothbrush of claim 1, wherein said at least one movable carrier moves in a direction substantially parallel to said longitudinal axis of said receiving member of the toothbrush.

14. The electric toothbrush of claim 13 wherein said at least one movable carrier reciprocates.

15. The electric toothbrush of claim 1, wherein said receiving member and said neck of the toothbrush are a unitary body.

16. A kit comprising: (a) the toothbrush of claim 1, and (b) at least one carriers selected from the group consisting of brush head tip carriers, static bristle carriers, movable bristle carriers, elastomeric element carriers, oral care composition carriers, and dental tool carriers, and any combination thereof.

17. An electric toothbrush comprising: (a) a handle at a first end of the toothbrush having a motor disposed therein; (b) a neck extending from said handle comprising a receiving member free of bristles at a second end of the toothbrush, wherein said receiving member receives a plurality of bristle carriers to form a toothbrush head, wherein said plurality of bristle carriers comprise at least one static bristle carrier and at least one movable bristle carrier, and wherein said at least one movable bristle carrier is nested within said at least one static bristle carrier, wherein said at least one static bristle carrier and said at least one movable bristle carrier independently slidingly engages said receiving member of said neck, and wherein said at least one movable bristle carrier is substantially encircled by said at least one static bristle carrier; and (c) a drive shaft operatively connecting said at least one movable bristle carrier to said motor.

* * * * *